United States Patent
Samira et al.

(10) Patent No.: US 9,879,076 B2
(45) Date of Patent: Jan. 30, 2018

(54) METHODS AND COMPOSITIONS WITH IMMUNE THERAPY FOR TREATMENT OF DEMENTIA

(71) Applicant: RAMOT AT TEL AVIV UNIVERSITY LTD., Tel Aviv (IL)

(72) Inventors: Sarit Samira, Nes Ziona (IL); Nurit Rachamim, Rishon LeTzion (IL); Michael Tal, Kefar Bilu (IL); Ronald Ellis, Jerusalem (IL); Idan Rakover, Herzliya (IL); Rom E. Eliaz, Lehavim (IL); Beka Solomon, Herzliya (IL); Timothy David Jones, Cambridgeshire (GB); Francis Joseph Carr, Aberdeen (GB); Polina Rabinovich-Toidman, Rehovot (IL); Meital Sooliman, Kfar Saba (IL)

(73) Assignee: RAMOT AT TEL AVIV UNIVERSITY LTD., Tel Aviv (IL)

( * ) Notice: Subject to any disclaimer, the term of this patent is extended or adjusted under 35 U.S.C. 154(b) by 38 days.

(21) Appl. No.: 14/774,974

(22) PCT Filed: Mar. 13, 2014

(86) PCT No.: PCT/US2014/026377
§ 371 (c)(1),
(2) Date: Sep. 11, 2015

(87) PCT Pub. No.: WO2014/151747
PCT Pub. Date: Sep. 25, 2014

(65) Prior Publication Data
US 2016/0017025 A1    Jan. 21, 2016

Related U.S. Application Data

(60) Provisional application No. 61/790,557, filed on Mar. 15, 2013.

(51) Int. Cl.
*C07K 16/18* (2006.01)
*A61K 39/00* (2006.01)
*A61K 38/00* (2006.01)

(52) U.S. Cl.
CPC .............. *C07K 16/18* (2013.01); *A61K 38/00* (2013.01); *A61K 2039/505* (2013.01); *A61K 2039/54* (2013.01); *C07K 2317/24* (2013.01); *C07K 2317/31* (2013.01); *C07K 2317/34* (2013.01); *C07K 2317/41* (2013.01); *C07K 2317/54* (2013.01); *C07K 2317/622* (2013.01); *C07K 2317/71* (2013.01); *C07K 2317/76* (2013.01); *C07K 2317/92* (2013.01)

(58) Field of Classification Search
CPC .............. A61K 38/00; A61K 2039/505; A61K 2039/54; C07K 2317/71; C07K 2317/76; C07K 2317/34; C07K 16/18; C07K 2317/31; C07K 2317/24; C07K 2317/41; C07K 2317/622; C07K 2317/92
See application file for complete search history.

(56) References Cited

U.S. PATENT DOCUMENTS 5,811,286 A * 9/1998 Fallon ...................... C12N 9/78
435/228

OTHER PUBLICATIONS

Vickers. A vaccine against Alzheimer's disease: developments to date. Drugs Aging 2002; 19(7):487-94.*
Perrin et al. Multimodal techniques for diagnosis and prognosis of Alzheimer's disease. Nature Oct. 15, 2009;461(7266):916-22, Published online Oct. 14, 2009.*
Hampel et al. The future of Alzheimer's disease: the next 10 years. Prog Neurobiol. Dec. 2011;95(4):718-28. Epub Nov. 22, 2011.*
Paul W. E. Fundamental Immunology, 3rd edition, 1993, pp. 292-295.*
Rudikoff et al. Single amino acid substitution altering antigen-binding specificity. Proc Natl Acad Sci U S A. Mar. 1982;79(6):1979-83.*

* cited by examiner

*Primary Examiner* — Gregory S Emch
(74) *Attorney, Agent, or Firm* — Browdy and Neimark, PLLC

(57) ABSTRACT

Novel antibodies, methods and compositions for treatment of a disease which is susceptible to amelioration by the blocking of APP cleavage.

29 Claims, 16 Drawing Sheets

METHODS AND COMPOSITIONS WITH IMMUNE THERAPY FOR TREATMENT OF DEMENTIA

FIELD OF THE INVENTION

The present invention relates to methods and compositions featuring novel antibodies against the β-secretase cleavage site of APP (amyloid precursor protein).

BACKGROUND OF THE INVENTION

Alzheimer's disease (AD) is the most common form of dementia. Typically diagnosed in patients over the age of 65, an early onset form of the disease can strike much earlier. With the overall aging of the world's population, the prevalence of AD is expected to increase markedly. Unfortunately, there is no effective treatment or cure.

The extracellular deposition of amyloid peptides in the brains is thought to be a central event in AD pathogenesis. Evidence that amyloid may play an important role in early pathogenesis comes primarily from studies of individuals affected by the familial form of AD (FAD) or by Down's syndrome. The generation of amyloid-β peptide (Aβ) from amyloid precursor protein APP occurs via a regulated cascade of cleavage by at least three proteases (secretases). The recent identification of several such secretases is a major step in understanding the regulation of Aβ formation. An important AD therapeutic goal is the inhibition of these secretases. The theoretical specificity and tractability of protease targets suggest that it should be possible to generate secretase-specific protease inhibitors that penetrate the blood-brain barrier (BBB). Many studies using new knowledge of the ability of the β-secretase (BACE) to identify inhibitors by screening or rational design approaches are underway (U.S. Pat. Nos. 5,744,346; 5,942,400; 6,221,645; 6,313,268; and published PCT applications WO00/47618, WO98/21589, WO96/40885). There is no evidence for additional functions of Aβ, so there are no clear concerns about reduction of this metabolite. Two such secretases are present in many different cells in the body, and it is reasonable to assume that they have substrates besides APP. Consequently, complete inhibition of any one of these enzymes might result in toxicity, particularly during chronic treatment. At the mRNA level, BACE is expressed widely in human brain. Expression is also high in the pancreas, although enzymatic activity in this tissue is low.

Proteolytic processing of APP generates Aβ peptide, which is thought to cause the pathology and subsequent cognitive decline in AD. To initiate Aβ formation, BACE cleaves APP at the N-terminus to release sAPPβ, a ~100-kD soluble N-terminal fragment, and C99, a membrane-bound 12-kD C-terminal fragment that is cleaved by γ-secretase to generate AB peptide. The site of BACE cleavage has been determined. Cleavage by BACE between APP residues 671 and 672, which generates the N-terminal Asp residue of Aβ, is the first cleavage in the cascade that leads to mature Aβ. Extracellular release of Aβ results in the formation of amyloid plaque, while intracellular accumulation of insoluble Aβ and of other APP-derived peptide cleavage products can be toxic to cells.

One FAD family was shown to have a mutation in APP that coincided with the predicted BACE cleavage site. This "Swedish" double mutation results in overproduction of AB peptide when transfected in cells, suggesting that it is a better BACE substrate. A Met→Leu substitution at the P1 position of APP, found in the Swedish FAD mutation that causes early-onset AD, greatly enhances BACE cleavage, but many other substitutions (e.g., Met→Val) decrease BACE cleavage. These findings demonstrate the presence of a BACE activity responsible for a cleavage event that liberates the N-terminus of Aβ peptide and shows that the process is secretory not lysosomal.

SUMMARY OF THE INVENTION

The present invention, in at least some embodiments, provides novel antibodies (Abs), and methods of use and compositions thereof, in which the Abs are raised against the BACE cleavage site of APP and/or otherwise act to block cleavage of APP by BACE.

Such Abs may optionally be used to treat a disease which is susceptible to amelioration by blocking the cleavage of APP.

By "disease which is susceptible to amelioration by blocking the cleavage of APP", it is meant any disease selected from the group including Alzheimer's disease (AD), early onset AD, ALS, Parkinson's disease and other dementias or diseases involving neuronal death, including e.g., Down's Syndrome. Treatment may optionally include prophylactic administration, optionally before the onset of any symptoms.

In at least some embodiments, there are provided pharmaceutical compositions comprising such an Ab. In some embodiments, the pharmaceutical composition is suitable for intravenous, intramuscular, intraperitoneal, intracerebroventricular, nasal, intrathecal, pulmonary, buccal, sublingual, mucosal, rectal, or vaginal administration.

In some embodiments, the antibody is selected from the group consisting of a humanized monoclonal Aβ (mAb), a human mAb, Fab, Fab', F(ab')$_2$, scFv, or dsFv antibody. In some embodiments the Abs of the present invention may be bispecific, trispecific or of greater multi-specificity. In some embodiments, one of this group is selected as one specificity of mAb that becomes part of a bispecific mAb, where the other specificity can include a targeting domain, e.g., to direct binding to the transferrin receptor for facilitating the crossing of the BBB (blood brain barrier) as described by Micklus et al in US Patent Application No. 2002/0025313 (hereby incorporated by reference as if fully set forth herein).

The BBB is formed by a monolayer of tightly connected microvascular endothelial cells with anionic charges. This layer separates two fluid-containing compartments, blood plasma (BP) and extracellular fluid (ECF) of the brain parenchyma, and is surrounded by astroglial cells of the brain. One of the main functions of the BBB is to regulate the transfer of components between BP and ECF. The BBB limits free passage of most molecules from blood to brain. Large highly polar molecules such as proteins generally do not cross the BBB.

Without wishing to be limited by a single hypothesis, such large molecules may optionally be engineered for BBB penetration for example as fusion proteins of the specific molecule and a BBB Molecular Trojan Horse (MTH; Pardridge, 2010a). The MTH is a peptide or peptidomimetic mAb that traverses the BBB via transport on an endogenous receptor-mediated transport system, such as the insulin receptor (IR) or transferrin receptor (TfR). A highly potent BBB MTH is a mAb against the human IR (Boado et al, 2007; Pardridge, 2010b). However, there is no known mAb against mouse IR that can be used as a mouse MTH. Therefore, a surrogate mouse MTH has been engineered, which is a chimeric anti-mouse-TfR mAb called cTfRmAb (Boado et al, 2009). Recently, Yu et al. (2011) demonstrated that a bispecific mouse antibody with a low affinity anti-transferrin receptor antibody as one arm and with an anti-BACE1 antibody as the other arm was able to cross the BBB. Bispecific antibodies can be used as described in the literature (Chan et al., 2010).

According to some embodiments of the present invention, there is provided an Ab able to block the BACE cleavage site of APP. According to some further embodiments of the present invention, there is provided a bispecific Aβ that can cross the BBB (e.g., with specificity for TfR) while also being able to block the BACE cleavage site of APP.

In some embodiments, the Aβ is conjugated to a polysialic acid-containing molecule to form an antibody complex that may improve the bioavailability of the antibody, as described by Benz in US Patent Application No. 20110202000, hereby incorporated by reference as if fully set forth herein. Other methods include but are not limited to the use of a rabies virus glycoprotein (RVG) peptide (US Patent Application No. 20100233084, hereby incorporated by reference as if fully set forth herein).

In some embodiments, the pharmaceutical compositions further comprise excipients and/or carriers. In some further embodiments, the pharmaceutical compositions further comprise additional active or inactive ingredients.

According to some embodiments of the present invention, there are provided host cells comprising an expression vector containing a DNA segment encoding a signal peptide, consensus mouse Heavy (H) chain signal sequences (SEQ ID 56), or consensus mouse Light (L) chain signal sequences (SEQ ID 57), and containing a DNA segment encoding and expressing an Ab, e.g., a mAb or isolated mAb fragments or antigen-binding portions or fragments thereof, as well as transgenic animals having a genome comprising said isolated DNA segment and/or the expression vector.

The terms "expression vector" and "recombinant expression vector" as used herein refer to a DNA molecule, for example a plasmid or modified virus, containing a desired and appropriate nucleic acid sequence necessary for the expression of the recombinant polypeptides in a host cell. As used herein, "operably linked" refers to a functional linkage of at least two sequences. Operably linked includes linkage between a promoter and a second sequence, for example a nucleic acid of the present invention, wherein the promoter sequence initiates and mediates transcription of the DNA sequence corresponding to the second sequence.

The regulatory regions necessary for transcription of the polypeptides can be provided by the expression vector. The precise nature of the regulatory regions needed for gene expression may vary among vectors and host cells. Generally, a promoter is required which is capable of binding RNA polymerase and promoting the transcription of an operably-associated nucleic acid sequence. Regulatory regions may include those 5' non-coding sequences involved with initiation of transcription and translation, such as the TATA box, cap sequence, CAAT sequence, and the like. The non-coding region 3' to the coding sequence may contain transcriptional termination regulatory sequences, such as terminators and polyadenylation sites. A translation initiation codon (ATG) may also be provided.

In order to clone the nucleic acid sequences into the cloning site of a vector, linkers or adapters providing the appropriate compatible restriction sites are added during synthesis of the nucleic acids. For example, a desired restriction enzyme site can be introduced into a fragment of DNA by amplification of the DNA by use of PCR with primers containing the desired restriction enzyme site.

An alternative method to PCR is the use of a synthetic gene. The method allows production of an artificial gene that comprises an optimized sequence of nucleotides to be expressed in host cells of a desired species (e.g., CHO cells or *E. coli*). Redesigning a gene offers a means to improve gene expression in many cases. Rewriting the open reading frame (ORF) is possible because of the redundancy of the genetic code. Thus it is possible to change up to about one-third of the nucleotides in an ORF and still produce the same protein. For a typical protein sequence of 300 amino acids, there are over 10150 codon combinations that will encode an identical protein. Using optimization methods such as replacing rarely used codons with more common codons can result in dramatic effects. Further optimizations such as removing RNA secondary structures can also be included. Computer programs are available to perform these and other simultaneous optimizations. A well-optimized gene can dramatically improve protein expression. Because of the large number of nucleotide changes made to the original DNA sequence, the only practical way to create the newly designed gene is to use gene synthesis.

An expression construct comprising a polypeptide sequence operably associated with regulatory regions can be directly introduced into appropriate host cells for expression and production of polypeptide per se or as a recombinant fusion protein. The expression vectors that may be used include but are not limited to plasmids, cosmids, phage, phagemids or modified viruses. Typically, such expression vectors comprise a functional origin of replication for propagation of the vector in an appropriate host cell, one or more restriction endonuclease sites for insertion of the desired gene sequence, and one or more selection markers.

The recombinant polynucleotide construct comprising the expression vector and a polypeptide according to the invention should then be transferred into a host cell where it can replicate (for example in a bacterial cell), and then be transfected and expressed in an appropriate prokaryotic or eukaryotic host cell. This can be accomplished by methods known in the art. The expression vector is used with a compatible prokaryotic or eukaryotic host cell which may be derived from bacteria, yeast, insects, mammals and humans.

The term "subject" refers to human patients or other vertebrate patients, in particular mammals, and includes any individual for whom it is desired to examine or treat using the methods according to the present invention. However, it will be understood that "patient" does not automatically imply that symptoms or diseases are present. As used herein, the term "patient" preferably refers to a human in need of treatment, e.g., to treat dementia or a related disease.

The term "treatment" as used herein refers to therapeutic treatment of a disease or disorder in a subject. In some embodiments, the term treatment also refers to prophylactic or preventive measures. Those in need of treatment include those already with the disorder as well as those in which the disorder is to be prevented. Hence, a subject to be treated herein may have been diagnosed as having the disorder or may be predisposed or susceptible to the disorder. Thus, the term "treatment" or "treating" herein encompasses curative treatment, preventive treatment as well as palliative treatment, more specifically palliative treatment and curative treatment.

The phrase "pharmaceutically acceptable" refers to molecular entities and compositions that are physiologically tolerable and do not typically produce an allergic or similar untoward reaction, such as gastric upset, dizziness and the like, when administered to a patient in particular to a human.

The expression "effective amount" is an amount sufficient to effect beneficial or desired results including, without limitation, clinical results, preventing or attenuating symptoms resulting from the disease, or decreasing the dose of other medicaments required to treat the disease. An effective amount can be administered in one or more administrations of the active substance.

The term "antigen" refers to a molecule or a portion of a molecule capable of being bound by a selective binding agent, such as an Ab, and additionally capable of being used in an animal to elicit the production of Abs capable of binding to an epitope of that antigen. An antigen may have one or more epitopes.

The term "antibody", as used herein, refers to a protein which may, for example, be produced by the immune system that protects the organism against an antigen. But, as used herein, the term encompasses not only intact mAbs but also fragments thereof, single chains, mutants thereof, naturally occurring variants, fusion proteins comprising an Aβ portion with an antigen recognition site of the required specificity, humanized Abs, bispecific antibodies, and any other modified configuration of the immunoglobulin molecule that comprises an antigen recognition site of the required specificity, as well as Abs produced by mammalian or bacterial cells that carry Ab-encoding DNA sequences, and also recombinant Abs that are made in transgenic animals carrying such sequences.

The term "antibodies" and "immunoglobulins" (Igs) are glycoproteins having the same structural characteristics. While Abs exhibit binding specificity to a specific antigen, Igs include both Abs and other Ab-like molecules lacking known antigen specificity. Polypeptides of the latter kind are, for example, produced at low levels by the lymph system and at increased levels by myelomas.

The term "native antibodies and immunoglobulins" as used herein refers to heterotetrameric glycoproteins of about 150 kilodaltons, composed of two identical light (L) chains and two identical heavy (H) chains. Each L chain is linked to a H chain by one covalent disulfide bond, while the number of disulfide linkages varies between the H chains of different Ig isotypes. Each H and L chain also has regularly spaced intrachain disulfide bridges. Each H chain has at one end a variable domain (VH) followed by a number of constant (CH) domains. Each L chain has a V domain at one end (VL) and a C domain at its other end (CL); the CL domain is aligned with the first CH domain, and the VL domain is aligned with the VH domain. Particular amino acid residues are believed to form an interface between the VL and VH domains (Chothia et al, 1985; Novotny and Haber, 1985; Chothia et al, 1989).

The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyl-terminus in the following order: FR1, CDR1, FR2, CDR2, FR3, CDR3, FR4.

The VH and VL domains contain a binding domain that interacts with an antigen. The C regions may mediate the binding of the Ig to host tissues or factors, including cells of the immune system (e.g., effector cells) and the first component (Clq) of the classical complement system.

The terms "monoclonal antibody" (mAb) or "monoclonal antibody composition" as used herein refer to a preparation of Aβ molecules of single molecular composition. A mAb composition displays a single binding specificity and affinity for a particular epitope. Higher affinity is usually desired for a mAb in order to increase the strength and specificity of binding to its target molecule for increasing efficacy in clinical disease. The term "epitope" means a protein determinant capable of specific binding to an Ab. Epitopes usually consist of chemically active surface groupings of molecules such as amino acids or sugar side chains and usually have specific three-dimensional structural characteristics, as well as specific charge characteristics.

The phrases "an antibody recognizing an antigen" and "an antibody specific for an antigen" are used interchangeably herein with the term "an antibody which binds specifically to an antigen."

The term "antigen-binding portion" of an Aβ (or simply "antibody portion"), as used herein, refers to one or more fragments of an intact Aβ that retain the ability to specifically block cleavage of APP by BACE. It has been shown that the antigen-binding function of an Ab can be performed by fragments of a full-length Ab, for example (i) a Fab fragment, a monovalent fragment consisting of the VL, VH, CL and CH1 domains; (ii) a F(ab)'$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single Aβ arm, (v) a dAb fragment consisting of a VH domain; (vi) an isolated CDR; and (vii) a nanobody, which contains a single VH domain and two CH domains. Although the VL and VH domains of the Fv fragment are encoded by separate genes, they can be joined using recombinant methods by a synthetic linker that enables their synthesis as a single protein chain in which the VL and VH regions pair to form monovalent scFv, which are also intended to be encompassed within the term "antigen-binding portion" of an Ab. These Aβ fragments are obtained using conventional techniques known to those in the art, and the fragments are screened for utility in the same manner as are intact Abs.

Variants of the CDRs, VH or VL regions, H or L chains of antibodies that block the BACE cleavage site on APP, such as the antibodies F5.100 and F5.87 disclosed in the Examples below, and that do not substantially reduce, but preferably increase, the antigen binding properties of such anti-BACE cleavage site antibodies, are contemplated within the scope of the present invention. These variants have 1, 2, 3, 4, 5, 6, 7, 8, 9 or 10 conservative amino acid substitutions or have an amino acid sequence identity of 90% or more, 95% or more, 98% or more, or 99% or more in the CDRs, VH or VL regions, H or L chains. Six classes of amino acid side-chains exist; within one group, the amino acid side chains are chemically similar. Substitution of one amino acid side chain for another one within the same group is known as a "conservative" substitution. "Conservative" amino acid substitutions are well known in the art, and such substitutions are preferably those changes, e.g., substituting one amino acid with another of the same charge and size, which would not be expected to change the antigen binding of the antibody to the BACE cleavage site on APP and are usually the first to be screened since these would not be expected to substantially change the size, charge or configuration of the antibody and thus would be less likely to change the antigen binding properties thereof.

The term "fragments" as used herein refers to sequences sharing at least 10% amino acids in length with the respective sequence of full-length mAb. These sequences can be used as long as they exhibit the same properties as the native sequence from which they are derived. In some embodiments, a fragment can be at least 6 amino acids in length, and can be, for example, at least 8, at least 10, at least 12, at least 14, at least 16, at least 18, at least 20, or at least 25 amino acids or greater than 25 amino acids from the full-length mAb from which it was derived. In some embodiments, the term "fragment" encompasses at least 6, 10, 20, 50, 100, 250, 500 amino acids from the full-length mAb. Exemplary fragments include C- or N-terminal truncations, or truncations of both the C- and N-termini (e.g., 1, 2, 3, 4, 5, 8, 10, 15, 20, 25, 40, 50, 75, 100 or more amino acids deleted from the N- or C-terminus or both). Preferably these sequences share more than 70%, preferably more than 80%, in particular more than 90% amino acids in length with the respective sequence of the mAb. In some embodiments, the term "fragments" as used herein, when used in reference to mAb fragments or antigen-binding portions or fragments usually refers to a portion of at least 2, or at least about 4, or at least about 6, or at least about 8, or at least about 10 or more consecutive amino acids of the epitope binding region of an Ab. In some embodiments, a fragment includes at least 2, or at least about 4, or at least about 6, or at least about 8, or at least about 10 or more consecutive amino acids of the epitope binding region of an Aβ having a sequence as described herein. In some embodiments, a fragment is a CDR region of at least 3 consecutive amino acids from any Aβ sequence described herein. In some embodiments, a fragment is a CDR region selected from any one or a combination of CDRs listed herein.

The term Kabat numbering scheme is a widely-adopted standard for numbering the Aβ residues in a consistent manner, see, for example, bioinf.org.uk/abs. It is based on sequence variability and is most commonly used to define the CDR sequence.

In some embodiments, the fragment is a functional fragment, where a "functional fragment" as used in the context of a "functional fragment of an antibody" refers to an Ab fragment that specifically binds to the same antigen with the same or greater affinity as compared to the full-length Ab. In some embodiments, a functional fragment is a CDR region of at least 3 consecutive amino acids as described herein. In some embodiments, a functional fragment is a CDR region is selected from any one or a combination of CDRs, according to the CDR sequences provided herein.

In the case of an Ab, e.g., mAb according to at least some embodiments of the present invention, useful fragments include, but are not limited to: a CDR region of the H or L chain; a V domain of an H or L chain; a portion of an Aβ chain or only its V region including two CDRs, and the like. In some embodiments, useful functional fragments include, but are not limited to, at least one or any combination of CDRs from the same Ab, as described herein.

Suitable Abs, e.g., mAb, or fragments of the invention are immunologically functional Igs. The term "immunologically functional immunoglobulin fragment" as used herein refers to a polypeptide fragment that is optionally and preferably capable of immunologically interacting with and blocking cleavage of APP. Such interaction optionally and preferably comprises specifically binding to the cleavage site of APP.

In one embodiment, the present invention concerns a method for producing one or more Abs, e.g., mAbs or isolated mAb fragments or antigen binding portions or fragments thereof. In some embodiments, such an Aβ can also be produced by the method comprising the steps of:

(a) producing an antigen related to APP, or a fragment, or a fusion protein thereof, of any species, e.g., human and/or vertebrate species;

(b) immunizing a rodent, e.g., mice, with the antigen or a fragment or a fusion protein thereof;

(c) detecting specifically binding or blocking antibodies in mouse serum;

(d) producing hybridomas between lymph node cells from the mice and myeloma cells to produce antibodies; and (e) transplanting the genes or genetically modified versions (e.g., chimeric, humanized, human) of the genes encoding the mAb to a cell line (e.g., Chinese hamster ovary cells) that is suitable for large-scale fermentations and isolation of large quantities of mAb suitable for clinical evaluations and commercialization, and confirming the expression on such genes by means of a suitable binding assay.

In some embodiments, an antigen used to produce an antibody is human, or mouse, or is from another mammalian species, or from another vertebrate species.

In some embodiments, the antigen used to produce an antibody is a cell line naturally expressing full-length antigen or a fragment of the antigen, or a fusion protein of the antigen and another protein, or the antigen is part of a virus-like particle.

In some embodiments, the antigen used to produce the antibody is expressed in a cell line syngeneic with the mice of step b), or the antigen used to produce antibodies is fused to the Fc portion of an IgG.

In some embodiments, the antigen used to produce antibodies is human or mouse antigen fused to the Fc portion of human IgG1.

As an alternative to steps b), c) and d), an antibody, or fragment thereof such as single chain Fv can be obtained by selecting antibody sequences by phage display on the antigen of step a).

In some embodiments, the binding assays of step e) is carried out by applying visualizing methods comprising enzyme-linked immunosorbent assay (ELISA), dot blot, immunoblot, RIA, immunoprecipitation, flow cytometry, fluorescence microscopy, electron microscopy, confocal microscopy, calorimetry, surface plasmon resonance, test of Ouchterlony, complement-mediated lysis of red blood cells, antibody-dependent cell cytotoxicity and the like. Preferably, the binding assays of step e) are carried out by direct or capture ELISA.

In particular, antibodies can be purified, for example by protein A or G affinity chromatography, anti-mouse IgG antibody-based affinity chromatography, ion exchange, ethanol or ammonium sulfate precipitation and the like.

Methods for preparing an immunogen and immunizing an animal for the preparation of mAb are well-known in the art (Kohler et al, 1975; Brown et al, 1981; Brown et al., 1980; Yeh et al., 1976; Yeh et al., 1982; Kozbor et al, 1983; Cole et al., 1985; U.S. Pat. No. 4,816,567; Clackson, et al, 1991; Marks et al, 1991). Examples of other methods that may be employed for producing mAbs include, but are not limited to, the human B-cell hybridoma technique (Kozbor et al, 1983; Cole et al, 1983), and the EBV-hybridoma technique (Cole et al, 1985). Such mAbs may be of any immunoglobulin class including IgG, IgM, IgE, IgA, IgD and any subclass thereof. The hybridoma producing the mAb of the present invention may be cultivated in vitro or in vivo.

The term "mutant" or "variant" as used herein in reference to an amino acid, DNA or RNA sequence means that such a sequence differs from, but has sequence identity with, the wild type or disclosed sequence. The degree of sequence identity between the wild type or disclosed sequence and the mutant sequence is preferably greater than about 50%, and in many cases is about 60%, 70%, 80%, 90%, 95, 98% or more.

The amino acid residues referred to herein encompass the natural coded amino acids represented by either one-letter or three-letter codes according to conventions well known in the art. In chemical synthesis, amino acid derivatives and D isomers can also be used. In chemical synthesis, sequential, divergent and convergent synthetic approaches to the peptide sequence may be used.

The terms "protein" and "polypeptide" are used interchangeably herein to refer to amino acids joined to each other by peptide bonds or modified peptide bonds, i.e., peptide isosteres, and may contain modified amino acids other than the 20 gene-encoded amino acids. The polypeptides may be modified by either natural processes, such as post-translational processing, or by chemical modification techniques which are well known in the art. Modifications, pre- or post-translational, can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications.

Modifications of polypeptides and amino acids include acetylation; acylation; ADP-ribosylation; amidation; covalent attachment of non-peptide molecules such as flavin, a heme moiety, a nucleotide or nucleotide derivative, a lipid or lipid derivative, or a phosphytidylinositol; cross-linking cyclization; disulfide bond formation; demethylation; formation of covalent cross-links; formation of cysteine; formation of pyroglutamate; formylation; gamma-carboxylation; glycosylation; GPI anchor formation; hydroxylation; iodination; methylation; myristolyation; oxidation; pegylation; proteolytic processing; phosphorylation; prenylation; racemization; selenoylation; sulfation; and transfer-RNA mediated addition of amino acids to protein such as arginylation (see for example, Creighton, T. E., Proteins-Structure and Molecular Properties 2nd Ed., W. H. Freeman and Company, New York (1993); Posttranslational Covalent Modification of Proteins, B. C. Johnson, Ed., Academic Press, New York, pp. 1-12 (1983)).

As used herein, "heterologous" refers to two biological components that are not found together in nature. The components may be proteins or fragments thereof, host cells, genes or control sequences such as promoters. Although the heterologous components are not found together in nature, they can function together, such as when a promoter heterologous to a gene is operably linked to the gene.

The terms "polynucleotide", "nucleic acid sequence" and "nucleic acid" are used interchangeably herein to refer to polymeric forms of nucleotides of any length, either ribonucleotides or deoxynucleotides, including but are not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. Further included are mRNA or cDNA that comprise intronic sequences (see, e.g., Niwa et al., 1999). The backbone of the polynucleotide can comprise sugars and phosphate groups (as typically be found in RNA or DNA), or modified or substituted sugar or phosphate groups. Alternatively, the backbone of the polynucleotide can comprise a polymer of synthetic subunits such as phosphoramidites and thus can be an oligodeoxynucleoside phosphoramidate or a mixed phosphoramidate-phosphodiester oligomer (see e.g., Peyrottes et al., 1996; Chaturvedi et al., 1996). A polynucleotide may comprise modified nucleotides, such as methylated nucleotides and nucleotide analogs, uracil, other sugars, and linking groups such as fluororibose and thioate, and nucleotide branches. The sequence of nucleotides may be interrupted by non-nucleotide components. A polynucleotide may be further modified after polymerization, such as by conjugation with a labeling component, capping, substitution of one or more of naturally occurring nucleotides with an analog, and introduction of means for attaching the polynucleotide to proteins, metal ions, labeling components, other polynucleotides, or a solid support.

The terms "coding sequence of" and "coding region of", in reference to a particular polypeptide or protein, are used interchangeably herein to refer to a nucleic acid sequence which is transcribed and translated into the particular polypeptide or protein when placed under the control of appropriate regulatory sequences.

The term "polynucleotide sequence encoding a polypeptide" encompasses a polynucleotide which includes only coding sequence for the polypeptide, as well as a polynucleotide which includes additional coding and/or non-coding sequence. Examples of additional coding sequences include leader or secretory sequences. Examples of non-coding sequences or regulatory sequences such as promoters, transcription enhancers, etc., are well known in the art.

The term "identity", as used herein and as known in the art, is a relationship between two or more polypeptide sequences or two or more polynucleotide sequences, as determined by comparing the sequences.

The term "identity" also means the degree of sequence relatedness between polypeptide or polynucleotide sequences, as the case may be, as determined by the match between strings of such sequences. "Identity" and "similarity" can be readily calculated by known methods, described for example in, Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math 1988, 48:1073).

Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux et al., 1984), BLASTP, BLASTN, and FASTA (Atschul et al., 1990). The BLAST X program is publicly available from NCBI and other sources (BLAST Manual, Altschul, S., et al., NCBI NLM NIH Bethesda, Md. 20894; Altschul et al., 1990). As an illustration, by a polynucleotide having a nucleotide sequence having at least, for example, 95% "identity" to a reference nucleotide sequence, it is intended that the nucleotide sequence of the tested polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, a polypeptide having an amino acid sequence having, for example, 95% identity to a reference amino acid sequence means that the test amino acid sequence of the polypeptide is identical to the reference sequence except that the polypeptide sequence may include up to five amino acid alterations per each 100 amino acids of the reference amino acid. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

The phrase "substantially identical" in the context of two nucleic acids or polypeptides, refers to two or more sequences that have at least 50%, 60%, 70%, 80%, and in some aspects 90-95% nucleotide or amino acid residue identity, when compared and aligned for maximum correspondence, as measured using one of the known sequence comparison algorithms or by visual inspection. Typically, the substantial identity exists over a region of at least about 100 residues, and most commonly the sequences are substantially identical over at least about 150-200 residues. In some embodiments, the sequences are substantially identical over the entire length of the coding regions.

A "substantially identical" amino acid sequence is a sequence that differs from a reference sequence by one or more conservative or non-conservative amino acid substitutions, deletions, or insertions, and provided that the polypeptide essentially retains its functional and/or immunogenic and/or antibody binding properties. A conservative amino acid substitution, for example, substitutes one amino acid for another of the same class (e.g., substitution of one hydrophobic amino acid, such as isoleucine, valine, leucine, or methionine, for another; or substitution of one polar amino acid for another, such as substitution of arginine for lysine, glutamic acid for aspartic acid, or glutamine for asparagine).

The term "oligonucleotide" refers to either a single-stranded polydeoxynucleotide or two complementary polydeoxynucleotide strands which may be chemically synthesized. Synthetic oligonucleotides generally lack 5' phosphate and thus will not ligate to another oligonucleotide without adding a phosphate with an ATP in the presence of a kinase.

The term "primer" as used herein refers to an oligonucleotide which is capable of acting as a point of initiation of nucleic acid synthesis when placed under conditions in which synthesis of a primer extension product which is complementary to a nucleic acid strand is induced, i.e., in the presence of nucleotides and an inducing agent such as DNA polymerase and at a suitable temperature and pH. Primers may be obtained from a biological source, as in a purified restriction digest of genomic DNA, or produced synthetically. The primers are preferably single stranded for maximum efficiency in amplification, but may alternatively be double-stranded. If double-stranded, the primer is first treated to separate its strands before being used to prepare amplification products. Preferably, the primers are oligodeoxyribonucleotides but must be sufficiently long to prime the synthesis of extension products in the presence of the inducing agent. The exact lengths of the primers will depend on many factors, including temperature, source of primer and use of the method. The primers typically contain 10 or more nucleotides.

Synthetic oligonucleotide primers may be prepared using any suitable method, such as, for example, the phosphotriester and phosphodiester methods (Narang et al, 1979; Brown et al, 1979) or automated embodiments thereof. In one such automated embodiment, diethylphosphoramidites are used as starting materials and may be synthesized as described by Beaucauge et al (1981). One method for synthesizing oligonucleotides on a modified solid support is described in U.S. Pat. No. 4,458,066 which is incorporated herein by reference.

The term "digestion" in reference to a nucleic acid, in particular a DNA molecule, refers to catalytic cleavage of the DNA with a restriction enzyme that acts only at certain sequences in the DNA. The various restriction enzymes used herein are commercially available and their reaction conditions, cofactors and other requirements may be readily ascertained by the ordinarily skilled artisan. After digestion, gel electrophoresis may be performed to isolate the desired fragment, the latter of which is also referred to as a "restriction fragment".

As used herein, the term "isolated" means that the material is removed from its original environment. The original environment may be a natural environment if the material is naturally occurring, for example in a bacterial cell wall, or the original environment may be an artificial environment, if the material is artificial or engineered. For example, a naturally occurring polynucleotide or polypeptide present in a living organism, when separated from some or all of the coexisting materials in the natural system, is isolated. Similarly, a recombinantly engineered polynucleotide or the corresponding expressed polypeptide, are referred to as isolated, when separated from a vector or expression system respectively containing the recombinant polynucleotide or expressed polypeptide.

As used herein, the term "purified" does not require absolute purity; rather, it is intended as a relative definition. The purified nucleic acid sequences of the invention have been purified from other sequences, such as the remainder of genomic DNA or from other sequences in a library or other environment by at least one order of magnitude, typically two or three orders, and more typically four or five orders of magnitude, to a sufficient degree that enables further manipulation of the specific DNA sequence.

As used herein, the term "recombinant", in reference to a nucleic acid, means that the nucleic acid is adjacent to a "backbone" nucleic acid to which it is not adjacent in its natural cellular or viral environment. Backbone molecules according to the invention include nucleic acids such as expression vectors, self-replicating nucleic acids, viruses, integrating nucleic acids, and other vectors or nucleic acids used to maintain or manipulate a nucleic acid insert of interest.

As used herein, the term "recombinant", in reference to polypeptides or proteins, means polypeptides or proteins produced by recombinant DNA techniques, i.e., produced from cells transformed by an exogenous DNA construct encoding the desired polypeptide or protein.

As used herein, "host cell" refers to a cell which has been transformed or transfected, or is capable of transformation or transfection by an exogenous polynucleotide sequence, either in the form of a recombinant vector or other transfer DNA, and includes the progeny of the original cell which has been transfected or transformed.

As used herein, the term "control sequence" refers to a nucleic acid having a base sequence which is recognized by the host organism to effect the expression of encoded sequences to which they are ligated. The nature of such control sequences differs depending upon the host organism; in prokaryotes, such control sequences generally include a promoter, ribosomal binding site, terminators, and in some cases operators; in eukaryotes, generally such control sequences include promoters, terminators and in some instances, enhancers. The term control sequence is intended to include at a minimum, all components whose presence is necessary for expression, and may also include additional components whose presence is advantageous, for example, leader sequences.

As used herein, the term "operably linked" refers to sequences joined or ligated to function in their intended manner. For example, a control sequence is operably linked to coding sequence by ligation in such a way that expression of the coding sequence is achieved under conditions compatible with the control sequence and host cell. For example, a promoter sequence is "operably linked to" a coding sequence when RNA polymerase which initiates transcription at the promoter will transcribe the coding sequence into mRNA.

As used herein, the term "synthetic" in reference to polypeptides or protein sequences, means those that are those prepared by chemical synthesis. Sequential, divergent and convergent synthetic approaches may be used in chemical synthesis.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following Detailed Description of the Invention and the Drawings.

BRIEF DESCRIPTION OF THE DRAWINGS

FIG. 1A shows dose-dependent inhibition of production of extracellular $A\beta$. APP over-expresser CHO cells were incubated in a 24-well plate with each of the four indicated concentrations of each mAb (BBS1 or BBS3). The medium (containing secreted $A\beta$) was collected after 24 hours, and $A\beta$ was measured in a sandwich ELISA. The graph presents the relative percentage of $A\beta$ as compared to non-treated (NT) APP over-expressing cells (normalized to 100%=basal level of $A\beta$ secretion). chloroquine (chlor)=positive control for inhibition of $A\beta$ production. FIG. 1B shows the inhibition of production of intracellular $A\beta$. Cells were incubated in 6-well plates with 26 nM mAb for five days. Cells were then harvested, washed and resuspended in 70% formic acid, followed by sonication. This solution was centrifuged to remove insoluble material, and supernatant was collected. All such samples were analyzed for protein concentration by using Bradford reagent (Bio-Rad) and standardized for protein content before evaluation of $A\beta$ levels, which were quantified by a sandwich ELISA. In both FIGS. 1A and 1B, 100%–% produced=% inhibition, which increased with increasing mAb concentration.

FIG. 3B—$p<0.001$)).

In FIG. 7A, sAPPβ was detected using polyclonal antibody specific for the neoepitope generated after BACE cleavage in the spinal cords soluble fractions. The levels of sAPPβ were normalized to β-Actin levels. In FIG. 7B, detection of BACE1 in the spinal cord homogenates membrane fraction was performed using a specific anti C terminal MAb. Spinal cord BACE1 levels were normalized to β-Actin levels. All values are expressed as the mean±SEM. Statistical comparisons were performed using one-way ANOVA followed by Tukey-Kramer post hoc test. N(NT=4), N(G93A 80D)=4, N(G93A Final stage=3). *p<0.05; **p<0.01 (v.s. NT littermates).

In FIG. 8A, SOD1 was detected by polyclonal anti human SOD1 antibody and APP was detected using 22C11 antibody. In FIG. 8B, SOD1 levels were normalized to β-Actin levels. In FIG. 8C, APP levels were normalized to β-Actin. All values are expressed as the mean±SEM. Statistical comparisons were performed using Student's t-test. *p<0.05.

In FIG. 9A, SOD1 was detected by polyclonal anti human SOD1 antibody and APP was detected using 22C11 antibody. In FIG. 9B, SOD1 levels were normalized to β-Actin levels. In FIG. 9C, APP levels were normalized to β-Actin. All values are expressed as the mean±SEM. Statistical comparisons were performed using Student's t-test.

In FIG. 10A, sAPPβ was detected in spinal cord soluble fractions and normalized to β-Actin levels. In FIG. 10B, APP was detected in spinal cord membrane fractions and normalized to β-Actin. All values are expressed as the mean±SEM. Statistical comparisons were performed using Student's t-test. N(BBS)=4, N(Non relevant)=5. *p<0.05; **p<0.01 (v.s. Non relevant).

In FIG. 12A, GSK3β was detected by MAb and activated GSK3β by polyclonal anti-Tyrosine-216. Spinal cord GSK-3β levels and activated GSK3β levels were normalized to β-Actin levels. In FIG. 12B, p53 levels were detected using PAb 240 antibody and normalized to β-Actin. All values are expressed as the mean±SEM. Statistical comparisons were performed using Student's t-test. N(BBS)=4, N(Non relevant)=5. *p<0.05; **p<0.01 (v.s. Non relevant).

In FIG. 14A, immunohistochemistry and quantification of ChAT, a neuronal marker, in lumbar spinal cord of mice. In FIG. 14B, spinal cord sections were stained with anti-GFAP antibody, and the intensity of the staining was analyzed using Image-J Software. Scale bars in panels 14A and 14B correspond to 200 μm and 1 mm, respectively. Statistical comparisons were performed using Student's t-test. N(BBS)=5, N(Non relevant)=5. **p<0.01 (v.s. Non relevant).

DETAILED DESCRIPTION OF THE INVENTION

Figure 1A:
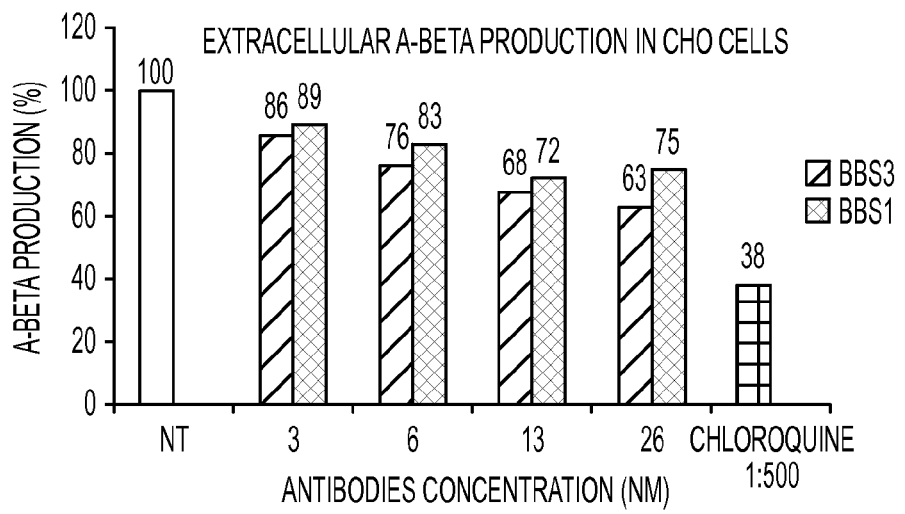
FIGS. 1A and 1B are graphs showing inhibition of $A\beta$ production by BBS mAbs in-vitro.

The present invention, in at least some embodiments, provides novel antibodies, and methods for use thereof and compositions thereof, optionally for treatment of a disease which is susceptible to amelioration by blocking cleavage of APP by BACE.

Novel Antibodies

The novel Abs provided according to at least some embodiments of the present invention are described with regard to Example 1 below, including the sequences.

The term "antibody" as used herein refers to an Ig molecule or immunologically active portion thereof that is readily derived by means of known techniques of protein chemistry and recombinant DNA engineering, i.e., antigen-binding portion. Non-limiting examples of immunologically active portions of Ig molecules include F(ab) and F(ab')$_2$ fragments, which retain the ability to bind APP. Such fragments can be obtained commercially or by using methods known in the art. For example F(ab)$_2$ fragments can be generated by treating the antibody with a protease such as pepsin, which produces one F(ab)$_2$ fragment and numerous small peptides of the Fc portion. The resulting F(ab)$_2$ fragment is composed of two disulfide-connected Fab units. The Fc fragment is extensively degraded and can be separated from the F(ab)$_2$ by dialysis, gel filtration or ion exchange chromatography. F(ab) fragments can be generated using papain, a non-specific endopeptidase that digests IgG molecules in the presence of reducing agent into three fragments of similar size: one Fc and two Fab fragments. When Fc fragments are of interest, papain is the enzyme of choice because it yields a 50 kilodalton Fc fragment; to isolate F(ab) fragments, the Fc fragments can be removed, e.g., by affinity purification using protein A/G. A number of kits are available commercially for generating F(ab) fragments, including the ImmunoPure IgG1 Fab and F(ab')$_2$ Preparation Kit (Pierce Biotechnology, Rockford, Ill.). In addition, commercially available services for generating antigen-binding fragments can be used, e g., Bio Express, West Lebanon, N.H.

The Aβ may optionally be polyclonal, monoclonal, recombinant, e.g., de-humanized, human, non-human, single-chain, or optionally one of this group as a de-immunized mAb, and optionally one or more of this group (e.g., humanized and de-immunized) as one chain in a bispecific mAb.

In some embodiments, the Aβ has effector function and can fix complement. In some embodiments, the Aβ has reduced or no ability to bind an Fc receptor. For example, the Ab can be an isotype or subtype, fragment or other mutant, which does not support binding to an Fc receptor, e.g., having a mutagenized or deleted Fc receptor binding region, including unglycosylated/deglycosylated/aglycosylated Fc (e.g., IgG1) or amino acid alterations in this region (Smith et al, 1998; Xu et al, 2000). The asparagine 297 residue being unglycosylated in the Fc region of IgG1 is particularly useful in reduced binding to the Fc receptor (Bolt et al, 1993). The Aβ can be coupled to a toxin or imaging agent.

Methods for making such Abs are also known; a non-limiting exemplary description is provided below with regard to Example 1.

Humanized antibodies are known in the art. "Humanization" results in a less immunogenic Aβ to humans that completely retains the antigen-binding properties of the original molecule (e.g., Queen et al, U.S. Pat. No. 5,585,089; Riechmann et al, 1988), which are incorporated herein by reference in their entirety. Abs can be humanized using a variety of techniques known in the art including, for example, chimeric antibody and CDR-grafting. In order to retain all such antigen-binding properties, the structure of its combining-site must be faithfully reproduced in the "humanized" version. This can be achieved potentially by transplanting the combining site of the nonhuman Aβ onto a human V region FR, either (a) by grafting the entire nonhuman V domains onto human C regions to generate a chimeric antibody (Morrison et al, 1984; Morrison and Oi, 1988 which preserves the ligand-binding properties, but which also retains the immunogenicity of the nonhuman V domains); (b) by grafting only the nonhuman CDRs onto human FR and C regions with or without retention of critical FR residues (Jones et al, 1986; Verhoeyen et al., 1988); or (c) by transplanting the entire nonhuman V domains (to preserve ligand-binding properties) but also "cloaking" them with a human-like surface through judicious replacement of exposed residues (to reduce immunogenicity) (Padlan, 1991).

De-immunized Abs are known in the art. "De-immunization" results from removal of T-cell epitopes from the mAb amino acid sequence, with the result that the mAb is less inherently immunogenic or non-immunogenic. This type of mAb engineering recognizes that for a mAb to function as an immunogenic antigen, the mAb sequence needs to encode a T-cell epitope for enabling T-cell help in order to elicit an antibody response against the mAb. This can potentially be achieved by screening the sequence using iTope™ or similar technology for in silico analysis of peptide binding to human MHC class II alleles (Perry et al., 2008) and using the TCED™ of known antibody sequence-related T-cell epitopes (Bryson et al., 2010), then making conservative amino acid changes that retain the secondary and tertiary structure of the mAb while eliminating such T-cell epitopes.

Composite Human Antibody™ technology produces humanized Abs without T-cell epitopes (EP1844074 and related filings). The antibody can also be a single-chain antibody. A single-chain antibody (scFV) can be engineered (Colcher et al, 1999; Reiter, 1996). Single-chain Abs can be dimerized or multimerized to generate multivalent Abs having specificities for different epitopes of the same target protein. In some embodiments, the Aβ is monovalent (Abbs et al., 1994), incorporated herein by reference.

In one embodiment, the present invention relates to an immune molecule which is capable of blocking APP cleavage by BACE, of which non-limiting examples are Abs, e.g., mAbs, or isolated mAb fragments, or antigen-binding portions or fragments thereof, with an affinity $(KD) \leq 10^{-7}M$ for the Fab fragment.

While KD describes the binding characteristics of an epitope and Ab, "potency" describes the effectiveness of the Aβ itself. A relatively low KD does not automatically mean a high potency. Thus, Abs can have relatively low KD and high potency (e.g., they bind well and alter the function strongly), relatively high KD and high potency (e.g., they don't bind well but have a strong impact on function), relatively low KD and low potency (e.g., they bind well, but not in a manner effective to alter a particular function) or relatively high KD and low potency (e.g., they do not bind well to the target and do not have a strong impact on function). In one embodiment, high potency means that there is a high level of inhibition with a low concentration of Ab. In one embodiment, an Aβ is potent or has high potency when its $IC_{50}$ is small, e.g., 130-110, 110-90, 90-60, 60-30, 30-20, 20-15, or less pM.

The term "selectively binds" in reference to Aβ does not mean that the Aβ binds only to a single molecule, but denotes that the KD to a first molecule is less than KD to a second molecule. Abs that bind exclusively to an epitope only bind to that one epitope.

According to another embodiment of the present invention, there is provided an isolated Ab, e.g., mAbs or isolated mAb fragments or antigen-binding portions or fragments thereof obtainable by the above-described process and wherein said isolated Aβ binds to human and/or mouse APP with $KD \leq 10^{-7}M$ for the Fab fragment. In some embodiments, an Aβ or fragment or antigen-binding portion thereof as disclosed herein specifically binds with a high affinity to APP.

As used herein, "specific binding" refers to Aβ binding to a predetermined antigen. Typically, the Aβ binds with $KD \leq 10^{-6}$ M for the Fab fragment, and binds to the predetermined antigen with a KD at least ten-fold less than its KD for binding to a non-specific antigen (e.g., BSA, casein) other than the predetermined antigen or closely-related antigen. The phrases "an antibody recognizing an antigen" and "an antibody specific for an antigen" are used interchangeably herein with the term "an antibody which binds specifically to an antigen".

The term "Kassoc" or "Ka", as used herein, is intended to refer to the association rate of a particular antibody-antigen interaction, whereas the term "KdiS" or "Kd" is intended to refer to the dissociation rate of a particular antibody-antigen interaction. The term "high affinity" for an IgG refers to a Kd for the Fab fragment of at least $\sim 10^{-6}M$, at least $\sim 10^{-7}M$, at least $\sim 10^{-8}M$, at least $\sim 10^{-9}M$, at least $\sim 10^{-10}M$, at least $\sim 10^{-11}M$, or at least $\sim 10^{-12}M$ or greater, e. g., up to $10^{-13}M$ or $10^{-14}M$ or greater. However, "high affinity" binding can vary for other antibody isotypes.

Dosage, toxicity and efficacy of such Aβ compositions can be determined by standard procedures in cell cultures (e.g., cells taken from an animal after administration of an Ab) or experimental animals, e.g., for determining $LD_{50}$ (the dose lethal to 50% of the study group) and $ED_{50}$ (the dose therapeutically effective in 50% of the study group). The dose ratio between toxic and therapeutic effects is the therapeutic index, which can be expressed as the ratio $LD_{50}/ED_{50}$. Compositions exhibiting high therapeutic indices are preferred for clinical development. While Aβ compositions that exhibit toxic side effects may be used, care should be taken to design a delivery system that targets such compounds to the site of affected tissue in order to minimize potential damage and thereby reduce side effects.

Data obtained from cell cultures (cells from an animal after Aβ administration) and animal studies can be used in formulating a range of dosage levels for human use. The dosage of Aβ compositions lies preferably within a range of therapeutically available concentrations including $ED_{50}$ with little or no toxicity. The dosage may vary within this range depending upon the dosage form employed and the route of administration utilized. For any Aβ compositions used in the methods described herein, the therapeutically effective dose can be estimated initially from assays of cell cultures. A dose also may be formulated in animal studies based on efficacy in suitable animal models. Such information can be used to more accurately determine useful doses in humans.

As defined herein, a therapeutically effective amount of Aβ (i.e., effective dosage) depends on the selected b, mode of delivery, and the condition to be treated. For instance, single dose amounts of Aβ in the range of about 0.1-100 mg/kg may be administered; in some embodiments, about 0.1, 1, 5, 10, 20, or 50 mg/kg may be administered. In some embodiments, e.g., pediatric subjects, a lower amount of Aβ is administered given their low body weight. The Ab compositions can be administered from one or more times per week or month or year, including for example once every week or month. The compositions can be administered, e.g., once every 14-30 days or longer. The skilled artisan will appreciate that certain factors may influence the dosage and timing required to effectively treat a subject, including but not limited to the severity of the disease or disorder, type of disease or disorder, previous treatments, the general health and/or age of the subject, other diseases present, and persistence of the therapeutic effect.

Moreover, treatment of a subject with a therapeutically effective Aβ amount may optionally include a single treatment or may optionally include a series of treatments.

Pharmaceutical Compositions

The pharmaceutical composition can be included in a container, pack, or dispenser together with instructions for administration.

Pharmaceutical compositions suitable for injection are typically buffered liquid formulations, or lyophilized dry formulations.

Solid dosage forms are desirable for ease of determining and administering defined dosage of active ingredient and ease of administration.

Liquid dosage forms also allow subjects to easily take the required dose of active ingredient; liquid preparations can be prepared as a drink, or to be administered, for example, by a naso-gastric tube.

Liquid oral compositions generally require a suitable solvent or carrier system in which to dissolve or disperse the active agent, thus enabling administration to a subject. A suitable solvent system is compatible with the active agent and non-toxic to the subject. Typically, liquid oral formulations use a water-based solvent.

Oral compositions can optionally be formulated to reduce or avoid degradation, decomposition, or deactivation of the active agent by the gastrointestinal system, e.g., by gastric fluid. For example, compositions can optionally be formulated to pass through the stomach unaltered and to dissolve in the intestines, i.e., as enteric-coated compositions.

One of ordinary skill in the art would readily appreciate that these pharmaceutical compositions can be prepared by applying known manufacturing procedures as established through a long history of application for oral products. Such formulations can be administered to a subject with methods well-known in the pharmaceutical arts. Thus, the practice of the present methods will employ, unless otherwise indicated, conventional techniques of pharmaceutical sciences including pharmaceutical dosage form design, drug development, pharmacology, and organic chemistry, including polymer chemistry. Accordingly, these techniques are within the capabilities of one of ordinary skill in the art and are explained fully in the literature (see, e.g., Remington, The Science and Practice of Pharmacy, Nineteenth Edition. Alfonso Gennaro (Ed.): Mack Publishing Co., Easton Pa., 1995, hereinafter Remington, incorporated by reference herein in its entirety).

Methods of Treatment

According to various embodiments of the present invention, the immune molecule compositions described herein can be administered to a subject to treat (which as described previously also includes preventing progression and/or delaying development of) a disease susceptible to treatment by blocking cleavage of APP.

In some embodiments, the Aβ compositions are administered concurrently with one or more second therapeutic modalities as described herein.

EXAMPLES

Having now generally described the invention, the same will be more readily understood through reference to the following examples which are provided by way of illustration and are not intended to be limiting of the present invention.

Example 1

Derivation of Novel BBS Antibodies

New BBS Abs, including an Aβ termed herein "BBS3", were discovered according to the method set forth herein. "BBS" means Abs capable of blocking cleavage of APP by BACE, optionally by recognizing and blocking the cleavage site on APP. New BBS mAbs were obtained following immunization of mice with multiple antigenic peptide (MAP) of the same peptide used to derive BBS1 (MAP1-IP, immunizing peptide: ISEVKLDA x8, SEQ ID NO:15) or with the related MAP2-IP (ISEVKLDAKLDA x8, SEQ ID NO:16). BBS1 is a specific example of an mAb raised against the APP cleavage site, which blocks BACE cleavage of APP. BBS1 mAb was disclosed in U.S. Pat. No. 7,494,655, hereby incorporated by reference as if fully set forth herein. Briefly, this Aβ was raised against the MAP1-IP peptide spanning the cleavage site with a sequence known as the "half-Swedish mutation" (ISEVKLDA, SEQ ID NO:15 of the present application).

BALB/c mice were immunized 4× at 14-day intervals as follows: four mice were immunized with MAP1-IP, and three mice were immunized with MAP2-IP. Serum samples of immunized mice were tested by ELISA vs. IP, WT (wild type=ISEVKMDA x8, SEQ ID NO:18), SW (double Swedish mutation=ISEVNLDA x8, SEQ ID NO:17), and negative control peptide. The two mice with the highest IP & WT ELISA titers were chosen; one was further immunized with MAP1 (#4) and the other further with MAP2 (#5). Spleens were fused to NS0 cells to create hybridomas, and were screened by ELISA vs. WT. After several cycles of limiting dilution cloning of positive subclones, five final mAbs, designated F5.100 and F5.87 (IgG1), F4.10 and F4.17 (IgG2a), and F5.69 (IgG2b), were produced.

Example 2

Sequence by PCR of cDNA Encoding Novel BBS Antibodies mRNA was extracted from the hybridoma cell pellets of F5.100 by a standard extraction protocol. cDNA was created from the RNA by reverse transcription with oligo(dT) primer. PCR reactions employed known V and C domain primers to amplify the VH, VL, CH and CL regions of the mAb DNA, giving the expected size bands. VH, VL, CH and CL bands were extracted and gel purified. Purified PCR products were cloned into the Invitrogen sequencing vector pCR2.1 and transformed into TOP10. Selected colonies were picked and analyzed through sequencing. Consensus nucleotide sequence and deduced amino acid sequence of clone F5.100 were obtained and are as follows:

F5.100 H Chain nucleotide sequence (SEQ ID NO:1);
F5.100 H Chain amino acid sequence (SEQ ID NO:2);
F5.100 L Chain nucleotide sequence (SEQ ID NO:3); and
F5.100 L Chain amino acid sequence (SEQ ID NO:4);

The F5.100 VH and VL regions, termed herein BBS3 mAb or F5.100 mAb V regions, were re-sequenced as follows. Hybridoma cells expressing BBS3 mAb were grown in culture, cells were pelleted by centrifugation, and RNA was extracted from the hybridoma cell pellet using an RNAqueous-4PCR kit (Ambion cat. #AM1914). V regions were amplified using RT-PCR using degenerate primer pools for murine signal sequences together with C region primers for each of IgG VH, Igκ VL and Igλ VL. H-chain V-region RNA was amplified using a set of six degenerate primer pools (HA to HF), and L-chain V-region mRNA was amplified using a set of eight degenerate primer pools, seven for the κ cluster (KA to KG) and one for the λ cluster (LA). PCR products were purified and cloned into a cloning vector (pGEM-T Easy, Promega cat.#A1360) and transformed into bacterial cells. Selected colonies were picked and sequenced, 12 corresponding to the H-chain PCR product and 12 corresponding to the L-chain PCR product.

The results of the sequencing of the 12 VH and 12 VL colonies along with the derived amino acid sequences are presented below.

VH nucleotide sequence (SEQ ID NO:5) with 100% consensus among the 12 clones;
VH amino acid sequence of F5.100 as shown below, was deduced from SEQ ID NO:5, with the CDR sequences shown underlined, as determined by the Kabat numbering system:

```
                                          (SEQ ID NO: 6)
EVQLQQSGPELVKPGASVKISCKASGYTFTDYNMHWVKQSHGKRLEWIGY

IYPHNGGTGYNQRFKSKATLTVDKSSSTAYMELRSLTSEDSAVYYCARPG

TEAYWGQGTLVTVSA.
```

VL nucleotide sequence (SEQ ID NO:7) with 100% consensus among the 12 clones; and VL amino acid sequence of F5.100, as shown below, was deduced from SEQ ID NO:7, with the CDR sequences shown underlined as determined by the Kabat numbering system:

(SEQ ID NO: 8)
DIVMTQSQKFMSTSVGDRVSVTC<u>KASQNVGTNVA</u>WYQQKPGQSPKPLIY<u>S

ASYRYS</u>GVPDRFTGSGSGTDFTLTISNVQSEDLAEYFC<u>QQFNSYPLT</u>FGA

GTKLELK.

Table 1 below shows SEQ ID NOs: 9-14 derived from F5.100, which are CDRs (CDR1, CDR2 and CDR3) according to at least some embodiments of the present invention.

TABLE 1

|    | CDR1                   | CDR2                             | CDR3                      |
|----|------------------------|----------------------------------|---------------------------|
| VH | DYNMH<br>(SEQ ID NO: 9) | YIYPHNGGTGYNQRFKS<br>(SEQ ID NO: 10) | PGTEAY<br>(SEQ ID NO: 11) |
| VL | KASQNVGTNVA<br>(SEQ ID NO: 12) | SASYRYS<br>(SEQ ID NO: 13) | QQFNSYPLT<br>(SEQ ID NO: 14) |

The nucleotide and amino acid sequences of the H and L chains, and the VH and VL regions of a different BBS mAb, the F5.87 mAb, were obtained in a manner similar to that used for the H and L chains and the VH and VL regions of F5.100 MAb, as described above.

The H chain amino acid sequence of F5.87 (SEQ ID NO:52 encoded by the nucleotide sequence SEQ ID NO:53) and the VH region amino acid sequence of F5.87 (SEQ ID NO:26), shown below with CDR sequences shown underlined as determined by the Kabat numbering system, was derived from its nucleotide sequence:

(SEQ ID NO: 26)
EVKLEESGGGLVQPGGSMKLSCAASGFTFS<u>NAWMD</u>WVRQSPEKGLEWVAE

<u>IRSKANNHATYYGESVKG</u>RFTISRDDSKSSVYLQMNSLRAEDTGIYYCTA

<u>TVRGGY</u>WGQGTTLTVSS.

The L chain amino acid sequence of F5.87 (SEQ ID NO:54 encoded by the nucleotide sequence SEQ ID NO:55) and the VL region amino acid sequence of F5.87 (SEQ ID NO:27), shown below with the CDR sequences shown underlined as determined by the Kabat numbering system, was derived from its nucleotide sequence:

(SEQ ID NO: 27)
DIKMTQSPSSMYASLGERVTITC<u>KASQDINSYLS</u>WFQQKPGKSPKTLIY<u>R

ANRLVD</u>GVPSRFSGSGSGQDYSLTISSLEYEDMGIYYC<u>LQYDEYPYT</u>FGG

GTKLEIK.

Table 2 below shows SEQ ID NOs: 28-33 derived from F5.87, which are CDRs (CDR1, CDR2 and CDR3) according to at least some embodiments of the present invention.

TABLE 2

|    | CDR1                    | CDR2                               | CDR3                        |
|----|-------------------------|------------------------------------|-----------------------------|
| VH | NAWMD<br>(SEQ ID NO: 28) | EIRSKANNHA<br>TYYGESVKG<br>(SEQ ID NO: 29) | TVRGGY<br>(SEQ ID NO: 30) |
| VL | KASQDINSYLS<br>(SEQ ID NO: 31) | RANRLVD<br>(SEQ ID NO: 32) | LQYDEYPYT<br>(SEQ ID NO: 33) |

In some embodiments, an Aβ fragment useful in the compositions and methods as disclosed herein comprises at least one or any combination of CDRs from the same Ab. In some embodiments, an Aβ fragment useful in the compositions and methods as disclosed herein is a functional fragment, and comprises at least one or two or more CDRs as disclosed in Table 1 or 2. In some embodiments, an Aβ fragment for use in the methods and compositions as disclosed herein comprises at least 3 consecutive amino acids from any of the CDR regions selected from any or a combination of CDRs listed in Table 1 or 2, e.g., SEQ ID NOs:9-14 and 28-33. In some embodiments, an Aβ fragment useful in the compositions and methods as disclosed herein comprises at least one or any combination of CDRs from the same Ab Example 3

Sequence of N-Terminus of Novel BBS Monoclonal Antibody

The N-terminal sequence of BBS3 mAb clone F5.100 was determined as follows.
a. Edman Degradation
The N-terminal sequences of the H and L chains were determined using Edman degradation (Edman el al, 1950). BBS3 MAb is subjected to SDS-PAGE then transferred and blotted to a PVDF membrane stained in Coomassie 8250. Automated Edman degradation microsequencing is accomplished on Procise 490 Protein Sequencer (ABI). Phenylisothiocyanate is reacted with an uncharged N-terminal amino group under mildly alkaline conditions to form a cleavable amino acid derivative. After consecutive transformations, the more stable phenylthiohydantoin (PTH) amino acid derivative is formed, which can be identified by chromatography or electrophoresis. The procedure is repeated to identify the next amino acid.

Several methods for removing N-terminal blocking groups have been reported.
  i. Formyl group removal—Incubating a stained protein band on a PVDF-type membrane with 0.6 N HCl at 25° C. for 24 h is reported to remove formyl groups from N-terminal amino acids.
  ii. N-terminal acetylserine or acetylthreonine removal—Incubation at 45° C. with trifluoroacetic acid followed by drying and subsequent 16 h incubation at 60-65° C. removes N-terminal acetylserine or acetylthreonine from proteins adsorbed to a glass fiber filter or electroblotted onto ProBlott PVDF membrane. Some cleavage of internal serines and threonines may occur.
  iii. N-terminal pyroglutamic acid removal—Pyroglutamate aminopeptidase (Boehringer-Mannheim catalog#1420-445) removes N-terminal pyroglutamic acid from proteins bound to PVDF membrane or adsorbed to GF filters.
  iv. Acetylated N-terminal amino acid removal—Acylamino acid releasing enzyme (Boehringer Mannheim catalog #1370502) removes acetylated N-terminal amino acids from peptide fragments recovered in solution from in situ trypsin digestion.

b. N-Terminus Labeling (Reductive Dimethylation)

The protein sample in 8M Urea and 50 mM HEPES, pH8 was incubated with 20 mM formaldehyde and 10 mM NaCBH$_3$ (60° C., 15 min), then neutralized with Ammonium bicarbonate. The process was continued as described below in Example 4 for MALDI analysis.

c. H Chain N-Terminal Sequencing

The first amino acid was identified by MALDI as peptide V20 using reductive dimethylation and by Edman degradation, which identified E19 with the sequence EVQLQ (SEQ ID NO:19).

| Peptide | MH+ | DeltaM (ppm) | z | Type | Pep |
|---|---|---|---|---|---|
| #VQLQQSGPELVKAP GASVK (SEQ ID NO: 20) | 2050.15428 | -1.99351 | 2 | CID | 3.02E-09 |

\# N-terminus of the protein labeled with dimethylation.
K^ Lys labeled with dimethylation d. L Chain N-Terminal Sequencing The first amino acid was identified by MALDI as peptide D21 and part of the molecules was G20, N-Terminal by Edman degradation identified D21, peptide DIVMT (SEQ ID NO:23).

| Peptide | MH+ | DeltaM (ppm) | z | Type | Pep |
|---|---|---|---|---|---|
| #DIVM*TQSQK^FMST SVGDR (SEQ ID NO: 21) | 2102.02565 | -3.65050 | 3 | CID | 4.34E-07 |
| #DIVMTQSQK^FMSTS VGDR (SEQ ID NO: 21) | 2086.03074 | -1.95491 | 2 | CID | 3.77E-14 |
| #GDIVMTQSQK^FMST SVGDR (SEQ ID NO: 22) | 2143.05220 | -2.52610 | 3 | CID | 5.86E-03 |

\# N-terminus of the protein labeled with dimethylation.
K^ Lys labeled with dimethylation
M* Oxidized Met Based on Predisi (www.predisi.de) analysis of the signal peptide cleavage site, the predicted H-chain N-terminal sequence is EVQLQ (E=amino acid #20, SEQ ID NO:19), and the predicted L-chain sequence is DIVMT (D=amino acid #21, SEQ ID NO:23). Both sequences confirm the Edman degradation sequence.

Thus, the N-termini sequences of BBS3 H and L chains begin with DIVMT (SEQ ID NO:23) and EVQLQ (SEQ ID NO:19), respectively, which agrees with the Edman degradation data. The results also agree with the in-silico signal cleavage prediction done using Predisi. Thus, the data for the N-termini of the H and L chains are confirmed to have the above-described sequences.

Example 4

Sequence of Novel BBS Monoclonal Antibody Based on Peptide Sizing

Confirmatory sequencing was done by comparing the peptide sequence derived from Mass Spectroscopy (MS) of reversed-phase high performance liquid chromatography (RP-HPLC)-separated peptides (LC-MS) to the BBS3 mAb amino acid sequence derived from cDNA sequencing (Example 2). The protein masses in each sample were determined using a MALDI-TOF MS device (MicroMX, Waters) in linear mode. The protein sample in 8M Urea and 100 mM Ammonium bicarbonate was reduced with 2.8 mM DTT (60° C., 30 min), modified with 9.4 mM iodoacetamide in 100 mM ammonium bicarbonate (25° C., 30 min in the dark), and digested at 1:50 enzyme:substrate ratio in 2M urea 25 mM ammonium bicarbonate with i. modified chymotrypsin or ii. trypsin overnight at 37° C., or iii. with Glu-C at 25° C. Resulting peptides were resolved by RP-HPLC on 0.075×200-mm fused silica capillaries (J&W) packed with Reprosil RP material (Maisch GmbH, Germany). Peptides were eluted with a linear 60-min gradient of 5-45% acetonitrile and 15-min gradient at 95% acetonitrile with 0.1% formic acid in water at flow rates of 0.25 µL/min. On-line MS was performed by an ion-trap MS device (Orbitrap, Thermo) in positive mode using repetitively full MS scan followed by collision induces dissociation (CID) of the 7 most dominant ion selected from the first MS scan. MS data are analyzed using Sequest 3.31 software (Eng and Yates, U. Washington and Finnigan, San Jose) relative to the BBS3 mAb sequence derived according to Example 2.

These peptide sizing data presented as SEQ ID NO:24 for the H chain sequence and as SEQ ID NO:25 for the L chain sequence were found to have 100% match of residues 9 to 112 of SEQ ID NO:24 and of residues 7 to 108 of SEQ ID NO:25 to the amino acid sequence of the BBS3(F5.100) VH and VL chains, respectively, as shown below in bold letters, which includes 100% coverage of the CDRs that are underlined. The MALDI sequence was composed by the software and covers the molecule except for amino acids that were not found (strikethrough). All amino acids in CDRs were verified except the Phe (F, position 83) in H-chain CDR2 (residue 15 of SEQ ID NO:10); however, this F in CDR2 is found almost exclusively in all Aβ genes derived from the same germ-line gene family, and thus is credible. The N-terminal sequence by two methods (MALDI labeling and Edman degradation (Example 3) define the two N-termini (residues 4 and 5 of SEQ ID NO:24 and residues 1 and 2 of SEQ ID NO:25) in small letters as follows.

H chain sequence
(SEQ ID NO: 24)
~~MGRSWIFLFLLSGTAG~~VHSevQLQQSGPELVKPGASVKISCKASGYTFT DYNMHWVKQ̶S̶H̶G̶KRLEWIG<u>YIYPHNGGTGYNQR</u>F̶KSKATLTVDKSSST AYMELRSLTSEDSAVYYCAR<u>PGTEAY</u>WGQGTLVTVSAAKTTPPSVYPLAP

GSAAQTNSMVTLGCLVKGYFPEPVTVTWNSGSLSSGVHTFPAVLQ

~~SDLYTLSSS~~VTVPSSTW

PSETVTCNVAHPASSTKVDKKIVPRDCGCKPCICTVPEVSSVFIFPPKPK

DVLTITLTPKVTCVVVDISKDDPEVQFSWFVDDVEVHTAQTQPR

~~EEQFNSTF~~RSVSELPIMHQDWLNGKEFKCRVNSAAFPAPIEKTISKTK

GRPKAPQVYTIPPPKEQMAKDKVSL~~FCMITDFFPEDITVEW~~QWNGQ

PAENYKNTQPIMDTDGSYFVYSKLNVQKSNWEAGNTFTCSVLHE

~~LHNHHTEKSLSHSPGK~~

-continued

L chain sequence (SEQ ID NO: 25)

MESQTQVFVYMLLWLSGVDgdIVMTQSQKFMSTSVGDRVSVTC<u>KASQN</u>

<u>VGTNVA</u>WYQQKPGQSPKPLIY<u>SASYRYS</u>GVPDRFTGSGSGTDFTLTISN

VQSEDLAEYFC<u>QQFNSYPLT</u>FGAGTKLELKRADAAPTVSIFPPSSEQLT

SGGASVVCFLNNFYPKDINVKWKIDGSERQNGVLNSWTDQDSKDSTYSM

SSTLTLTKDEYERHNSYTCEATHKTSTSPIVKSFNRNEC

Example 5

Affinity of BBS mAbs

The affinity of new MAbs was assessed by BIAcore. Protein G was immobilized on the CM5 chip as capturing molecule for the different mAbs. Each mAb (ligand) was bound separately to Protein G, and different APP MAP peptides were added separately to the liquid phase (analytes) at different concentrations to test the affinity of the mAb to each peptide. Each mAb was tested for its affinity to the different APP MAP peptides for aa 666-673 WT (wild type=ISEVKMDA, SEQ ID NO:18), IP (immunizing peptide=ISEVKLDA, SEQ ID NO:15), and SW (ISEVN-LDA, SEQ ID NO:17). The chip was regenerated by HCl after each cycle of mAb-peptide.

Results show that the new mAbs have nM-range affinities for target APP peptide, which is 1000-fold improvement in affinity for WT over that of BBS1 (Table 3). New lead BBS3 mAb (F5.100) is more active for inhibiting the Aβ production from CHO cells (Example 6).

TABLE 3

Affinity (KD) of mAb to APP peptide

| mAb | Isotype | APP peptide | | |
|---|---|---|---|---|
| | | WT | IP | SW |
| BBS1 | IgG1 | $2.2 \times 10^{-6}$ | $9.2 \times 10^{-8}$ | $1.0 \times 10^{-7}$ |
| F5.100 (BBS3) | IgG1 | $1.5 \times 10^{-9}$ | $3.8 \times 10^{-9}$ | $8.8 \times 10^{-9}$ |
| F5.87 | IgG1 | $3.3 \times 10^{-9}$ | $1.2 \times 10^{-9}$ | $1.1 \times 10^{-9}$ |

The ~1000-fold improvement in affinity of BBS3 (F5.100) and F5.87 MAbs over BBS1 MAb was unexpected based on the immunization regimens, such that the derivation of this higher affinity BBS3 MAb was quite surprising.

These mAbs are optionally and preferably assessed biologically as described in greater detail below. A description is provided with regard to testing of BBS3 mAb for the purpose of illustration only and without any intention of being limiting.

Example 6

Activity of BBS1 and BBS3 mAbs in Cell Culture

Figure 1B:
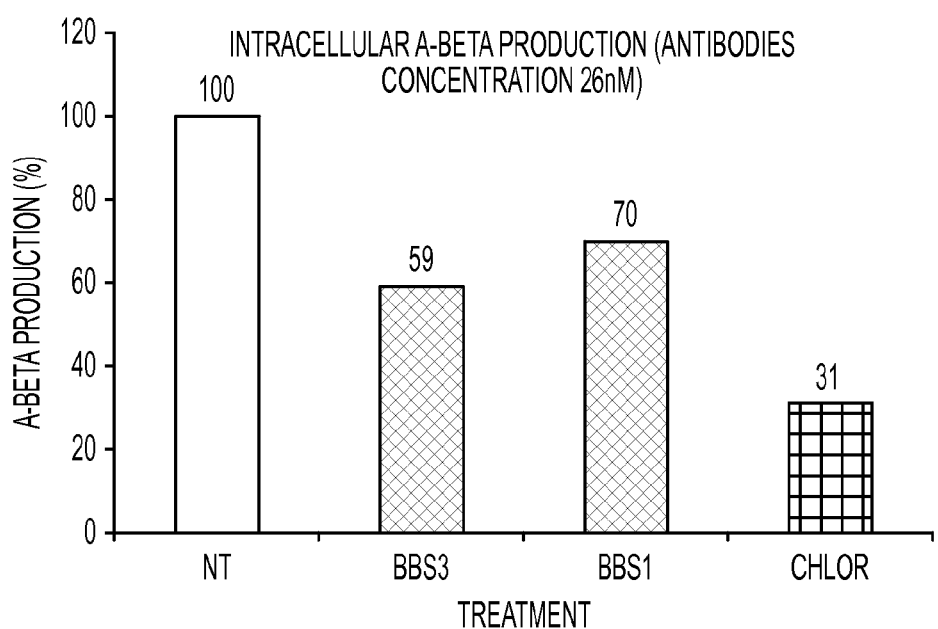

Biological activity of the purified BBS mAbs was tested in a cell-based bioassay. The assay quantifies the percent inhibition of Aβ production in APP over-expresser CHO cells by evaluating intra- and extra-cellular levels of Aβ following incubation of cells with different mAb concentrations. The data (FIGS. 1A and 1B) show that BBS3 mAb can inhibit intracellular and extracellular Aβ production to a greater degree than BBS1 mAb.

Example 7

Immunotherapy with BBS3 mAb in Tgx3 Mice

The ability of BBS3 mAb vs. isotype-matched control mAb to cause favorable AD-related changes in vivo was assessed in Tgx3 mice by ICV (intracerebroventricular) continuous flow injection of mAb with an implanted osmotic pump for 6 weeks. This triple transgenic model of AD (Tgx3), with neuron-specific expression of clinical mutants of human APP (Swedish), PS1 and Tau, shows spontaneous, progressive accumulation of Aβ in brain, eventually resulting in amyloid plaques and intracellular tangles. Onset of pathology is at 3 months of age, with amyloid plaques, abnormal Tau pathology and cognitive deficits without neuron loss and vascular pathology.

Materials and Methods

MAbs were mixed before injection with artificial Cerebral Fluid (Iwata et al., 2000).

Tgx3 AD (LaFerla FM, USA) 15-month-old mice are used as the animal model. C57BL6 mice were used as non-transgenic control mice for behavioral evaluations.

The following procedures were performed on weeks specified with X (Table 4).

TABLE 4 study schedule

| Week of study | −1 | 0 | 1 | 2 | 3 | 4 | 6 | 6.5 |
|---|---|---|---|---|---|---|---|---|
| Implantation | | X | | | | | | |
| Serum for analysis | X | | | | | | | X |
| Behavioral analysis* | | | | | | X | X | |
| Brain tissue for histopathology and biochemistry | | | | | | | | X |

*Also performed for C57BL/6 mice

A pump was implanted into the transgenic mice to dispense BBS3 or control mAb (P709). Blood samples were collected from the orbital sinus vein before the implant and at the end of the experiment from all mice. Serum was separated from blood and stored frozen for assays.

The implantation procedure for Alzet mini-osmotic pumps was carried out according to the previously described protocol (Dolev and Michaelson, 2004). Briefly, Alzet mini-osmotic pumps (model 2006, Alzet, Palo Alto, Calif.), which deliver liquid at 0.15 µL/hour for up to 42 days, were connected by a polyethylene catheter to a stainless steel cannula (Brain Infusion kit, Alzet). Pumps were loaded with a suitable dose of BBS3 mAb or control mAb in artificial CSF with 1 mM ascorbic acid (Iwata et al, 2000). Pumps were incubated in saline overnight at 37° C. Tgx3 mice were anesthetized by IP injection of ketamine/xylazine mixture (100 mg Ketamine and 20 mg Xylazine/kg body-weight), skulls were exposed, and a hole was drilled with a 25-gauge needle above the lateral ventricle (2 mm posterior and 2.5 mm lateral to the bregma). The tip of the brain infusion cannula was inserted into the hole, and the cannula was glued to the skull. The pump was inserted SC on the mouse's back, and the cut skin over the skull was sutured. An antibiotic (0.45 mg tetracycline/mouse in 37° C. 200 µl NaCl0.9%) was injected IP after the implant. Mice were kept for 42 days after the pumps were implanted, followed by weekly body weight determinations.

Behavioral analysis examined the beneficial effects of the treatment. Following 4 weeks, spatial memory was assessed by a Y-maze test, and non-spatial memory was tested 2 weeks later by an object recognition test.

The Y-maze is built of plastic and consisted of three arms (Dellu et al, 1992). Each arm is 8×30×15 cm in size, at an angle of 120° with respect to the other arms. Each arm is distinguished from the others by a different visual cue (triangle, square and non). The "non" arm is selected as the start arm, and the animal is placed twice in this arm. During the first trial lasting for 5 min, one of the other two arms is blocked (triangle), whereas for the second trial lasting for 2 min, both arms are open. The two trials are separated by a 2-min interval, during which the mouse is returned to its home cage. The time and frequency spent in each of the arms are measured.

After 6 weeks treatment, mice were subjected to 3 days of object recognition tests (Ennaceur & Delacour, 1988) with minor modification. On days −1 and −2, mice were placed individually for 10 min habituation in a 60×60×30 cm Plexiglas open field box with translucent floor dimly lit by an overhead lamp. During the habituation stage, Object A (black can) was placed in the open field box. On day −3, a recognition test was performed. Object B (transparent bottle) was placed in the open field box. The duration and frequency by which mice explore familiar Object A and novel Object B were recorded for 5 min. The recognition index (RI), defined as the ratio of the duration/frequency during which Object B was explored compared to the duration during which both Objects are explored, was used to measure non-spatial memory. Both chosen objects were of equal interest to transgenic C57BL mice as measured by exploration time.

After the Week 6 behavioral test, mice were anaesthetized and transcardially perfused with saline. Brain tissues were removed from the cranium. The right hemisphere was preserved for histology analysis in 4% paraformaldehyde in PBS, and the left hemisphere was immediately immersed in liquid nitrogen and stored at −70° C. until homogenization for biochemical assays.

Results

Figure 2A:
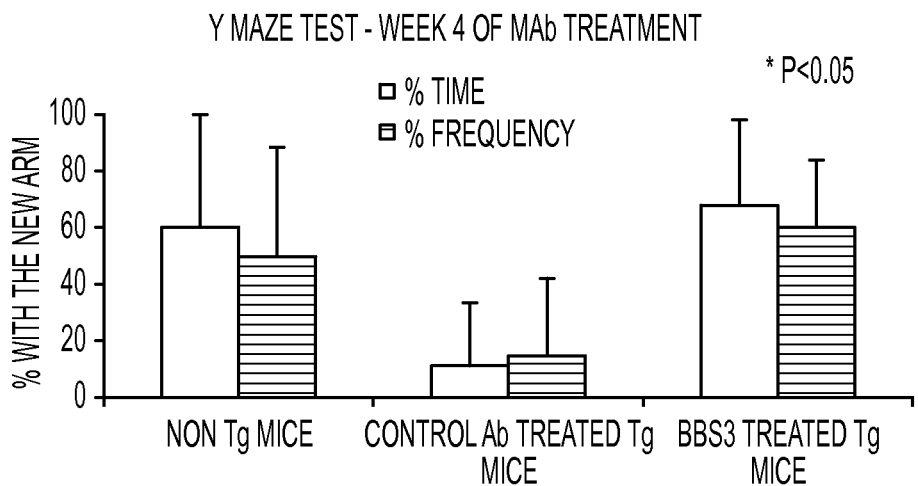
FIGS. 2A and 2B are graphs showing evaluation of memory in Tgx3 mice following BBS3 mAb treatment. BBS3 mAb was administered for 6 weeks to 15-month-old Tgx3 mice by intracerebroventricle (ICV) continuous flow with an implanted osmotic pump and compared to isotype-control mAb. The mAbs were loaded into the pump at a concentration of 1.5 µg/µL and pumped at a rate of 0.25 µL/hr, for a total dose of 9 µg/day. The effect of treatment on the memory of mice was assessed by a Y-maze test following 4 weeks of treatment (FIG. 2A); and an unrelated object recognition test following 6 weeks of treatment (FIG. 2B). C57BL/6 Non-Tg mice were used as positive control for the memory tests. *p—statistical significance by t-test of BBS3-treated Tg vs. Control $A\beta$ (P709, which is directed against a prokaryotic protein)-treated Tg mice. The plastic Y-maze consisted of three arms (Dellu et al. 1992), each being 8×30×15 cm in size and at an angle of 120° with respect to the other two arms. Each arm was distinguished from the others by a different visual cue (triangle, square and none). The "none" arm was selected as the starting arm, and the animal was placed twice in this arm. In the first trial, which lasted for 5 min, one of the other two arms was blocked (triangle), whereas for the second trial, which lasted for 2 min, both arms were open. The two trials were separated by a 2-min interval, during which the mouse was returned to its home cage. The time and frequency spent in each of the arms were measured. For the object recognition test, mice were placed in an open field box that contained one object (X) for 10 min of habituation for the first 2 days. On Day 3, Object X was replaced with a novel Object Y, and the mouse exploration times of the familiar Object X and the Novel object Y were recorded. The recognition indexes were calculated and presented as a % for the ratio between the exploration time/frequency of the novel object over the exploration time/frequency of the familiar and novel objects.
Figure 2B:
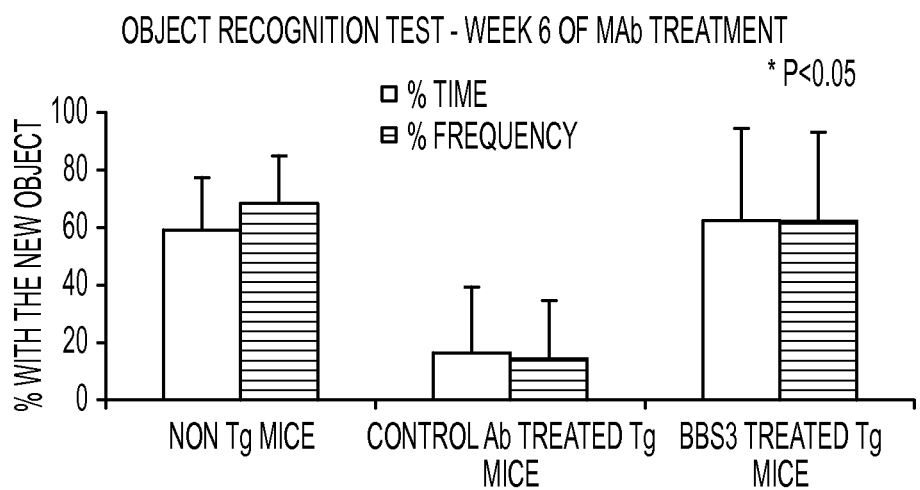

Cognitive functions following BBS3 mAb treatment were demonstrated using both the Y-maze test at week-4 and object recognition test at week-6. Mice treated with BBS3 mAb showed significantly improved memory compared to control-mAb-treated mice ($p<0.05$) in terms of time and frequency in both tests (FIGS. 2A and 2B). Moreover, the behavioral index of BBS3-treated Tgx3 mice was comparable to that of untreated non-Tg mice, thus showing full efficacy of BBS3 mAb in preventing AD-related behavioral disorders.

Figure 3A:
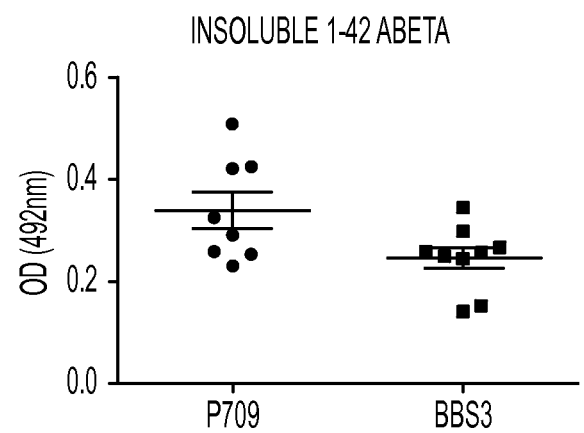
FIGS. 3A and 3B are graphs showing $A\beta$ (Abeta) levels in the insoluble fraction of Tgx3 mouse brain lysates following BBS3 treatment. Brain tissues from BBS3- or control-treated mice were homogenized and separated, following centrifugation, to the soluble extracellular-enriched protein fraction and the pellet. The pellet, which contains membrane-associated proteins, was extracted by repeat homogenization and centrifugation. The final supernatants were collected, and the insoluble material was incubated with 70% formic acid, mechanically dissociated with a micropipette, gently agitated, and titrated with 1M Tris-HCl, pH 8. Samples were centrifuged, and supernatants were collected and stored frozen for analysis. The insoluble fraction was tested by sandwich ELISA to quantify insoluble $A\beta 1$-42 (FIG. 3A) and total insoluble $A\beta$ (FIG. 3B). P709—isotype-control control mAb, p—statistical significance by t-test (FIG. 3A—$p<0.05$.
Figure 3B:
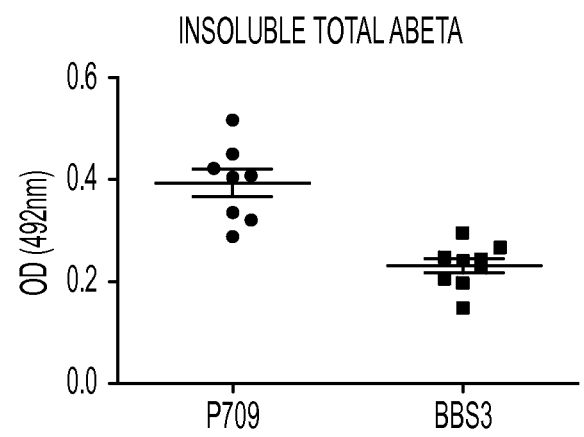
Figure 4A:
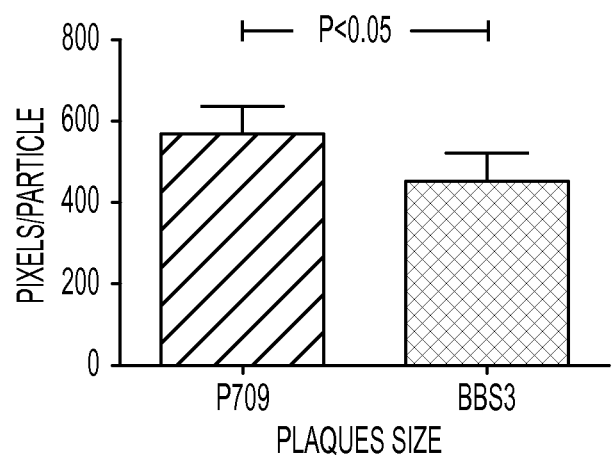
FIGS. 4A and 4B are groups showing histological evaluation of brain $A\beta$ plaques level in Tgx3 mice following BBS3 treatment. Frozen brain sections from the mid-sagittal line were sliced to 15 µm slices and stained in a floating technique. Modified thioflavin-S staining of dense core plaques in the subiculum is shown in FIG. 4A. Brain sections were stained with 0.01% Thio-S in 50% ethanol. Immunostaining with 4G8 antibody is shown in FIG. 4B. Sections were hydrated and treated with 0.3% $H_2O_2$ in PBS in order to block endogenous peroxidase activity. Non-specific binding sites were blocked by treatment with Ultra V block (Labvision, USA) and 10% goat serum in 3% BSA. Biotinylated Aβ antibody 4G8 (Covance, USA) was applied. Positive Aβ staining was detected with HRP-conjugated avidin (Zymed, USA) followed by exposure to DAB chromogen (Vector, USA). Images were captured by a CCD color video camera (ProgRes C14, Jenoptic, Jena, Germany) attached either to a Leica MZ6 binocular (Leica, Germany) for 4G8 staining or to a Leica DMLB microscope (Leica, Germany) for modified Thio-S staining. In both cases, Image-J Software (NIH, freeware) was used for the analyses of staining in the hippocampus. The graphs present the average size area of positive staining p=statistical significance by t-test of differences in plaque size between the BBS3 group and the P709 (isotype control mAb) group.
Figure 4B:
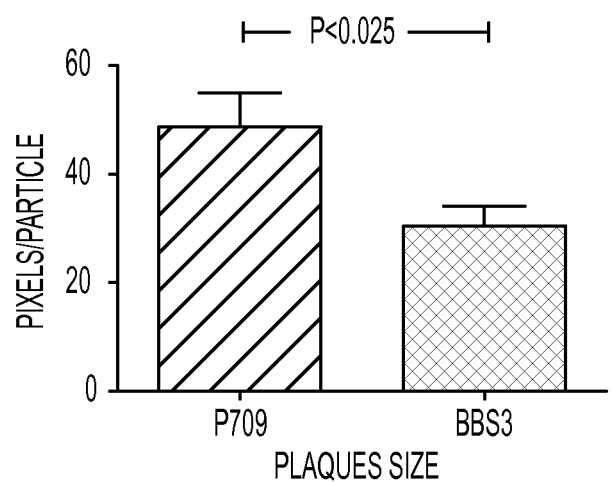

Aβ is derived from transmembrane APP by consecutive proteolytic cleavages. Accumulation of Aβ peptides leads to deposition of senile plaques in the extracellular space, eventually causing neuronal death. Evaluation of Aβ levels in this study showed that BBS3 mAb significantly reduced total Aβ accumulation and average plaque size, compared with mice treated with control mAb. The insoluble fraction of brain homogenates showed a significant decrease in toxic Aβ1-42 and total Aβ intracellular forms following BBS3 mAb treatment (FIGS. 3A and 3B). Histological analyses of hippocampus demonstrated significant reductions both in the size of dense core plaques of Aβ tested by Modified Thio-S staining (FIG. 4A) and in total Aβ burden detected by immunostaining with the 4G8 antibody (FIG. 4B) in mice treated with BBS3 mAb.

In summary, using the triple transgenic mouse model, ICV administration of BBS3 mAb for 6 weeks improves cognitive functions as shown in two distinct behavioral tests, and improved Aβ-related pathology as evidenced by reductions in plaque burden, insoluble Aβ levels and intracellular Aβ within the hippocampal neurons.

Example 8

Treatment of Alzheimer's Disease

Efficacy of BBS3 mAb is to be assessed in a clinical trial of patients with at least some symptoms of AD. Optionally, patients having one or more AD markers but who are otherwise pre-symptomatic are to be included. The patients are to receive doses of BBS3 mAb over, e.g., a 1- to 6-month interval or longer at a dosing frequency of e.g. weekly to monthly, at dosage levels of, e.g., 0 (placebo group), 2, 6 and 15 mg/kg body-weight. Other dosing intervals and frequencies and dosage levels may be useful for treating or preventing progression. Safety of BBS3 mAb is to be assessed by monitoring the subjects for reported adverse events (AEs) and by interpreting the results of various laboratory tests for safety, which may include general blood chemistry, liver and kidney functions, and CBC including WBC differentials, as well as by comparing the frequency and patterns of AEs in the BBS3 mAb groups compared to that of the placebo group. Efficacy is based on improvement in one or more of the following parameters: reduced AD markers and/or reduced AD symptoms and/or improved cognitive function. Efficacy assessments for each subject are to be ascertained by comparing values in efficacy parameters before BBS3 mAb immunotherapy to those during and after immunotherapy, as well as by comparing overall changes in efficacy parameters among one or more of the BBS3 mAb groups compared to the placebo group. Efficacy may also be based on mental, psychiatric and neuropyschological assessments, blood tests, brain imaging (PET, MRI, CT scan), urine tests, tests on the cerebrospinal fluid obtained through lumbar puncture, or the like.

Example 9

Design, Expression and Evaluations of Humanized BBS3 mAbs

The BBS3 CDRs (Table 1, SEQ ID NOs:9-14) are inserted into human FR regions to create humanized mAbs by means of humanization technology, a non-limiting example of which is COMPOSITE HUMAN ANTIBODY™. A large set of human FR sequence segments that could be used to create humanized antibody variants was analyzed to assure de-immunization using technologies to evaluate peptide binding to human MHC class II alleles (Perry at al, 2008) and for known antibody-related T-cell epitopes (Bryson et al, 2010). Sequence segments that were identified as significant non-human germ-line binders to human MHC class II or that scored significant hits as T-cell epitopes were discarded. Combinations of these were analyzed to ensure that the junctions between segments did not contain potential T-cell epitopes. Selected de-immunized FR segments were then combined with BBS3 CDRs (Table 1, SEQ ID NOs:9-14) to produce H- and L-chain V-region sequences for synthesis. Five VH chains and four VL (Vκ) chains were designed with nucleotide and amino acid sequences (with CDR sequences shown underlined), as follows:

VH Chain Sequences:
VH1:
EVQLVQSGPELKKPGASVKISCKASGYTFT<u>DYNMH</u>WVKQAHGKGLEWIG<u>Y IYPHNGGTGYNQRFKS</u>KATLTVDKSTSTAYMELRSLTSEDSAVYYCARP<u>G TEAY</u>WGQGTLVTVSS
(SEQ ID NO: 35 encoded by the nucleotide sequence of SEQ ID NO: 34)

VH2:
EVQLVQSGAEVKKPGASVKISCKASGYTFT<u>DYNMH</u>WVKQAHGKGLEWIG<u>Y

IYPHNGGTGYNQRFKS</u>KATLTVDKSTSTAYMELSSLRSEDSAVYYCARP<u>G

TEAY</u>WGQGTLVTVSS
(SEQ ID NO: 37 encoded by the nucleotide sequence of SEQ ID NO: 36)

VH3:
EVQLVQSGAEVKKPGASVKISCKASGYTFT<u>DYNMH</u>WVKQAPGKGLEWIG<u>Y

IYPHNGGTGYNQRFKS</u>KATLTVDKSTSTAYMELSSLRSEDTAVYYCARP<u>G

TEAY</u>WGQGTLVTVSS
(SEQ ID NO: 39 encoded by the nucleotide sequence of SEQ ID NO: 38)

VH4:
EVQLVQSGAEVKKPGASVKISCKASGYTFT<u>DYNMH</u>WVRQAPGKGLEWIG<u>Y

IYPHNGGTGYNQRFKS</u>KATLTVDKSTSTAYMELSSLRSEDTAVYYCARP<u>G

TEAY</u>WGQGTLVTVSS
(SEQ ID NO: 41 encoded by the nucleotide sequence of SEQ ID NO: 40)

VH5:
EVQLVQSGAEVKKPGASVKVSCKASGYTFT<u>DYNMH</u>WVRQAPGKGLEWIG<u>Y

IYPHNGGTGYNQRFKS</u>KATITVDKSTSTAYMELSSLRSEDTAVYYCARP<u>G

TEAY</u>WGQGTLVTVSS
(SEQ ID NO: 43 encoded by the nucleotide sequence of SEQ ID NO: 42)

VL Chain Sequences:
VL1:
DIVMTQSPSFMSASVGDRVTITC<u>KASQNVGTNVA</u>WYQQKPGKAPKPLIY<u>S ASYRYS</u>GVPDRFTGSGSGTDFTLTISSLQSEDVAEYFC<u>QQFNSYPLT</u>FGG GTKVEIK
(SEQ ID NO: 45 encoded by the nucleotide sequence of SEQ ID NO: 44)

VL2:
DIVMTQSPSSMSASVGDRVTITC<u>KASQNVGTNVA</u>WYQQKPGKAPKPLIY<u>S

ASYRYS</u>GVPDRFTGSGSGTDFTLTISSLQAEDVAEYFC<u>QQFNSYPLT</u>FGG

GTKVEIK
(SEQ ID NO: 47 encoded by the nucleotide sequence of SEQ ID NO: 46)

VL3:
DIVMTQSPSSMSASVGDRVTITC<u>KASQNVGTNVA</u>WYQQKPGKAPKPLIY<u>S

ASYRYS</u>GVPDRFSGSGSGTDFTLTISSLQAEDVAEYFC<u>QQFNSYPLT</u>FGG

GTKVEIK
(SEQ ID NO: 49 encoded by the nucleotide sequence of SEQ ID NO: 48)

VL4:
DIQMTQSPSSMSASVGDRVTITC<u>KASQNVGTNVA</u>WYQQKPGKAPKPLIY<u>S

ASYRYS</u>GVPDRFSGSGSGTDFTLTISSLQAEDVAEYFC<u>QQFNSYPLT</u>FGG

GTKVEIK
(SEQ ID NO: 51 encoded by the nucleotide sequence of SEQ ID NO: 50)

Humanization is preferably performed by constructing an antibody comprised of humanized VH and VL regions with the human IgG4 CH region and κ CL (Cκ) region. The IgG4 CH region also contains a mutation (Ser241Pro), which is known to eliminate the formation of IgG4 half-antibodies and chain exchange (Angal et al, 1993); this modified human CH region is called IgG4(Ser241Pro). Each of the five VH amino acid sequences (VH1-5; SEQ ID NOs:35, 37, 39, 41 and 43) is designed into a full-length H chain by adding the amino acid sequences of the IgG4(Ser241Pro) region to the C-terminus; this results in five humanized H-chain amino acid sequences. Each of the four VL amino acid sequences (VL1-4; SEQ ID NOs:45, 47, 49 and 51) is designed into a full-length L chain by adding the amino acid sequences of the Cκ region to the C-terminus; this results in four humanized L-chain (κ) amino acid sequences. These five H and four L amino acid sequences are converted into five H chain- and four L chain-encoding DNA sequences, corresponding to nine humanized genes for recombinant expression of humanized antibodies.

Figure 5:
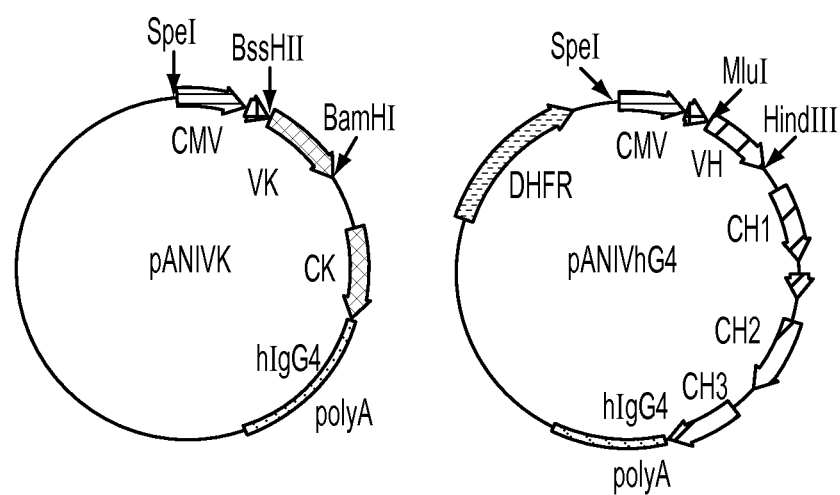
FIG. 5 is a schematic diagram of the pANT expression vectors. VH and Vκ vectors both contain genomic DNA fragments incorporating introns and poly-A sequences. Expression of both chains is driven by a CMV immediate early gene promoter. Both vectors also contain an EBV OriP for enhanced transient expression in HEK/EBNA cells.

All five humanized VH genes (VH1-5) and four humanized VL (Vκ) genes (VL1-4) are synthesized using a series of overlapping oligonucleotides that are annealed, ligated and PCR-amplified to give full-length VH and Vκ regions. The assembled VH and Vκ regions are cloned into the pANT expression vector system for IgG4(Ser241Pro) chains (FIG. 5, with new VH chains and Vκ regions) using MluI and HindIII restriction sites for the VH region and using BssHII and BamHI restriction sites for the Vκ region. All constructs are confirmed by sequencing.

Combinations of five IgG4(Ser241Pro) VH and four Vκ chains (20 pairings in all, designated VH1/VL1, VH1/VL2, VH1/VL3, VH1/VL4, VH2/VL1, VH2/VL2, VH2/VL3, VH2/VL4, VH3/VL1, VH3/VL2, VH3/VL3, VH3/VL4, VH4/VL1, VH4/VL2, VH4/VL3, VH4/VL4, VH5/VL1, VH5/VL2, VH5/VL3, and VH5/VL4) are co-transfected into HEK/EBNA cells using linear PEI, and the cells are incubated for 4 days post-transfection for detection of full mAbs. Supernatants with expressed mAbs are assayed for IgG levels using an IgG4 ELISA. MAbs are purified from supernatants on a Protein A Sepharose column and buffer exchanged into PBS, pH 7.4. Purified Aβ is quantified by $OD_{280}$ using an extinction coefficient (Ec(0.1%)=1.62) based on the predicted amino acid sequences. The variants are analyzed by SDS-PAGE and bands corresponding to the predicted sizes of the H and L chains are observed.

Purified mAbs are assayed by ELISA vs. WT peptide as described in Example 1. A subgroup of the most ELISA-reactive mAbs is assayed for affinity by BIAcore as described in Example 5. A subgroup of the highest affinity mAbs are assayed for activity in cell culture as described in Example 6. Based on the data for affinity and cell culture activity, the lead humanized MAb is selected for further development.

Initial results of with several humanized BBS3 mAbs showed that they had similar percent inhibition of extracellular and intracellular Aβ as the murine BBS3 mAb.

Example 10

Beneficial Effect of BBS3 in ALS Transgenic Mice

Materials and Methods
Transgenic Mice and Antibody Treatment

All animal experiments were conducted in accordance with the Guide for the Care and Use of Laboratory Animals and were approved by the Institutional Animal Care and Use Committee of Tel Aviv University.

SOD1$^{G93A}$ mice carrying the G93A human SOD1 mutation were obtained from the Jackson Laboratory (Bar Harbor, Me., USA). Male SOD1$^{G93A}$ transgenic (Tg) mice were crossbred with C57Bl/6 females (Gurney et al. 1994).

For evaluation of APP expression, phosphorylation and processing Tg mice and non transgenic (NT) littermates were sacrificed at different ages by i.p. anesthesia (100 mg/kg Ketamine and 20 mg/kg Xylazine) following transcardial perfusion with saline.

Male SOD1$^{G93A}$ mice were treated with BBS3 MAb or isotype-matched control Non relevant anti-*Streptococcus pneumoniae* MAb (Non relevant MAb). The 55-days old mice were anesthetized and implanted with brain infusion cannula into the right lateral ventricl (1-2 mm [Bregma] in the anterio-posterior direction, 2.8 mm in mediolateral direction and 3 mm depth). Brain infusion cannula was connected with osmotic mini-pump Model 2006 (Alzet, Cupertino, Calif., USA), which continuously delivered the MAb (concentration 1.5 mg/mL, pumping rate 0.15 µL/h). After 42 days of treatment some of the mice were sacrificed for biochemical (n=4 in BBS3 group, n=5 in non relevant antibody group) and histological analysis (n=5 in BBS3 group, n=5 in non relevant antibody group). The rest of the mice (n=8 in each group) continued to receive the MAbs via intraperitoneal (i.p.) injection (16 mg/kg biweekly) until the end stage of the study.

Clinical Assessment

During the treatment period, mice were weighed and their muscle strength and coordination deficits were evaluated weekly using a Rotarod apparatus (rotating at an increasing speed ranging from 4 to 40 RPM, with a constant acceleration of 1 RPM per 10 sec, 3 attempts). Mice were trained on the machine for 3 days before beginning the analysis. The time up to 300 sec during which each mouse remained on the drum was recorded. The survival was defined as the age when the animal could not right itself within 30 sec when placed on its side.

Tissue Fractionation and Immunoblotting

Mice were sacrificed at the age of 97 days. Their spinal cords and brains were collected and homogenized on ice in 5 volumes (w/v) of T-per extraction buffer (Pierce, USA) complemented with protease inhibitor tablets (Complete Mini Protease Inhibitor Tablets, Roche) and phosphatase inhibitor cocktail tablets (phosSTOP, Roche). After sonication, homogenates were centrifuged at 100,000 g for 1 hr at 4° C. The resulting supernatants represent the soluble fraction.

The pellets were resuspended in T-per extraction buffer, containing protease and phosphatase inhibitors, 0.5% TritonX-100, 1% sodium deoxycholate and 3% SDS, sonicated and centrifuged at 20,000 g for 10 min at 4° C. The resulting supernatants represent the membrane fraction.

Protein concentration was determined using BCA protein assay kit (Thermo, USA), and samples were analyzed by immunoblotting with the following primary antibodies: mouse anti-APP 22C11 (1:2000 Millipore), rabbit anti-Phospho-APP T668 (1:1000 Cell Signaling Technology), rabbit anti-sAPPβ (1:500 Covance), anti-BACE C-terminus clone 61-3E7 (Millipore), mouse anti-total GSK3β (1:500 Sigma), Rabbit anti-GSK-3α[pY279]/β[pY216] (1:1000 Invitrogen), PAb-240 mouse anti p53 (1:1000 Abcam), and SD-G6 mouse anti-human SOD1 (1:1000 Sigma). Immunoblots were developed with EZ-ECL detection kit (Biological Industries, Israel), and quantitative densitometric analysis was performed using the densitometry software EZQuant-Gel 2.12.

Immunohistochemistry

Spinal cords collected from 97 days old SOD1$^{G93A}$ mice were fixed in 4% (w/v) paraformaldehyde in PBS (pH 7.4) and sedimented in 30% sucrose in PBS. 30 µm free-floating cryosections were prepared from lumber spinal cords. Sections were blocked with Ultra-V block (Lab Vision, USA) for 10 min. Motor neuron survival was evaluated by Choline acetyltransferase (ChAT) immunostaining Sections were incubated with primary goat anti-ChAT antibody (1:100, Millipore) for 1 hr at 37° C., following incubation with secondary anti-goat Cy3 conjugated antibody (1:200 Jackson ImmunResearch) for 1 hr. Sections were mounted with Prolong Gold Antifade containing Dapi Reagent (Invitrogen). ChAT-positive motor neurons with visible nucleoli were counted in the ventral horns of all sections from lumbar regions at the L2-5 level. The number of motor neurons was counted in 5 sections per mouse in a blinded manner. Results were expressed as the average of total motor neurons counted divided by the number of sections. For astrocytosis evaluation, sections were immunostained with rabbit anti GFAP antibody (1:500 Dako, Denmark) and applied for overnight incubation at 4° C. HRP-conjugated goat anti-rabbit IgG Fc antibody (1:1000 Jackson ImmunResearch) was applied for 1 hr. Sections were visualized using DAB chromogen substrate (Invitrogen, USA), dehydrated in graded alcohol, cleared in xylene and cover-slipped with enthelan (Merck, Germany). Image-J Software (NIH, freeware) was used for the analysis.

Statistical Analyses

Survival was analyzed using the Kaplan-Meier with log-rank test. Behavioral analysis, immunohistochemistry, ELISA and biochemistry, presented as the mean±SEM, was subjected to one-way ANOVA followed by Tukey-Kramer post hoc test or Student's t-test. The critical P value was set to 0.05 for all statistical analyses.

Figure 6A:
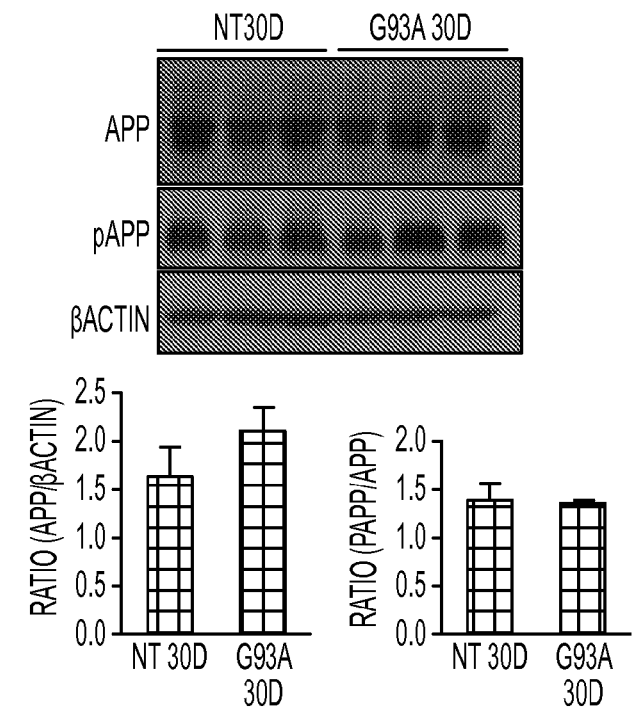
FIGS. 6A-6B show APP expression and phosphorylation in spinal cords of pre-symptomatic and symptomatic mice. Spinal cords from 30- and 80-day-old and end stage SOD1$^{G93A}$ mice were homogenized and their membrane fractions were subjected to immunoblot analysis. Age matched NT littermates served as control. For APP detection 22C11 antibody was used. For detection of phosphorylated APP (pAPP) a specific polyclonal anti pAPP T688 was used. β-Actin was used as an internal loading control. Immunoblot blot and densitometric analysis of the relative expression and phosphorylation levels of APP in the spinal cord of (FIG. 6A) 30-day-old mice, (FIG. 6B) 80-day-old and end stage SOD1$^{G93A}$ mice. All values are expressed as the mean±SEM. Statistical comparisons were performed using one-way ANOVA followed by Tukey-Kramer post hoc test. N(NT 30D)=3, N(G93A 30D)=3, N(NT=4), N(G93A 80D)=4, N(G93A end stage=3). *p<0.05; **p<0.01 (v.s. NT littermates).
Figure 6B:
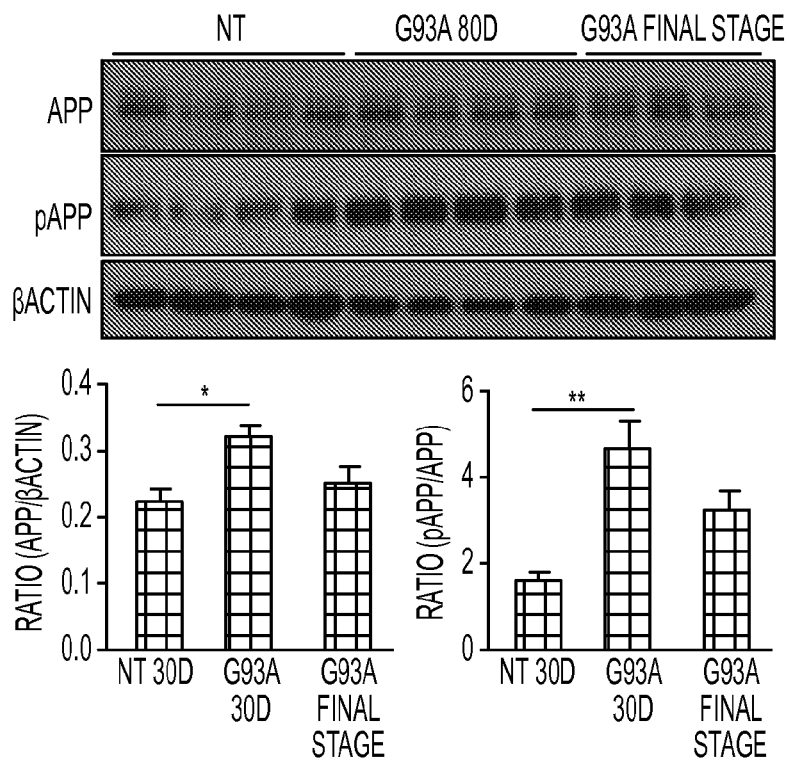

Results:

Effect of Mutant SOD1$^{G93A}$ on Expression and Phosphorylation of APP in the Spinal Cord The effect of mutant SOD1 on APP expression was evaluated throughout the disease progression in SOD1$^{G93A}$ ALS mouse model. Changes in APP protein expression in the spinal cords were assessed at presymptomatic (30-day-old and 80-day-old) and symptomatic end stage of the disease compared to non Tg (NT) littermates. An increase (1.39-fold) in APP levels was detectable as early as 30 days in the spinal cords of SOD1$^{G93A}$ mice compared to NT mice (FIG. 6A). A similar trend was observed at the age of 80 days (significant 1.45-fold increase). However, at the end stage of the disease, there was a non-significant reduction in the levels of APP in comparison to the levels of 80-day-old mice (FIG. 6B). APP undergoes post-translational modifications such as phosphorylation. Phosphorylation at threonine 668 (T668) is associated with enhanced BACE cleavage of APP (Lee et al., 2003). A significant (2.9-fold increase) in T668 phosphorylation was detected in spinal cords of 80-days-old SOD1$^{G93A}$ mice (FIG. 6B). In 30-days-old SOD1$^{G93A}$ mice, there was no change in the phosphorylation of APP compared to NT mice (FIG. 6A).

Effect of Mutant SOD1$^{G93A}$ on APP Processing in the Spinal Cord

Figure 7A:
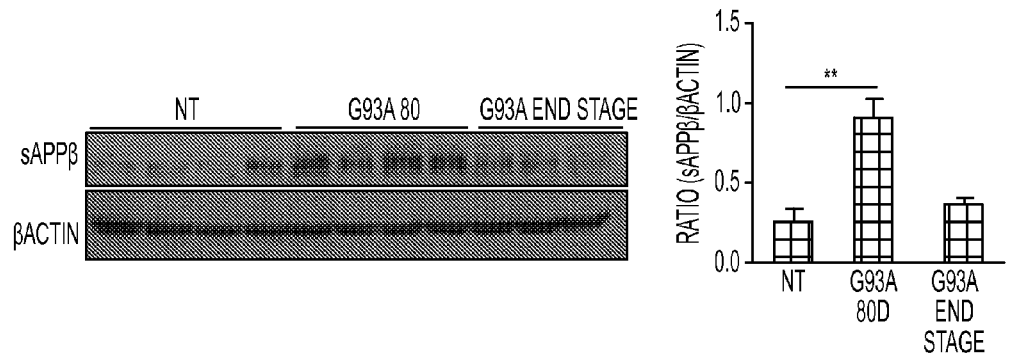
FIGS. 7A-7B show the effect of mutant SOD1 on APP processing in spinal cords of presymtomatic and symptomatic mice. Soluble and membrane fractions from 80-day-old and end stage SOD1$^{G93A}$ mice were subjected to immunoblot analysis. Age matched NT littermates served as control.
Figure 7B:
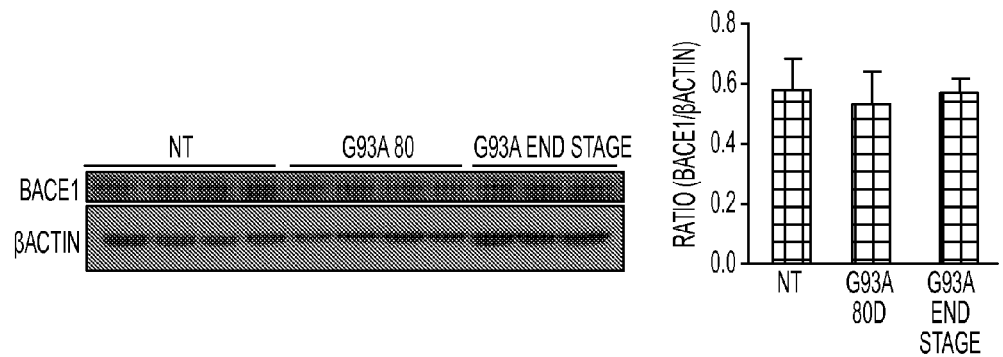
Figure 8A:
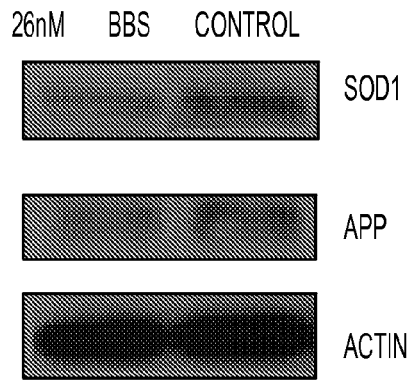
FIGS. 8A-8C show the reduction in the levels of mutant SOD1 in NSC34 stable line over-expressing mutant G93A SOD1 fused to GFP as a result of BBS3 treatment. Induction of mutant G93A SOD1 expression was performed by incubating the cells with Doxycycline for 48 h. 24 h after the induction the cells were treated with 26 nM BBS3 for 24 h. The levels of mutant SOD1, APP and actin were measured using Western blot analysis.
Figure 8B:
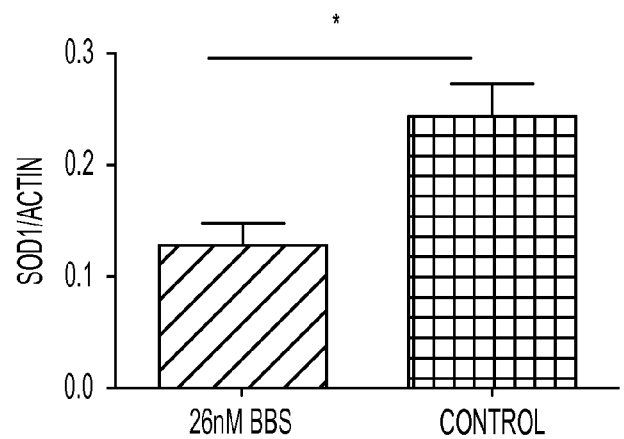
Figure 8C:
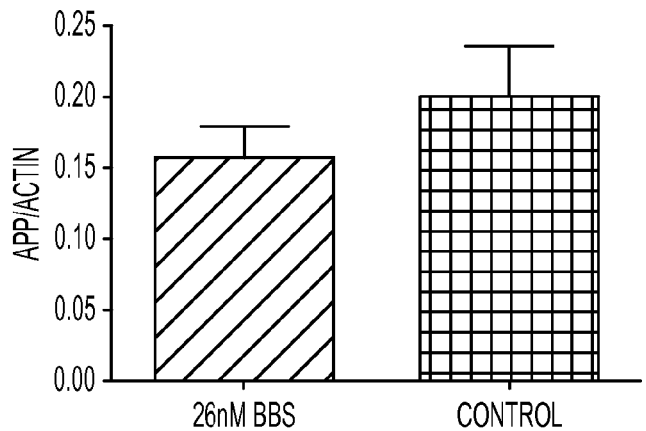
Figure 9A:
FIGS. 9A-9C show reduction in the levels of mutant SOD1 in primary astrocytes as a result of BBS3 treatment. Primary astrocytes were isolated from mutant G93A SOD1 mice. After 7 days in culture, the cells were treated with 13 nM BBS3 for 24 h. The levels of mutant SOD1, APP and actin were measured using Western blot analysis.
Figure 9B:
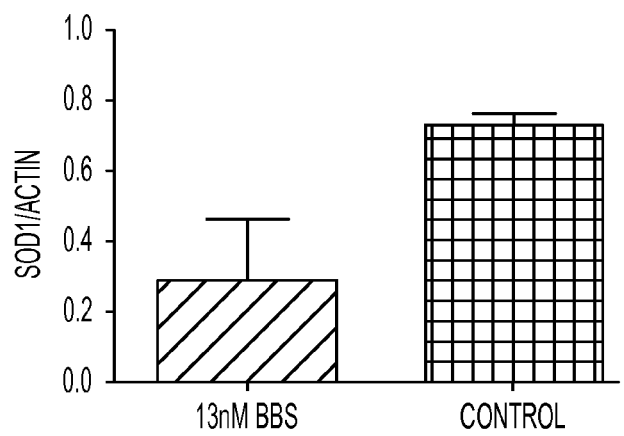
Figure 9C:
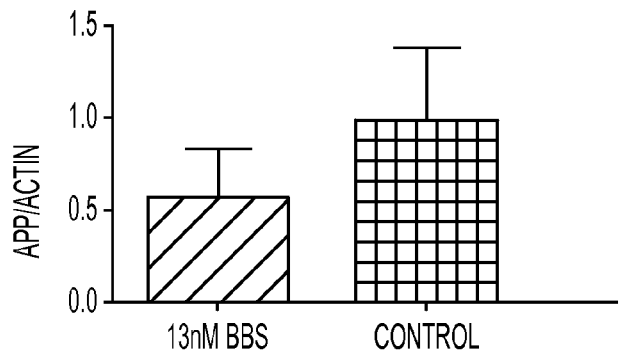
Figure 10A:
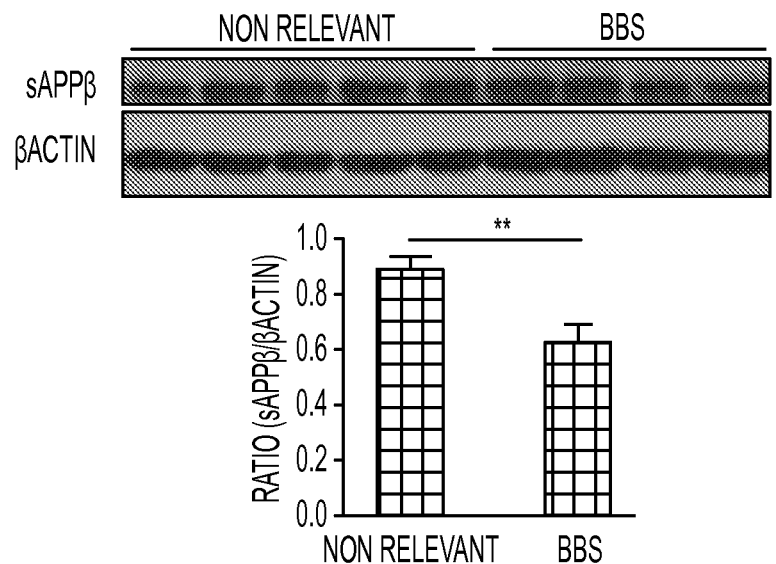
FIGS. 10A-10B show the effect of BBS3 MAb on APP expression and processing in the spinal cords of SOD$^{G93A}$ mice. 55-day-old male SOD$^{G93A}$ mice were implanted i.c.v. with Alzet osmotic pumps that continuously delivered BBS3 or non relevant MAb for 42 days. Mice were sacrificed at age 97 days (Day 42 of treatment), and spinal cords were homogenized and subjected to immunoblot analysis.
Figure 10B:
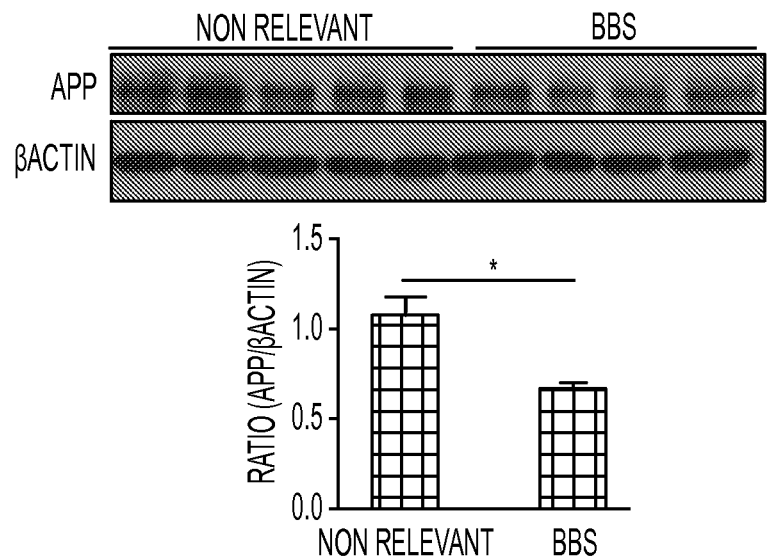
Figure 11A:
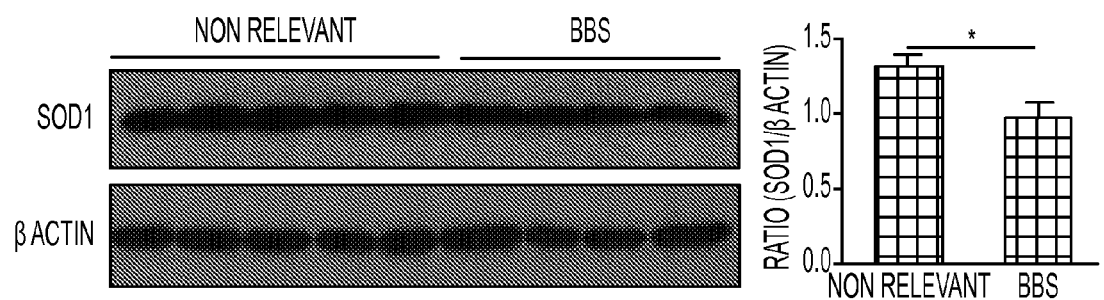
FIGS. 11A-11B show the evaluation of BBS3 MAb effect on mutant SOD1 levels in spinal cords of SOD1$^{G93A}$ mice. SOD1 levels were quantified using immunoblot analysis in soluble and membrane fractions of spinal cord homogenates of SOD1$^{G93A}$ mice treated with BBS or non relevant MAb for 42 days. The levels of SOD1 were normalized to β-Actin using densitometric analysis. Membrane (FIG. 11A) and Soluble (FIG. 11B) SOD1 levels were detected using specific anti-human-SOD1 MAb. Statistical comparisons were performed using Student's t-test. N(BBS)=4, N(Non relevant)=5. *p<0.05 (v.s. Non relevant).
Figure 11B:
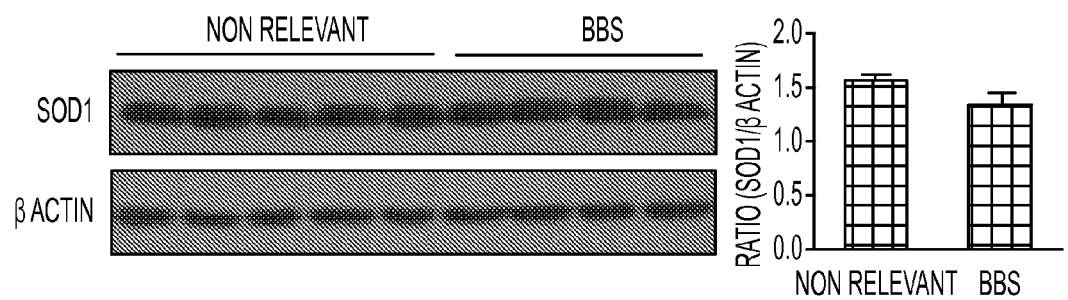

Since the analysis of APP phosphorylation associated with enhanced processing by BACE revealed significant up-regulation at age 80 days, BACE processing of APP was evaluated. The levels of soluble APPβ fragment (sAPPβ), a product generated by BACE cleavage, were measured in the spinal cords of SOD1$^{G93A}$ mice. Levels of sAPPβ were significantly elevated (3.5-fold) in 80-day-old SOD1$^{G93A}$ mice compared to NT mice. As the disease progressed, sAPPβ levels decreased compared to pre-symptomatic 80-day-old mice (FIG. 7A). This pattern correlates with expression and phosphorylation of APP throughout the different stages of the disease in the spinal cords. The increase in spinal cord sAPPβ levels may also be attributed to increased BACE1 expression. However, there was no change in BACE1 levels at any stage of the disease, in comparison to NT mice (FIG. 7B).

BBS3 Treatment Leads to Reduction in APP and SOD1$^{G93A}$ Levels

In order to understand if there is a crosstalk between APP and mutant SOD1, cellular models including primary astrocytes isolated from SOD1$^{G93A}$ mice and inducible NSC34 stable line overexpressing mutant SOD1$^{G93A}$ as well as mutant SOD1 mice were treated with MAb BBS3. As shown in FIGS. 8A-8C and 9A-9C, BBS3 treatment in cellular models resulted in reduction in the levels of APP and mutant SOD1. However, no reduction in the levels of APP was observed in a treatment with the BBS1 MAb, a first generation monoclonal antibody directed to the β-secretase (BACE) cleavage site on APP and blocks cleavage thereof by BACE (data not shown). There was also a significant reduction in the levels of APP processing product sAPPβ (1.4-fold), APP (1.5-fold) and mutant SOD1 (1.3-fold) in spinal cords of BBS3 treated SOD1$^{G93A}$ mice (FIGS. 10A-10B, 11A-11B).

Inhibition of APP Processing Modulates Downstream Pro-Apoptotic Targets

Figure 12A:
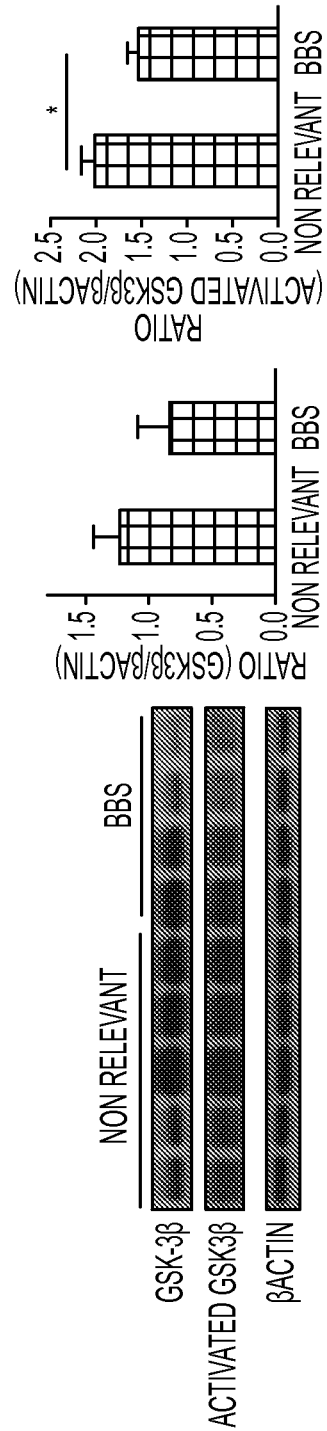
FIGS. 12A-12B show the effect of APP processing inhibition on expression and activation of GSK-3β and p53. The levels of GSK-3β, activated pGSK-3 and p53 were quantified using immunoblot analysis in the soluble fraction of spinal cord homogenates of SOD$^{G93A}$ mice treated with BBS or non relevant MAb for 42 days.
Figure 12B:
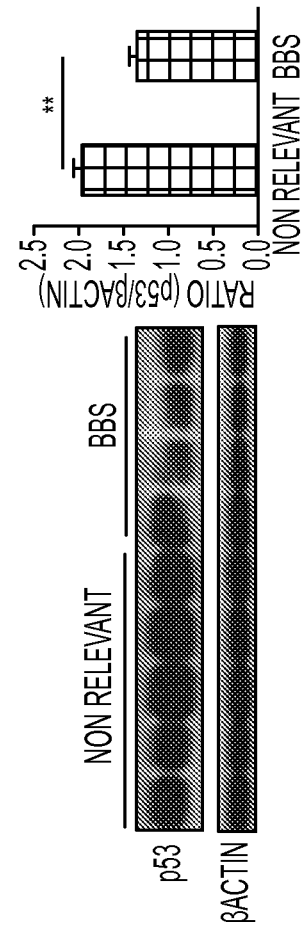

The effect of APP and its cleavage products might be mediated through downstream toxic targets. AICD was proposed to up-regulate transcription of serine/threonine kinase Glycogen synthase kinase-3β (GSK-3β), and the pro-apoptotic p53 (Kim et al. 2003, Ozaki et al. 2006). GSK-3β activity could be one of the potentially pathogenic mechanisms in ALS, since inhibition of its activity prevents motor neuron death, while P53 might be involved in neuronal degeneration in spinal cords of SOD1$^{G93A}$ mice (Koh et al. 2007, Ranganathan & Bowser 2010). It was observed that there was a 1.4-fold decrease in levels of GSK-3β and a significant 1.3-fold decrease in activation of this protein in spinal cords of BBS3-treated mice (FIG. 12A). Coincident with this, was a significant 1.5-fold reduction in p53 levels in spinal cords of SOD1$^{G93A}$ mice (FIG. 12B).

Figure 13:
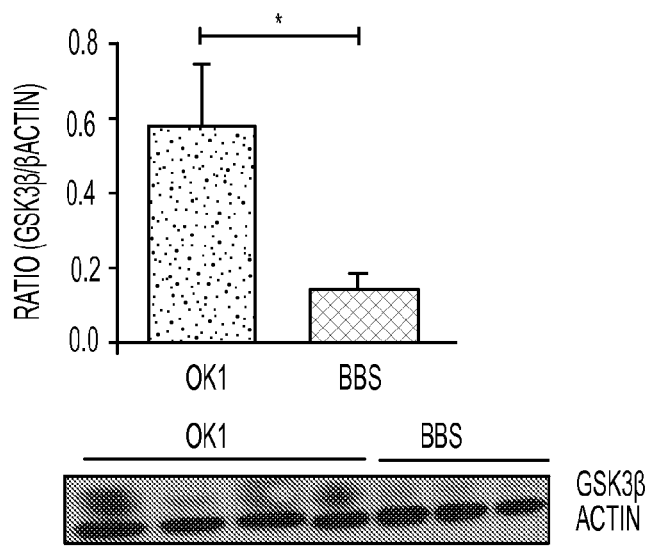
FIG. 13 shows that BBS1 monoclonal antibody (mAb) reduced the level of GSK3β as quantified by immunoblot

Total GSK3β levels were significantly decreased by 74% with BBS1 MAb (FIG. 13), and levels of GSK3β phosphorylated at Tyr216 were decreased to the same extent (data not shown).

Effect of BBS3 Treatment on Motor Neurons and Astrogliosis

Figure 14A:
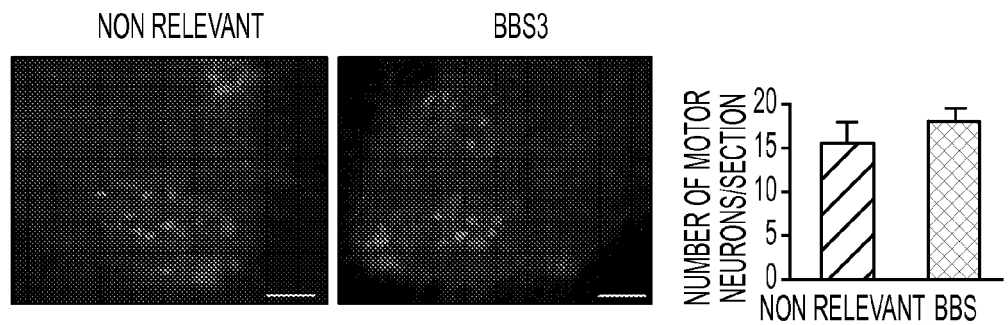
FIGS. 14A-14B show the effect of BBS treatment on number of motor neurons and astrogliosis in the lumber spinal cords of SOD1$^{G93A}$ mice. SOD1$^{G93A}$ mice treated i.c.v with BBS or non relevant MAb starting at age 55 days were sacrificed at age 97 days. Lumber spinal cords were subjected to immunohistochemical analysis.

To further assess the neuroprotective effect of BBS3 MAb, lumber spinal cords of treated SOD1$^{G93A}$ mice were collected and subjected to immunohistochemical analysis. Spinal cord sections were stained with the motor neuron marker Chat, and Chat-positive neuronal cell bodies were counted in each section. There was a slight increase in the number of motor neurons in the BBS3-treated group (FIG. 14A).

Figure 14B:
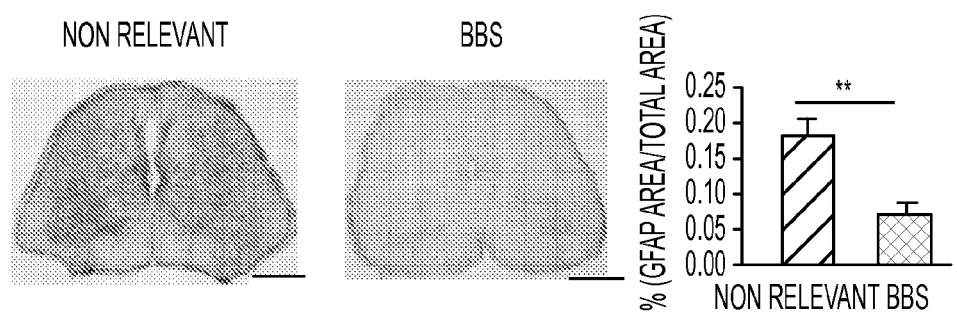

Since astrocytes play a major role in ALS pathology (Alexianu et al. 2001), we examined the effect of BBS3 treatment on astrogliosis in SOD1$^{G93A}$ mice. Lumber spinal cord sections were probed for the presence of the activated astrocytes marker Glial fibrillary acidic protein (GFAP). There was a significant 2.5-fold decrease in the levels of GFAP in the lumber spinal cords of BBS3 treated SOD$^{G93A}$ mice (FIG. 14B) compared to Control. These data indicate that inhibition of APP processing reduces astrogliosis in SOD1$^{G93A}$ mice.

Figure 15:
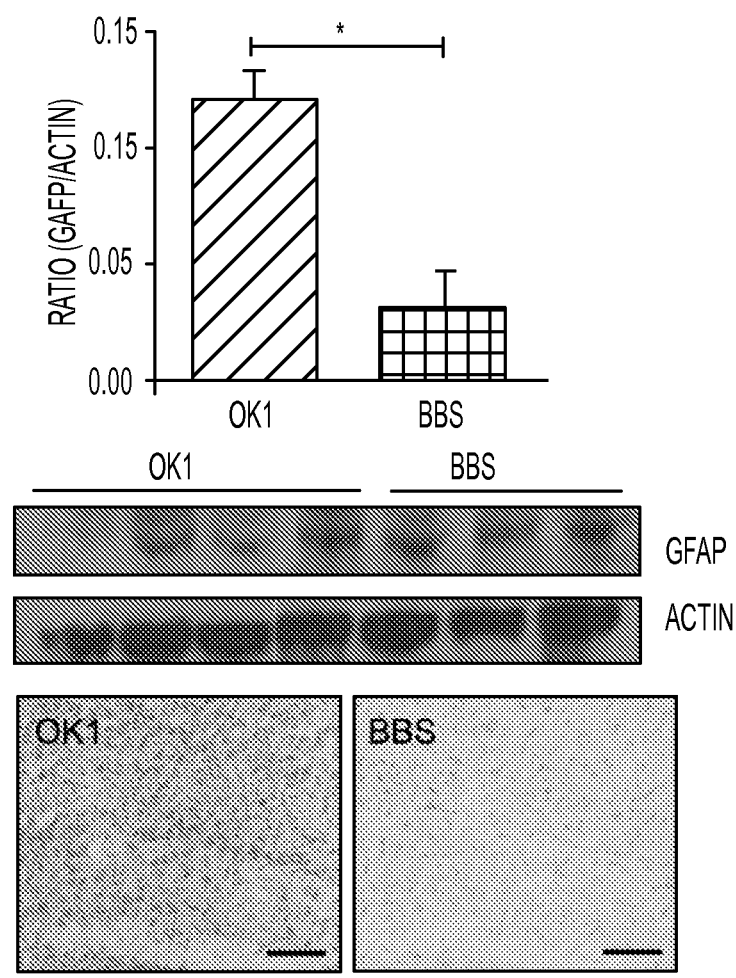
FIG. 15 shows the evaluation of BBS1 mAb on inflammation. GFAP levels were measured as indicative of astrocyte-reactive levels in both immunostaining and immunoblot analysis (FIG. 15). Scale bar is 100 μm.
Figure 16A:
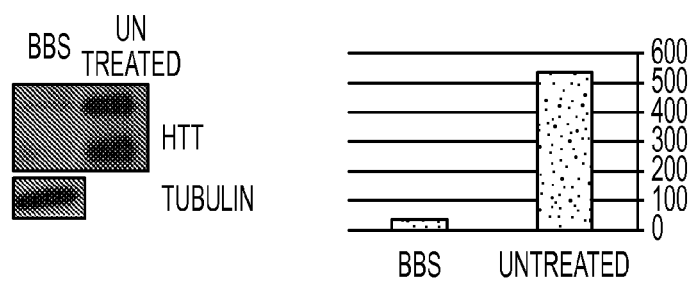
FIGS. 16A-16D show the reduction in the levels of htt N-terminal and APP C-terminal in hek293t cells transiently transfected with either the wt form of the htt gene N171-18Q or with the mutant form N171-82Q as a result of mAb BBS3 treatment.
Figure 16B:
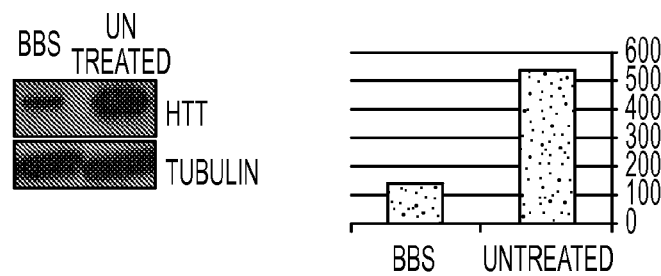
Figure 16C:
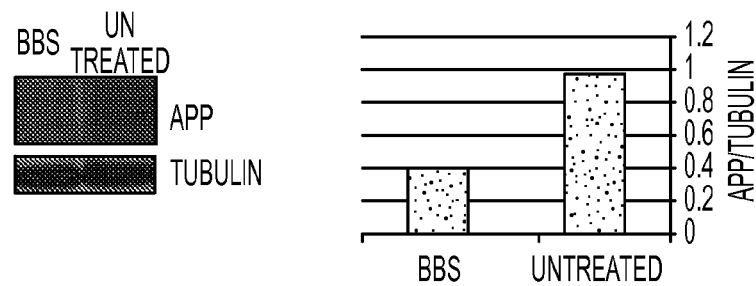
Figure 16D:
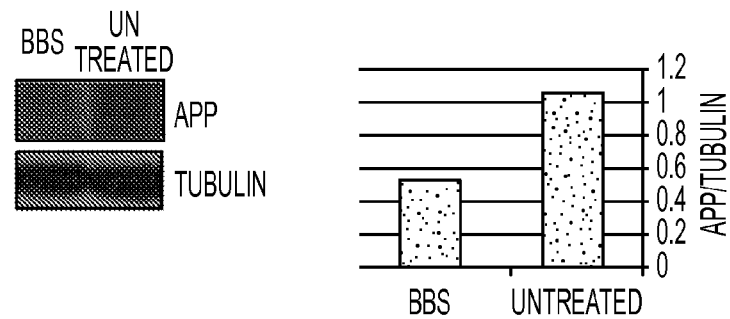
Figure 17A:
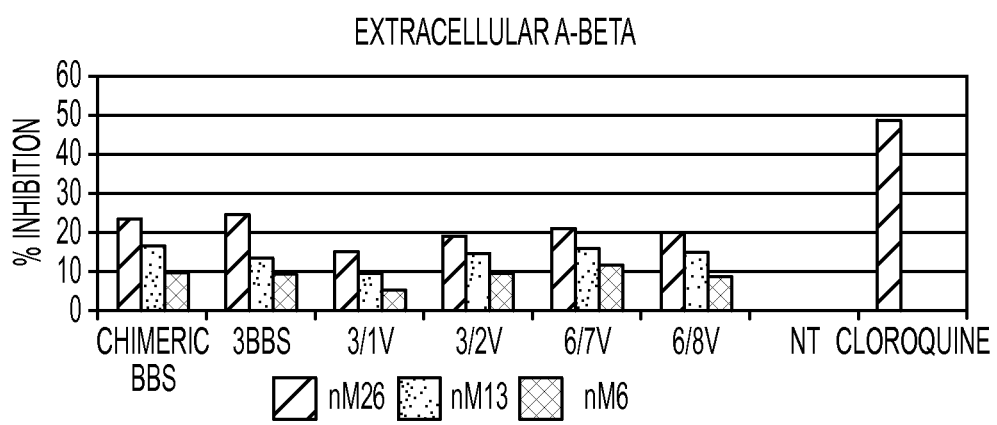
FIGS. 17A-17B show the inhibitory effect of humanized BBS3 mAbs in an Aβ formation assay in CHO APP751 cells. The levels of secreted and intracellular Aβ were quantified using a sandwich ELISA that utilizes mAb 6E10 (Covence) as the capture antibody and biotinylated 4G8 (Covence). Secreted Aβ (FIG. 17A) was measured in samples of media which were collected after 24 hours incubation with human BBS3 antibody in 26 nM, 13 nM, and 6 nM concentrations. Intracellular Aβ (FIG. 17B) was measured in cells which were collected after 5 day of incubation with human BBS3 antibody. Callibration curve of Aβ42 (804, 800 nM, 80 nM, 8 nM, 800 pM, 80 pM and 8 pM) were used to determine the level of Aβ in samples.
Figure 17B:
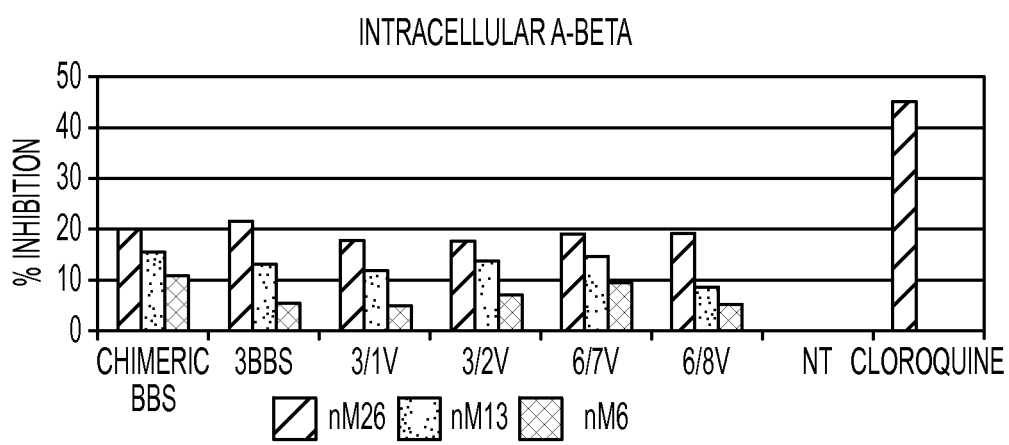

Severity of AD pathology correlates strongly with the density of astrocytes. The glial fibrillary acidic protein (GFAP) is upregulated in activated astrocytes. Levels of GFAP were tested in both immunohistochemical and biochemical methods and revealed a significant decrease of 74% in the activated astrocytes levels in mice treated with mAb BBS1 relative to a control mAb (FIG. 15).

Discussion

Changes in APP expression and processing in spinal cords, muscles and CSF of ALS patients led the present inventors to investigate how APP is involved in pathological molecular and cellular events in Tg SOD1G93A mice (Sasaki and Iwata, 1999; Calingasan et al., 2005; Koistinen et al., 2006).

The present inventors found that an increase in APP expression in spinal cords of SOD1$^{G93A}$ mice occurred as early as 30 days and continued as the disease progressed. However, at the end stage of the disease, the levels of APP decreased, but still remained higher than in NT littermates. These findings are in concordance with other reports of CNS insults where APP levels increased at early stages. For instance, APP levels were elevated in damaged axons within acute multiple sclerosis lesions, and in the active borders of less acute lesions (Ferguson et al., 1997). APP expression was also increased in axonal injury in the early stage of brain damage and in motor neurons of aged rats and might be associated with degenerative processes of aging or dying motor neurons (Kawarabayashi et al., 1991; Solà et al., 1993; Xie et al., 2000).

In addition to changes in APP expression, an increase in its phosphorylation at threonine 688, which is associated with enhanced beta secretase cleavage, was also detected (Lee et al., 2003). The present inventors found that APP phosphorylation is increased only in spinal cords of 80-day-old mice, just before the clinical onset of the disease. Increased phosphorylation was accompanied by elevated levels of the BACE-processing product sAPPβ from APP. The fact that BACE1 levels remain unchanged in spinal cords of Tg mice suggests that increased APP processing is a result of increased APP phosphorylation. Indeed, increased phosphorylation related to processing was detected in AD patients (Chang et al., 2006). The increased phosphorylation of APP might be a consequence of upstream pathological pathways that occur before disease onset.

Buffer-insoluble SOD1 aggregates were significantly elevated in pre-symptomatic APP mutant SOD1 double Tg mice compared to age-matched mutant SOD1 single Tg mice (Li et al., 2006). In addition, it was demonstrated that intracellular Aβ directly interacts with wild type and SOD1$^{G93A}$, suggesting that APP processing might influence SOD1 aggregation (Yoon et al., 2009). The present inventors found that BBS3 treatment decreased the levels of mutant SOD1 in cellular and animal models of ALS. Our data indicates that modulation of APP processing and expression might interfere with SOD1 intracellular aggregation. Thus, part of the beneficial effect of the BBS3 MAb may be due to reduction in mutant SOD1 burden. It seems that mutant SOD1 enhances APP processin; on the other hand reduction in APP levels and processing via BBS treatment leads to reduction in the levels of mutant SOD1. These findings indicate that there is cross talk between APP and mutant SOD1 that might occur through some kind of interaction in the membrane.

Example 11

BBS3 Treatment Effect on APP and Huntingtin Levels in Huntington Disease Cellular Model Alzheimer Disease, ALS and Huntington Disease share several similar pathological aspects and mechanisms, such as aberrant protein that aggregates and form β-sheet structure and amyloid, increased neurodegeneration, mitochondrial dysfunction, oxidative stress, transcriptional dysregulation, aberrant apoptosis, altered proteosomal function. Due to the fact that BBS3 treatment had a beneficial effect in ameliorating some of these pathological aspects both AD and ALS cellular and mouse models, the present inventors speculated that huntingtin may be a good target that can benefit from BBS3 treatment.

Huntington disease (HD) is an autosomal-dominant, progressive, and fatal neurodegenerative disease that usually starts in midlife. Huntington disease (HD) is caused by the expansion of a glutamine (Q) repeat near the N terminus of huntingtin (htt), expands to a length greater than 36 consecutive glutamines. Neurons throughout the central nervous system harbor inclusion bodies that comprise of short mutant htt fragment, in both the nucleus and cytoplasm.

Hek293t cells were transiently transfected with the first 171aa N-terminal region of the mutant huntingtin gene containing 82 glutamine repeats (N171-82Q) or a normal wt construct containing 18 glutamine repeats (N171-18Q). 48 h post transfection, cells were treated for 24 h with 26 nM mAb BBS3 or vehicle. BBS3 mAb treatment significantly reduced the levels of htt and APP in either wt and mutant transfected cells in comparison to untreated cells. (FIGS. 16A-16D)

It is to be understood that while the invention has been described in conjunction with the detailed description thereof, the foregoing description is intended to illustrate and not limit the scope of the invention, which is defined by the scope of the appended claims. Optionally any one or more embodiments, sub-embodiments and/or components of any embodiment may be combined. Other aspects, advantages, and modifications are within the scope of the following claims. All references cited herein, including journal articles or abstracts, published or corresponding U.S. or foreign patent applications, issued U.S. or foreign patents, or any other references, are entirely incorporated by reference herein, including all data, tables, figures, and text presented in the cited references.

REFERENCES

Abbs et al, Ther Immunol 1: 325-31, 1994
Alexianu, M. E., Kozovska, M. and Appel, S. H. (2001) Immune reactivity in a mouse model of familial ALS correlates with disease progression. Neurology, 57, 1282-1289.
Angal et al, Molec Immunol 30: 105-8, 1993
Atschul et al, J. Molec. Biol. 215: 403-10, 1990
Beaucauge et al, Tetrahedron Let. 22:1859-62, 1981
Boado et al, Biotechnol Bioeng 102: 1251-8, 2009
Boado et al, Biotechnol Bioeng 96: 381-91, 2007
Bolt et al, Eur J Immunol 23: 403-11, 1993
Brown et al, J Biol Chem 255: 4980-3, 1980
Brown et al, J Immunol 127: 539-46, 1981
Brown et al, Meth. Enzymol. 68:109, 1979
Bryson et al, Biodrugs 24:1-8, 2010
Calingasan N Y, Chen J, Kiaei M, Beal M F (2005) Beta-amyloid 42 accumulation in the lumbar spinal cord motor neurons of amyotrophic lateral sclerosis patients. Neurobiol Dis 19:340-347
Chan et al., Nature Review Immunology, 10 301-16, 2010
Chang K-A, Kim H-S, Ha T-Y, Ha J-W, Shin K Y, Jeong Y H, Lee J-P, Park C-H, Kim S, Baik T-K, Suh Y-H (2006) Phosphorylation of amyloid precursor protein (APP) at Thr668 regulates the nuclear translocation of the APP intracellular domain and induces neurodegeneration. Mol Cell Biol 26:4327-4338
Chaturvedi et al., Nucl. Acids Res. 24:2318-23, 1996
Chothia et al, Nature 342: 877-83, 1989
Chothia et al. J. Mol. Biol. 186: 651, 1985
Clackson, et al, Nature 352: 624-8, 1991
Colcher et al, Ann NY Acad Sci 880: 263-80, 1999
Cole et al, Proc Natl Acad Sci USA 80: 2026-30, 1983
Cole et al., Monoclonal Antibodies and Cancer Therapy, Alan Liss, pp. 77-96, 1985
Dellu et al, Brain Res. 588: 132-9, 1992
Devereux et al, Nucleic Acids Research 12: 387, 1984
Dolev and Michaelson, Proc Natl Acad Sci USA 101:13909-14, 2004
Edman el al, Acta Chem. Scand. 4: 283-93, 1950
Ennaceur & Delacour, Behav Brain Res 31: 47-59, 1988
Ferguson B, Matyszak M K, Esiri M M, Perry V H (1997) Axonal damage in acute multiple sclerosis lesions. Brain 120 (Pt 3:393-399
Gurney, M. E., Pu, H., Chiu, A. Y. et al. (1994) Motor neuron degeneration in mice that express a human Cu,Zn superoxide dismutase mutation. Science, 264, 1772-1775.
Iwata et al, Nature Med 6: 143-50, 2000
Jones et al, Nature, 321: 522, 1986
Kawarabayashi T, Shoji M, Harigaya Y, Yamaguchi H, Hirai S (1991) Expression of APP in the early stage of brain damage. Brain Res 563:334-338
Kim, H. S., Kim, E. M., Lee, J. P. et al. (2003) C-terminal fragments of amyloid precursor protein exert neurotoxicity by inducing glycogen synthase kinase-3beta expression. FASEB J, 17, 1951-1953.
Koh, S. H., Kim, Y., Kim, H. Y., Hwang, S., Lee, C. H. and Kim, S. H. (2007) Inhibition of glycogen synthase kinase-3 suppresses the onset of symptoms and disease progression of G93A-SOD1 mouse model of ALS. Exp Neurol, 205, 336-346.
Kohler et al, Nature 256: 495-7, 1975
Koistinen H, Prinjha R, Soden P, Harper A, Banner S J, Pradat P-F, Loeffler J-P, Dingwall C (2006) Elevated levels of amyloid precursor protein in muscle of patients with amyotrophic lateral sclerosis and a mouse model of the disease. Muscle Nerve 34:444-450
Kozbor et al, Immunol Today 4: 72, 1983
Lee M-S, Kao S-C, Lemere C A, Xia W, Tseng H-C, Zhou Y, Neve R, Ahlijanian M K, Tsai L-H (2003) APP processing is regulated by cytoplasmic phosphorylation. J Cell Biol 163:83-95
Li Q-X, Mok S S, Laughton K M, McLean C a, Volitakis I, Cherny R a, Cheung N S, White A R, Masters C L (2006) Overexpression of Abeta is associated with acceleration of onset of motor impairment and superoxide dismutase 1 aggregation in an amyotrophic lateral sclerosis mouse model. Aging Cell 5:153-165

Marks et al, J Mol Biol 222: 581-97, 1991
Morrison and Oi, Adv Immunol. 44: 65, 1988
Morrison et al, Proc Natl Acad Sci USA 81: 6801, 1984
Narang et al, Meth. Enzymol. 68:90, 1979
Niwa et al, Cell 99:691-702, 1999
Novotny and Haber, Proc Natl Acad Sci USA 82: 4592, 1985
Ozaki, T., Li, Y., Kikuchi, H., Tomita, T., Iwatsubo, T. and Nakagawara, A. (2006) The intracellular domain of the amyloid precursor protein (AICD) enhances the p53-mediated apoptosis. *Biochem Biophys Res Commun*, 351, 57-63.
Padlan, Molec Immunol 28: 489, 1991
Pardridge, Bioengineered Bugs, 1: 231-4, 2010b
Pardridge, J Drug Targeting 18: 157-67, 2010a
Perry at al, Drugs R&D 9: 385-96, 2008
Peyrottes et al, Nucl. Acids Res. 24:1841-8, 1996
Reiter, Clin Cancer Res 2: 245-52, 1996
Riechmann et al, Nature 332: 323, 1988
Ranganathan, S. and Bowser, R. (2010) p53 and Cell Cycle Proteins Participate in Spinal Motor Neuron Cell Death in ALS. Open Pathol J, 4, 11-22.
Sasaki S, Iwata M (1999) Immunoreactivity of beta-amyloid precursor protein in amyotrophic lateral sclerosis. Acta Neuropathol 97:463-468
Smith et al, J Exp Med 185: 1413-22, 1997
Sold C, Garcia-Ladona F J, Sarasa M, Mengod G, Probst A, Palacios G, Palacios J M (1993) Beta APP gene expression is increased in the rat brain after motor neuron axotomy. Eur J Neurosci 5:795-808
Verhoeyen et al, Science 239: 1539, 1988
Xie Y Y, Yao Z B, Wu W T (2000) Survival of motor neurons and expression of beta-amyloid protein in the aged rat spinal cord. Neuroreport 11:697-700
Xu et al, Cellular Immunol 200: 16-26, 2000
Yeh et al, Int J Cancer 29: 269-75, 1982
Yeh et al, Proc Natl Acad Sci USA 76: 2927-31, 1976
Yoon E J, Park H J, Kim G Y, Cho H M, Choi J H, Park H Y, Jang J Y, Rhim H S, Kang S M (2009) Intracellular amyloid beta interacts with SOD1 and impairs the enzymatic activity of SOD1: implications for the pathogenesis of amyotrophic lateral sclerosis. Exp Mol Med 41:611-617
Yu et al, *Sci. Transl. Med.*, 3(84ra44):1-8, 2011

What is claimed is:

1. An isolated antibody, comprising a combination of (i) a heavy chain variable region, which comprises a heavy chain Complementarity Determining Regions (CDRs) CDR1 having the amino acid sequence of SEQ ID NO:9, a heavy chain CDR2 having the amino acid sequence of SEQ ID NO:10, and a heavy chain CDR3 having the amino acid sequence of SEQ ID NO:11, or variants of the heavy chain CDR amino acid sequences having 90% or greater, 95% or greater, 98% or greater, or 99% or greater sequence identity thereto, and (ii) a light chain variable region, which comprises a light chain CDR1 having the amino acid sequence of SEQ ID NO:12, a light chain CDR2 having the amino acid sequence of SEQ ID NO:13, and a light chain CDR3 having the amino acid sequence of SEQ ID NO:14, or variants of the light chain CDR amino acid sequences having 90% or greater, 95% or greater, 98% or greater, or 99% or greater sequence identity thereto; or comprising a combination of (i) a heavy chain variable region, which comprises a heavy chain CDR1 having the amino acid sequence of SEQ ID NO:28, a heavy chain CDR2 having the amino acid sequence of SEQ ID NO:29, and a heavy chain CDR3 having the amino acid sequence of SEQ ID NO:30, or variants of the heavy chain CDR amino acid sequences having 90% or greater, 95% or greater, 98% or greater, or 99% or greater sequence identity thereto, and (ii) a light chain variable region, which comprises a light chain CDR1 having the amino acid sequence of SEQ ID NO:31, a light chain CDR2 having the amino acid sequence of SEQ ID NO:32, and a light chain CDR3 having the amino acid sequence of SEQ ID NO:33 or variants of the light chain CDR amino acid sequences having 90% or greater, 95% or greater, 98% or greater, or 99% or greater sequence identity thereto.

2. The antibody of claim 1, which specifically binds to the peptide of SEQ ID NO:17 or SEQ ID NO:18.

3. The antibody of claim 1, which is a humanized antibody.

4. The antibody of claim 3, having an immunoglobulin heavy chain constant domain selected from the group consisting of IgG1, IgG2, IgG3 or IgG4, optionally comprising an S241P mutation IgG4 (Ser241Pro, Kabat numbering system), IgM, and variants thereof having unglycosylated Fc or Fc mutated in amino acid(s) to cause reduced binding to the Fc receptor.

5. The antibody of claim 3, which is Fab, Fab', F(ab)$_2$, scFv, dsFv antibody, or an antibody fragment.

6. The antibody of claim 3, comprising (i) a heavy chain variable region which comprises an amino acid sequence selected from the group consisting of SEQ ID NOs: 35, 37, 39, 41 and 43, and (ii) a light chain variable region which comprises an amino acid sequence selected from the group consisting of SEQ ID NOs: 45, 47, 49 and 51, and variants of (i) and (ii) in which the CDR amino acid sequences each or together have 90% or greater, 95% or greater, 98% or greater, or 99% or greater sequence identity thereto and the framework regions each or in total have 1, 2, 3, 4, 5, 6, 7, 8, 9 or 10 conservative amino acid substitutions.

7. The antibody of claim 1, which is an antibody or a portion/derivative thereof that inhibits cleavage of APP by BACE.

8. The antibody of claim 1, which is an isolated monoclonal antibody, or antigen-binding portion, or fragment thereof.

9. The antibody of claim 1, wherein the antibody has an inhibitory effect on the proteolytic processing of APP by BACE, thereby reducing levels of intracellular or extracellular Aβ by at least 15%.

10. The antibody of claim 1, which is an antibody that is de-immunized.

11. The antibody of claim 1, which is an antibody that is a multi-specific antibody, such as a bispecific antibody further comprising a second antibody binding specificity which confers the ability of the bispecific antibody to cross the blood-brain barrier.

12. The antibody of claim 11, wherein the first and second antibody binding specificities are provided by chemically linking a first antibody, or fragment thereof, to a second antibody, or fragment thereof.

13. The antibody of claim 12, wherein the first and second antibodies are monoclonal antibodies.

14. The antibody of claim 13, which is an F(ab')$_2$.

15. The antibody of claim 14, which is a single chain Fv heterobispecific dimer.

16. An antibody complex, comprising an antibody of claim 1, or an antibody fragment thereof, and a sialic acid-containing molecule conjugated thereto.

17. The antibody of claim 1, which is a monoclonal antibody that inhibits cleavage of APP by BACE, wherein said antibody comprises the amino acid sequence of F5.100 or F5.87.

18. A pharmaceutical composition, comprising the antibody of claim 1, or active fragment or complex thereof in a therapeutically effective amount, and a pharmaceutically acceptable carrier, a diluent, and/or an excipient.

19. The pharmaceutical composition of claim 18 suitable for administration, in a dosage suitable for treatment and/or delaying development of a disease that is susceptible to inhibiting of APP cleavage by BACE.

20. A method for treating a disease or condition associated with increased concentration of Aβ in the brain of a subject in need thereof, comprising administering the antibody of claim 1 in a therapeutically effective amount to the subject.

21. The method of claim 20, wherein the disease or condition is Alzheimer's disease, mild cognitive impairment, Down's syndrome, or hereditary cerebral hemorrhage with amyloidosis (Dutch type).

22. A method of treating Alzheimer's disease, comprising administering to a patient having or suspected of having Alzheimer's disease the antibody of claim 1.

23. A method of treating amyotrophic lateral sclerosis (ALS), comprising administering to a patient having or suspected of having ALS the antibody of claim 1.

24. A method for reducing the plaque load in the brain of a subject suffering from a disease or condition associated with increased concentration of Aβ in the brain, comprising administering the antibody of claim 1 in a therapeutically effective amount to the subject.

25. A method of inhibiting deposition of Aβ, comprising administering the antibody of claim 1 or active fragment thereof in a therapeutically effective amount to the subject.

26. A method for decreasing the total amount of soluble Aβ in the brain of a subject suffering from a disease or condition associated with increased concentration of Aβ in the brain, comprising administering the antibody of claim 1 in a therapeutically effective amount to the subject.

27. A method for retaining or increasing cognitive memory capacity in a subject suffering from a disease or condition associated with increased concentration of Aβ in the brain, comprising administering the antibody of claim 1 in a therapeutically effective amount to the subject.

28. A method for treating and/or delay development of a disease that is susceptible to inhibiting APP cleavage by BACE, comprising administering to a patient in need thereof the antibody of claim 1.

29. An isolated antibody, comprising a combination of a heavy chain variable region (VH) and a light chain variable region (VL) selected from the group consisting of:

VH1 of SEQ ID NO:35 and VL1 of SEQ ID NO:45;
VH1 of SEQ ID NO:35 and VL2 of SEQ ID NO: 47;
VH1 of SEQ ID NO:35 and VL3 of SEQ ID NO:49;
VH1 of SEQ ID NO:35 and VL4 of SEQ ID NO:51;
VH2 of SEQ ID NO:37 and VL1 of SEQ ID NO:45;
VH2 of SEQ ID NO:37 and VL2 of SEQ ID NO:47;
VH2 of SEQ ID NO:37 and VL3 of SEQ ID NO:49
VH2 of SEQ ID NO:37 and VL4 of SEQ ID NO:51;
VH3 of SEQ ID NO:39 and VL1 of SEQ ID NO:45;
VH3 of SEQ ID NO:39 and VL2 of SEQ ID NO:47;
VH3 of SEQ ID NO:39 and VL3 of SEQ ID NO:49;
VH3 of SEQ ID NO:39 and VL4 of SEQ ID NO:51;
VH4 of SEQ ID NO:41 and VL1 of SEQ ID NO:45;
VH4 of SEQ ID NO:41 and VL2 of SEQ ID NO:47;
VH4 of SEQ ID NO:41 and VL3 of SEQ ID NO:49;
VH4 of SEQ ID NO:41 and VL4 of SEQ ID NO:51;
VH5 of SEQ ID NO:43 and VL1 of SEQ ID NO:45;
VH5 of SEQ ID NO:43 and VL2 of SEQ ID NO:47;
VH5 of SEQ ID NO:43 and VL3 of SEQ ID NO:49; and
VH5 of SEQ ID NO:43 and VL4 of SEQ ID NO:51.

* * * * *

SEQUENCE LISTING

```
<160> NUMBER OF SEQ ID NOS: 57

<210> SEQ ID NO 1
<211> LENGTH: 1377
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: F5.100 H chain

<400> SEQUENCE: 1
atgggaagga gctggatctt tctcttcctc ctgtcaggaa ctgcaggcgt ccactctgag     60
gtccagcttc agcagtcagg acctgagctg gtgaaacctg gggcctcagt gaagatatcc    120
tgcaaggctt ctggatacac attcactgac tacaacatgc actgggtgaa gcagagccat    180
ggaaagagac ttgagtggat tggatatatt tatcctcaca atggtggtac tggctacaac    240
cagaggttca agagcaaggc cacattgact gtagacaagt cctccagcac agcctacatg    300
gagctccgca gcctgacatc tgaggactct gcagtctatt actgtgcaag acccgggacg    360
gaggcttact ggggccaagg gactctggtc actgtctctg cagccaaaac gacacccca     420 tctgtctatc cactggcccc tggatctgct gcccaaacta actccatggt gaccctggga    480
tgcctggtca agggctattt ccctgagcca gtgacagtga cctggaactc tggatccctg    540
tccagcggtg tgcacacctt cccagctgtc ctgcagtctg acctctacac tctgagcagc    600
tcagtgactg tcccctccag cacctggccc agcgagaccg tcacctgcaa cgttgcccac    660
ccggccagca gcaccaaggt ggacaagaaa attgtgccca gggattgtgg ttgtaagcct    720
tgcatatgta cagtcccaga agtatcatct gtcttcatct tccccccaaa gcccaaggat    780
gtgctcacca ttactctgac tcctaaggtc acgtgtgttg tggtagacat cagcaaggat    840
gatcccgagg tccagttcag ctggtttgta gatgatgtgg aggtgcacac agctcagacg    900
caaccccggg aggagcagtt caacagcact ttccgctcag tcagtgaact tcccatcatg    960
caccaggact ggctcaatgg caaggagttc aaatgcaggg tcaacagtgc agcttttcct   1020
gcccccatcg agaaaaccat ctccaaaacc aagggcagac cgaaggctcc acaggtgtac   1080
```

```
accattccac ctcccaagga gcagatggcc aaggataaag tcagtctgac ctgcatgata    1140
acagacttct tccctgaaga cattactgtg gagtggcagt ggaatgggca gccagcggag    1200
aactacaaga acactcagcc catcatggac acagatggct cttacttcgt ctacagcaag    1260
ctcaatgtgc agaagagcaa ctgggaggca ggaaatactt tcacctgctc tgtgttacac    1320
gagggcctgc acaaccacca tactgagaag agcctctccc actctcctgg taaatga      1377
```

<210> SEQ ID NO 2
<211> LENGTH: 458
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: F5.100 H chain

<400> SEQUENCE: 2

```
Met Gly Arg Ser Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Val Lys Ile Ser Cys Lys Ala Ser Gly Tyr Thr Phe
        35                  40                  45

Thr Asp Tyr Asn Met His Trp Val Lys Gln Ser His Gly Lys Arg Leu
    50                  55                  60

Glu Trp Ile Gly Tyr Ile Tyr Pro His Asn Gly Gly Thr Gly Tyr Asn
65                  70                  75                  80

Gln Arg Phe Lys Ser Lys Ala Thr Leu Thr Val Asp Lys Ser Ser Ser
                85                  90                  95

Thr Ala Tyr Met Glu Leu Arg Ser Leu Thr Ser Glu Asp Ser Ala Val
            100                 105                 110

Tyr Tyr Cys Ala Arg Pro Gly Thr Glu Ala Tyr Trp Gly Gln Gly Thr
        115                 120                 125

Leu Val Thr Val Ser Ala Ala Lys Thr Thr Pro Pro Ser Val Tyr Pro
130                 135                 140

Leu Ala Pro Gly Ser Ala Ala Gln Thr Asn Ser Met Val Thr Leu Gly
145                 150                 155                 160

Cys Leu Val Lys Gly Tyr Phe Pro Glu Pro Val Thr Val Thr Trp Asn
                165                 170                 175

Ser Gly Ser Leu Ser Ser Gly Val His Thr Phe Pro Ala Val Leu Gln
            180                 185                 190

Ser Asp Leu Tyr Thr Leu Ser Ser Ser Val Thr Val Pro Ser Ser Thr
        195                 200                 205

Trp Pro Ser Glu Thr Val Thr Cys Asn Val Ala His Pro Ala Ser Ser
    210                 215                 220

Thr Lys Val Asp Lys Lys Ile Val Pro Arg Asp Cys Gly Cys Lys Pro
225                 230                 235                 240

Cys Ile Cys Thr Val Pro Glu Val Ser Ser Val Phe Ile Phe Pro Pro
                245                 250                 255

Lys Pro Lys Asp Val Leu Thr Ile Thr Leu Thr Pro Lys Val Thr Cys
            260                 265                 270

Val Val Val Asp Ile Ser Lys Asp Asp Pro Glu Val Gln Phe Ser Trp
        275                 280                 285

Phe Val Asp Asp Val Glu Val His Thr Ala Gln Thr Gln Pro Arg Glu
    290                 295                 300
```

Glu Gln Phe Asn Ser Thr Phe Arg Ser Val Ser Glu Leu Pro Ile Met
305                 310                 315                 320

His Gln Asp Trp Leu Asn Gly Lys Glu Phe Lys Cys Arg Val Asn Ser
            325                 330                 335

Ala Ala Phe Pro Ala Pro Ile Glu Lys Thr Ile Ser Lys Thr Lys Gly
        340                 345                 350

Arg Pro Lys Ala Pro Gln Val Tyr Thr Ile Pro Pro Lys Glu Gln
    355                 360                 365

Met Ala Lys Asp Lys Val Ser Leu Thr Cys Met Ile Thr Asp Phe Phe
370                 375                 380

Pro Glu Asp Ile Thr Val Glu Trp Gln Trp Asn Gly Gln Pro Ala Glu
385                 390                 395                 400

Asn Tyr Lys Asn Thr Gln Pro Ile Met Asp Thr Asp Gly Ser Tyr Phe
                405                 410                 415

Val Tyr Ser Lys Leu Asn Val Gln Lys Ser Asn Trp Glu Ala Gly Asn
                420                 425                 430

Thr Phe Thr Cys Ser Val Leu His Glu Gly Leu His Asn His His Thr
            435                 440                 445

Glu Lys Ser Leu Ser His Ser Pro Gly Lys
    450                 455

<210> SEQ ID NO 3
<211> LENGTH: 705
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: F5.100 L chain

<400> SEQUENCE: 3
atggagtcac agactcaggt ctttgtatac atgttgctgt ggttgtctgg tgttgatgga      60
gacattgtga tgacccagtc tcaaaaattc atgtccacat cagtaggaga cagggtcagc     120
gtcacctgca aggccagtca gaatgtgggt actaatgtag cctggtatca acagaaacca     180
gggcaatctc ctaaaccact gatttactcg gcatcctacc ggtacagtgg agtccctgat     240
cgcttcacag gcagtggatc tgggacagat ttcactctca ccatcagcaa tgtgcagtct     300
gaagacttgg cagagtattt ctgtcagcaa tttaacagct atcctctcac gttcggtgct     360
gggaccaagc tggagctgaa acgggctgat gctgcaccaa ctgtatccat cttcccacca     420
tccagtgagc agttaacatc tggaggtgcc tcagtcgtgt gcttcttgaa caacttctac     480
cccaaagaca tcaatgtcaa gtggaagatt gatggcagtg aacgacaaaa tggcgtcctg     540
aacagttgga ctgatcagga cagcaaagac agcacctaca gcatgagcag caccctcacg     600
ttgaccaagg acgagtatga acgacataac agctatacct gtgaggccac tcacaagaca     660
tcaacttcac ccattgtcaa gagcttcaac aggaatgagt gttag                     705

<210> SEQ ID NO 4
<211> LENGTH: 234
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: F5.100 L chain

<400> SEQUENCE: 4

```
Met Glu Ser Gln Thr Gln Val Phe Val Tyr Met Leu Leu Trp Leu Ser
1               5                   10                  15

Gly Val Asp Gly Asp Ile Val Met Thr Gln Ser Gln Lys Phe Met Ser
            20                  25                  30

Thr Ser Val Gly Asp Arg Val Ser Val Thr Cys Lys Ala Ser Gln Asn
        35                  40                  45

Val Gly Thr Asn Val Ala Trp Tyr Gln Gln Lys Pro Gly Gln Ser Pro
    50                  55                  60

Lys Pro Leu Ile Tyr Ser Ala Ser Tyr Arg Tyr Ser Gly Val Pro Asp
65                  70                  75                  80

Arg Phe Thr Gly Ser Gly Ser Gly Thr Asp Phe Thr Leu Thr Ile Ser
                85                  90                  95

Asn Val Gln Ser Glu Asp Leu Ala Glu Tyr Phe Cys Gln Gln Phe Asn
            100                 105                 110

Ser Tyr Pro Leu Thr Phe Gly Ala Gly Thr Lys Leu Glu Leu Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230
```

<210> SEQ ID NO 5
<211> LENGTH: 345
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: F5.100 VH

<400> SEQUENCE: 5

```
gaggtccagc ttcagcagtc aggacctgag ctggtgaaac ctggggcctc agtgaagata      60
tcctgcaagg cttctggata cacattcact gactacaaca tgcactgggt gaagcagagc     120
catggaaaga gacttgagtg gattggatat atttatcctc acaatggtgg tactggctac     180
aaccagaggt tcaagagcaa ggccacattg actgtagaca gtcctccag cacagcctac      240
atggagctcc gcagcctgac atctgaggac tctgcagtct attactgtgc aagacccggg     300
acggaggctt actggggcca aggactctg gtcactgtct ctgca                      345
```

<210> SEQ ID NO 6
<211> LENGTH: 115
<212> TYPE: PRT
<213> ORGANISM: Artificial Sequence
<220> FEATURE:
<223> OTHER INFORMATION: Synthetic

```
<220> FEATURE:
<221> NAME/KEY: misc_feature
<223> OTHER INFORMATION: F5.100 VH

<400> SEQUENCE: 6

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Asn Met His Trp Val Lys Gln Ser His Gly Lys Arg Leu Glu Trp Ile
        35                  40                  45

Gly Tyr Ile Tyr Pro His Asn Gly Gly Thr Gly Tyr Asn Gln Arg Phe
    50                  55                  60

Lys Ser Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Pro Gly Thr Glu Ala Tyr Trp Gly Gln Gly Thr Leu Val Thr
            100                 105                 110

Val Ser Ala
        115

<210> SEQ ID NO 7
<211> LENGTH: 321
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: F5.100 VL

<400> SEQUENCE: 7
gacattgtga tgacccagtc tcaaaaattc atgtccacat cagtaggaga cagggtcagc     60
gtcacctgca aggccagtca gaatgtgggt actaatgtag cctggtatca acagaaacca   120
gggcaatctc ctaaaccact gatttactcg gcatcctacc ggtacagtgg agtccctgat   180
cgcttcacag gcagtggatc tgggacagat ttcactctca ccatcagcaa tgtgcagtct   240
gaagacttgg cagagtattt ctgtcagcaa tttaacagct atcctctcac gttcggtgct   300
gggaccaagc tggagctgaa a                                             321

<210> SEQ ID NO 8
<211> LENGTH: 107
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: F5.100 VL

<400> SEQUENCE: 8

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Pro Leu Ile
        35                  40                  45

Tyr Ser Ala Ser Tyr Arg Tyr Ser Gly Val Pro Asp Arg Phe Thr Gly
    50                  55                  60
```

```
Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Phe Asn Ser Tyr Pro Leu
                85                  90                  95

Thr Phe Gly Ala Gly Thr Lys Leu Glu Leu Lys
            100                 105

<210> SEQ ID NO 9
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: F5.100 VH CDR1

<400> SEQUENCE: 9

Asp Tyr Asn Met His
1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: F5.100 VH CDR2

<400> SEQUENCE: 10

Tyr Ile Tyr Pro His Asn Gly Gly Thr Gly Tyr Asn Gln Arg Phe Lys
1               5                   10                  15
Ser

<210> SEQ ID NO 11
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: F5.100 VH CDR3

<400> SEQUENCE: 11

Pro Gly Thr Glu Ala Tyr
1               5

<210> SEQ ID NO 12
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: F5.100 VL CDR1

<400> SEQUENCE: 12

Lys Ala Ser Gln Asn Val Gly Thr Asn Val Ala
1               5                   10

<210> SEQ ID NO 13
<211> LENGTH: 7
```

```
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: F5.100 VL CDR2

<400> SEQUENCE: 13

Ser Ala Ser Tyr Arg Tyr Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: F5.100 VL CDR3

<400> SEQUENCE: 14

Gln Gln Phe Asn Ser Tyr Pro Leu Thr
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: half Swedish MAP peptide

<400> SEQUENCE: 15

Ile Ser Glu Val Lys Leu Asp Ala
1               5

<210> SEQ ID NO 16
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: another MAP peptide

<400> SEQUENCE: 16

Ile Ser Glu Val Lys Leu Asp Ala Lys Leu Asp Ala
1               5                   10

<210> SEQ ID NO 17
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Swedish MAP peptide

<400> SEQUENCE: 17

Ile Ser Glu Val Asn Leu Asp Ala
1               5

<210> SEQ ID NO 18
```

```
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: wild type MAP peptide

<400> SEQUENCE: 18

Ile Ser Glu Val Lys Met Asp Ala
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic

<400> SEQUENCE: 19

Glu Val Gln Leu Gln
1               5

<210> SEQ ID NO 20
<211> LENGTH: 18
<212> TYPE: PRT
<213> ORGANISM: Artificial Sequence
<220> FEATURE:
<223> OTHER INFORMATION: Synthetic

<400> SEQUENCE: 20

Val Gln Leu Gln Gln Ser Gly Pro Glu Leu Val Lys Pro Gly Ala Ser
1               5                   10                  15

Val Lys

<210> SEQ ID NO 21
<211> LENGTH: 18
<212> TYPE: PRT
<213> ORGANISM: Artificial Sequence
<220> FEATURE:
<223> OTHER INFORMATION: Synthetic

<400> SEQUENCE: 21

Asp Ile Val Met Thr Gln Ser Gln Lys Phe Met Ser Thr Ser Val Gly
1               5                   10                  15

Asp Arg

<210> SEQ ID NO 22
<211> LENGTH: 19
<212> TYPE: PRT
<213> ORGANISM: Artificial Sequence
<220> FEATURE:
<223> OTHER INFORMATION: Synthetic

<400> SEQUENCE: 22

Gly Asp Ile Val Met Thr Gln Ser Gln Lys Phe Met Ser Thr Ser Val
1               5                   10                  15

Gly Asp Arg

<210> SEQ ID NO 23
<211> LENGTH: 5
<212> TYPE: PRT
<213> ORGANISM: Artificial Sequence
<220> FEATURE:
<223> OTHER INFORMATION: Synthetic
```

<400> SEQUENCE: 23

Asp Ile Val Met Thr
1               5

<210> SEQ ID NO 24
<211> LENGTH: 341
<212> TYPE: PRT
<213> ORGANISM: Artificial Sequence
<220> FEATURE:
<223> OTHER INFORMATION: Synthetic

<400> SEQUENCE: 24

Val His Ser Glu Val Gln Leu Gln Gln Ser Gly Pro Glu Leu Val Lys
1               5                   10                  15

Pro Gly Ala Ser Val Lys Ile Ser Cys Lys Ala Ser Gly Tyr Thr Phe
            20                  25                  30

Thr Asp Tyr Asn Met His Trp Val Lys Arg Leu Glu Trp Ile Gly Tyr
        35                  40                  45

Ile Tyr Pro His Asn Gly Gly Thr Gly Tyr Asn Gln Arg Lys Ser Lys
    50                  55                  60

Ala Thr Leu Thr Val Asp Lys Ser Ser Thr Ala Tyr Met Glu Leu
65                  70                  75                  80

Arg Ser Leu Thr Ser Glu Asp Ser Ala Val Tyr Tyr Cys Ala Arg Pro
                85                  90                  95

Gly Thr Glu Ala Tyr Trp Gly Gln Gly Thr Leu Val Thr Val Ser Ala
            100                 105                 110

Ala Lys Thr Thr Pro Pro Ser Val Tyr Pro Leu Ala Pro Gly Ser Ala
        115                 120                 125

Ala Gln Thr Asn Ser Met Val Thr Leu Gly Cys Leu Val Lys Gly Tyr
    130                 135                 140

Phe Pro Glu Pro Val Thr Val Thr Trp Asn Ser Gly Ser Leu Ser Ser
145                 150                 155                 160

Gly Val His Thr Phe Pro Ala Val Leu Val Thr Val Pro Ser Ser Thr
                165                 170                 175

Trp Pro Pro Lys Pro Lys Asp Val Leu Thr Ile Thr Leu Thr Pro Lys
            180                 185                 190

Val Thr Cys Val Val Val Asp Ile Ser Lys Asp Asp Pro Glu Val Gln
        195                 200                 205

Phe Ser Trp Phe Val Asp Asp Val Glu Val His Thr Ala Gln Thr Gln
    210                 215                 220

Pro Arg Arg Ser Val Ser Glu Leu Pro Ile Met His Gln Asp Trp Leu
225                 230                 235                 240

Asn Gly Lys Glu Phe Lys Cys Arg Val Asn Ser Ala Ala Phe Pro Ala
                245                 250                 255

Pro Ile Glu Lys Thr Ile Ser Lys Thr Lys Gly Arg Pro Lys Ala Pro
            260                 265                 270

Gln Val Tyr Thr Ile Pro Pro Lys Glu Gln Met Ala Lys Asp Lys
    275                 280                 285

Val Ser Leu Gln Trp Asn Gly Gln Pro Ala Glu Asn Tyr Lys Asn Thr
290                 295                 300

Gln Pro Ile Met Asp Thr Asp Gly Ser Tyr Phe Val Tyr Ser Lys Leu
305                 310                 315                 320

Asn Val Gln Lys Ser Asn Trp Glu Ala Gly Asn Thr Phe Thr Cys Ser
                325                 330                 335

Val Leu His Glu Gly
            340

<210> SEQ ID NO 25
<211> LENGTH: 215
<212> TYPE: PRT
<213> ORGANISM: Artificial Sequence
<220> FEATURE:
<223> OTHER INFORMATION: Synthetic

<400> SEQUENCE: 25

Gly Asp Ile Val Met Thr Gln Ser Gln Lys Phe Met Ser Thr Ser Val
1               5                   10                  15

Gly Asp Arg Val Ser Val Thr Cys Lys Ala Ser Gln Asn Val Gly Thr
            20                  25                  30

Asn Val Ala Trp Tyr Gln Gln Lys Pro Gly Gln Ser Pro Lys Pro Leu
        35                  40                  45

Ile Tyr Ser Ala Ser Tyr Arg Tyr Ser Gly Val Pro Asp Arg Phe Thr
    50                  55                  60

Gly Ser Gly Ser Gly Thr Asp Phe Thr Leu Thr Ile Ser Asn Val Gln
65                  70                  75                  80

Ser Glu Asp Leu Ala Glu Tyr Phe Cys Gln Gln Phe Asn Ser Tyr Pro
                85                  90                  95

Leu Thr Phe Gly Ala Gly Thr Lys Leu Glu Leu Lys Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
    130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
    210                 215

<210> SEQ ID NO 26
<211> LENGTH: 117
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: F5.87 VH

<400> SEQUENCE: 26

Glu Val Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asn Ala
            20                  25                  30

Trp Met Asp Trp Val Arg Gln Ser Pro Glu Lys Gly Leu Glu Trp Val
        35                  40                  45

Ala Glu Ile Arg Ser Lys Ala Asn Asn His Ala Thr Tyr Tyr Gly Glu
    50                  55                  60

```
Ser Val Lys Gly Arg Phe Thr Ile Ser Arg Asp Asp Ser Lys Ser Ser
 65                  70                  75                  80

Val Tyr Leu Gln Met Asn Ser Leu Arg Ala Glu Asp Thr Gly Ile Tyr
                 85                  90                  95

Tyr Cys Thr Ala Thr Val Arg Gly Gly Tyr Trp Gly Gln Gly Thr Thr
            100                 105                 110

Leu Thr Val Ser Ser
        115

<210> SEQ ID NO 27
<211> LENGTH: 107
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: F5.87 VL

<400> SEQUENCE: 27

Asp Ile Lys Met Thr Gln Ser Pro Ser Ser Met Tyr Ala Ser Leu Gly
 1               5                  10                  15

Glu Arg Val Thr Ile Thr Cys Lys Ala Ser Gln Asp Ile Asn Ser Tyr
                 20                  25                  30

Leu Ser Trp Phe Gln Gln Lys Pro Gly Lys Ser Pro Lys Thr Leu Ile
             35                  40                  45

Tyr Arg Ala Asn Arg Leu Val Asp Gly Val Pro Ser Arg Phe Ser Gly
         50                  55                  60

Ser Gly Ser Gly Gln Asp Tyr Ser Leu Thr Ile Ser Ser Leu Glu Tyr
 65                  70                  75                  80

Glu Asp Met Gly Ile Tyr Tyr Cys Leu Gln Tyr Asp Glu Tyr Pro Tyr
                 85                  90                  95

Thr Phe Gly Gly Gly Thr Lys Leu Glu Ile Lys
            100                 105

<210> SEQ ID NO 28
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: F5.87 VH CDR1

<400> SEQUENCE: 28

Asn Ala Trp Met Asp
 1               5

<210> SEQ ID NO 29
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: F5.87 VH CDR2

<400> SEQUENCE: 29

Glu Ile Arg Ser Lys Ala Asn Asn His Ala Thr Tyr Tyr Gly Glu Ser
 1               5                  10                  15
```

Val Lys Gly

<210> SEQ ID NO 30
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: F5.87 VH CDR3

<400> SEQUENCE: 30

Thr Val Arg Gly Gly Tyr
1               5

<210> SEQ ID NO 31
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: F5.87 VL CDR1

<400> SEQUENCE: 31

Lys Ala Ser Gln Asp Ile Asn Ser Tyr Leu Ser
1               5                   10

<210> SEQ ID NO 32
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: F5.87 VL CDR2

<400> SEQUENCE: 32

Arg Ala Asn Arg Leu Val Asp
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: F5.87 VL CDR3

<400> SEQUENCE: 33

Leu Gln Tyr Asp Glu Tyr Pro Tyr Thr
1               5

<210> SEQ ID NO 34
<211> LENGTH: 345
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: VH1

<400> SEQUENCE: 34

```
gaggtccagc ttgtgcagtc aggacctgag ctgaagaaac ctggggcctc agtgaagata    60
tcctgcaagg cttctggata cacattcact gactacaaca tgcactgggt gaagcaggcc   120
catggaaagg gacttgagtg gattggatat atttatcctc acaatggtgg tactggctac   180
aaccagaggt tcaagagcaa ggccacattg accgtagaca agtccaccag cacagcctac   240
atggagctcc gcagcctgac atctgaggac tctgcagtct attactgtgc aagacccggg   300
acggaggctt actggggcca aggactctg gtcactgtct cttcc                    345
```

<210> SEQ ID NO 35
<211> LENGTH: 115
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: VH1

<400> SEQUENCE: 35

```
Glu Val Gln Leu Val Gln Ser Gly Pro Glu Leu Lys Lys Pro Gly Ala
1               5                   10                  15

Ser Val Lys Ile Ser Cys Lys Ala Ser Gly Tyr Thr Phe Thr Asp Tyr
            20                  25                  30

Asn Met His Trp Val Lys Gln Ala His Gly Lys Gly Leu Glu Trp Ile
        35                  40                  45

Gly Tyr Ile Tyr Pro His Asn Gly Gly Thr Gly Tyr Asn Gln Arg Phe
    50                  55                  60

Lys Ser Lys Ala Thr Leu Thr Val Asp Lys Ser Thr Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Pro Gly Thr Glu Ala Tyr Trp Gly Gln Gly Thr Leu Val Thr
            100                 105                 110

Val Ser Ser
        115
```

<210> SEQ ID NO 36
<211> LENGTH: 345
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: VH2

<400> SEQUENCE: 36

```
gaggtccagc ttgtgcagtc aggagctgag gtgaagaaac ctggggcctc agtgaagata    60
tcctgcaagg cttctggata cacattcact gactacaaca tgcactgggt gaagcaggcc   120
catggaaagg gacttgagtg gattggatat atttatcctc acaatggtgg tactggctac   180
aaccagaggt tcaagagcaa ggccacattg accgtagaca agtccaccag cacagcctac   240
atggagctct ccagcctgcg atctgaggac tctgcagtct attactgtgc aagacccggg   300
acggaggctt actggggcca aggactctg gtcactgtct cttcc                    345
```

<210> SEQ ID NO 37
<211> LENGTH: 115
<212> TYPE: PRT
<213> ORGANISM: Artificial Sequence

```
<220> FEATURE:
<223> OTHER INFORMATION: Synthetic
<220> FEATURE:
<221> NAME/KEY: misc_feature
<223> OTHER INFORMATION: VH2

<400> SEQUENCE: 37

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Met His Trp Val Lys Gln Ala His Gly Lys Gly Leu Glu Trp Ile
        35                  40                  45

Gly Tyr Ile Tyr Pro His Asn Gly Gly Thr Gly Tyr Asn Gln Arg Phe
    50                  55                  60

Lys Ser Lys Ala Thr Leu Thr Val Asp Lys Ser Thr Ser Thr Ala Tyr
65                  70                  75                  80

Met Glu Leu Ser Ser Leu Arg Ser Glu Asp Ser Ala Val Tyr Tyr Cys
                85                  90                  95

Ala Arg Pro Gly Thr Glu Ala Tyr Trp Gly Gln Gly Thr Leu Val Thr
            100                 105                 110

Val Ser Ser
        115

<210> SEQ ID NO 38
<211> LENGTH: 345
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: VH3

<400> SEQUENCE: 38
gaggtccagc ttgtgcagtc aggagctgag gtgaagaaac ctggggcctc agtgaagata      60
tcctgcaagg cttctggata cacattcact gactacaaca tgcactgggt gaagcaggcc    120
cctggaaagg gacttgagtg gattggatat atttatcctc acaatggtgg tactggctac    180
aaccagaggt tcaagagcaa ggccacattg accgtagaca gtccaccag cacagcctac     240 atggagctct ccagcctgcg atctgaggac actgcagtct attactgtgc aagacccggg    300
acggaggctt actggggcca aggactctg gtcactgtct cttcc                     345

<210> SEQ ID NO 39
<211> LENGTH: 115
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: VH3

<400> SEQUENCE: 39

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Met His Trp Val Lys Gln Ala Pro Gly Lys Gly Leu Glu Trp Ile
        35                  40                  45
```

```
Gly Tyr Ile Tyr Pro His Asn Gly Gly Thr Gly Tyr Asn Gln Arg Phe
    50                  55                  60

Lys Ser Lys Ala Thr Leu Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Pro Gly Thr Glu Ala Tyr Trp Gly Gln Gly Thr Leu Val Thr
                100                 105                 110

Val Ser Ser
        115

<210> SEQ ID NO 40
<211> LENGTH: 345
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: VH4

<400> SEQUENCE: 40
gaggtccagc ttgtgcagtc aggagctgag gtgaagaaac ctggggcctc agtgaagata      60
tcctgcaagg cttctggata cacattcact gactacaaca tgcactgggt gaggcaggcc    120
cctggaaagg gacttgagtg gattggatat atttatcctc acaatggtgg tactggctac    180
aaccagaggt tcaagagcaa ggccacattg accgtagaca gtccaccag cacagcctac     240 atggagctct ccagcctgcg atctgaggac actgcagtct attactgtgc aagacccggg    300
acggaggctt actggggcca aggactctg gtcactgtct cttcc                     345

<210> SEQ ID NO 41
<211> LENGTH: 115
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: VH4

<400> SEQUENCE: 41

Glu Val Gln Leu Val Gln Ser Gly Ala Glu Val Lys Lys Pro Gly Ala
  1               5                  10                  15

Ser Val Lys Ile Ser Cys Lys Ala Ser Gly Tyr Thr Phe Thr Asp Tyr
             20                  25                  30

Asn Met His Trp Val Arg Gln Ala Pro Gly Lys Gly Leu Glu Trp Ile
         35                  40                  45

Gly Tyr Ile Tyr Pro His Asn Gly Gly Thr Gly Tyr Asn Gln Arg Phe
    50                  55                  60

Lys Ser Lys Ala Thr Leu Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Pro Gly Thr Glu Ala Tyr Trp Gly Gln Gly Thr Leu Val Thr
                100                 105                 110

Val Ser Ser
        115

<210> SEQ ID NO 42
```

<211> LENGTH: 345
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: VH5

<400> SEQUENCE: 42

```
gaggtccagc ttgtgcagtc aggagctgag gtgaagaaac ctggggcctc agtgaaggtg      60
tcctgcaagg cttctggata cacattcact gactacaaca tgcactgggt gaggcaggcc     120
cctggaaagg gacttgagtg gattggatat atttatcctc acaatggtgg tactggctac     180
aaccagaggt tcaagagcaa ggccacaatc accgtagaca gtccaccag cacagcctac      240
atggagctct ccagcctgcg atctgaggac actgcagtct attactgtgc aagacccggg     300
acggaggctt actggggcca aggactctg gtcactgtct cttcc                      345
```

<210> SEQ ID NO 43
<211> LENGTH: 115
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: VH5

<400> SEQUENCE: 43

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Lys Gly Leu Glu Trp Ile
        35                  40                  45

Gly Tyr Ile Tyr Pro His Asn Gly Gly Thr Gly Tyr Asn Gln Arg Phe
    50                  55                  60

Lys Ser Lys Ala Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Gly Thr Glu Ala Tyr Trp Gly Gln Gly Thr Leu Val Thr
            100                 105                 110

Val Ser Ser
        115
```

<210> SEQ ID NO 44
<211> LENGTH: 321
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: VL1

<400> SEQUENCE: 44

```
gacattgtga tgacccagtc tccatcattc atgtccgcct cagtaggaga cagggtcacc      60
atcacctgca aggccagtca gaatgtgggt actaatgtag cctggtatca acagaaacca     120
gggaaggctc ctaaaccact gatttactcg gcatcctacc ggtacagtgg agtccctgat     180
```

```
cgcttcacag gcagtggatc tgggacagat tcactctca ccatcagctc tctgcagtct    240
gaagacgtgg cagagtattt ctgtcagcaa tttaacagct atcctctcac gttcggtggc    300
gggaccaagg tggagattaa a                                              321
```

<210> SEQ ID NO 45
<211> LENGTH: 107
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: VL1

<400> SEQUENCE: 45

```
Asp Ile Val Met Thr Gln Ser Pro Ser Phe Met Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Pro Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Ser Leu Gln Ser
65                  70                  75                  80

Glu Asp Val Ala Glu Tyr Phe Cys Gln Gln Phe Asn Ser Tyr Pro Leu
                85                  90                  95

Thr Phe Gly Gly Gly Thr Lys Val Glu Ile Lys
            100                 105
```

<210> SEQ ID NO 46
<211> LENGTH: 321
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: VL2

<400> SEQUENCE: 46

```
gacattgtga tgacccagtc tccatcatcc atgtccgcct cagtaggaga cagggtcacc    60
atcacctgca aggccagtca gaatgtgggt actaatgtag cctggtatca acagaaacca    120
gggaaggctc ctaaaccact gatttactcg gcatcctacc ggtacagtgg agtccctgat    180
cgcttcacag gcagtggatc tgggacagat tcactctca ccatcagctc tctgcaggct    240
gaagacgtgg cagagtattt ctgtcagcaa tttaacagct atcctctcac gttcggtggc    300
gggaccaagg tggagattaa a                                              321
```

<210> SEQ ID NO 47
<211> LENGTH: 107
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: VL2

<400> SEQUENCE: 47

```
Asp Ile Val Met Thr Gln Ser Pro Ser Ser Met Ser Ala Ser Val Gly
```

```
1               5                   10                  15
Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Pro Leu Ile
            35                  40                  45

Tyr Ser Ala Ser Tyr Arg Tyr Ser Gly Val Pro Asp Arg Phe Thr Gly
            50                  55                  60

Ser Gly Ser Gly Thr Asp Phe Thr Leu Thr Ile Ser Ser Leu Gln Ala
65                  70                  75                  80

Glu Asp Val Ala Glu Tyr Phe Cys Gln Gln Phe Asn Ser Tyr Pro Leu
                85                  90                  95

Thr Phe Gly Gly Gly Thr Lys Val Glu Ile Lys
            100                 105
```

<210> SEQ ID NO 48
<211> LENGTH: 321
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: VL3

<400> SEQUENCE: 48

```
gacattgtga tgacccagtc tccatcatcc atgtccgcct cagtaggaga cagggtcacc      60
atcacctgca aggccagtca gaatgtgggt actaatgtag cctggtatca acagaaacca     120
gggaaggctc ctaaaccact gatttactcg gcatcctacc ggtacagtgg agtccctgat     180
cgcttcagcg gcagtggatc tgggacagat tcactctca ccatcagctc tctgcaggct     240
gaagacgtgg cagagtattt ctgtcagcaa tttaacagct atcctctcac gttcggtggc     300
gggaccaagg tggagattaa a                                               321
```

<210> SEQ ID NO 49
<211> LENGTH: 107
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: VL3

<400> SEQUENCE: 49

```
Asp Ile Val Met Thr Gln Ser Pro Ser Ser Met Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Pro Leu Ile
            35                  40                  45

Tyr Ser Ala Ser Tyr Arg Tyr Ser Gly Val Pro Asp Arg Phe Ser Gly
            50                  55                  60

Ser Gly Ser Gly Thr Asp Phe Thr Leu Thr Ile Ser Ser Leu Gln Ala
65                  70                  75                  80

Glu Asp Val Ala Glu Tyr Phe Cys Gln Gln Phe Asn Ser Tyr Pro Leu
                85                  90                  95

Thr Phe Gly Gly Gly Thr Lys Val Glu Ile Lys
            100                 105
```

<210> SEQ ID NO 50
<211> LENGTH: 321
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: VL4

<400> SEQUENCE: 50

```
gacattcaga tgacccagtc tccatcatcc atgtccgcct cagtaggaga cagggtcacc    60
atcacctgca aggccagtca gaatgtgggt actaatgtag cctggtatca acagaaacca   120
gggaaggctc ctaaaccact gatttactcg gcatcctacc ggtacagtgg agtccctgat   180
cgcttcagcg gcagtggatc tgggacagat ttcactctca ccatcagctc tctgcaggct   240
gaagacgtgg cagagtattt ctgtcagcaa tttaacagct atcctctcac gttcggtggc   300
gggaccaagg tggagattaa a                                             321
```

<210> SEQ ID NO 51
<211> LENGTH: 107
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: VL4

<400> SEQUENCE: 51

```
Asp Ile Gln Met Thr Gln Ser Pro Ser Ser Met Ser Ala Ser Val Gly
1               5                  10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Pro Leu Ile
        35                  40                  45

Tyr Ser Ala Ser Tyr Arg Tyr Ser Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Glu Tyr Phe Cys Gln Gln Phe Asn Ser Tyr Pro Leu
                85                  90                  95

Thr Phe Gly Gly Gly Thr Lys Val Glu Ile Lys
            100                 105
```

<210> SEQ ID NO 52
<211> LENGTH: 460
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: F5.87 H chain

<400> SEQUENCE: 52

```
Met Tyr Leu Gly Leu Asn Tyr Val Phe Ile Val Phe Leu Leu Asn Gly
1               5                  10                  15

Val Gln Ser Glu Val Lys Leu Glu Glu Ser Gly Gly Gly Leu Val Gln
            20                  25                  30

Pro Gly Gly Ser Met Lys Leu Ser Cys Ala Ala Ser Gly Phe Thr Phe
```

```
                35                  40                  45
Ser Asn Ala Trp Met Asp Trp Val Arg Gln Ser Pro Glu Lys Gly Leu
 50                  55                  60
Glu Trp Val Ala Glu Ile Arg Ser Lys Ala Asn Asn His Ala Thr Tyr
 65                  70                  75                  80
Tyr Gly Glu Ser Val Lys Gly Arg Phe Thr Ile Ser Arg Asp Asp Ser
                 85                  90                  95
Lys Ser Ser Val Tyr Leu Gln Met Asn Ser Leu Arg Ala Glu Asp Thr
                100                 105                 110
Gly Ile Tyr Tyr Cys Thr Ala Thr Val Arg Gly Gly Tyr Trp Gly Gln
                115                 120                 125
Gly Thr Thr Leu Thr Val Ser Ser Ala Lys Thr Thr Pro Pro Ser Val
130                 135                 140
Tyr Pro Leu Ala Pro Gly Ser Ala Ala Gln Thr Asn Ser Met Val Thr
145                 150                 155                 160
Leu Gly Cys Leu Val Lys Gly Tyr Phe Pro Glu Pro Val Thr Val Thr
                165                 170                 175
Trp Asn Ser Gly Ser Leu Ser Ser Gly Val His Thr Phe Pro Ala Val
                180                 185                 190
Leu Gln Ser Asp Leu Tyr Thr Leu Ser Ser Val Thr Val Pro Ser
                195                 200                 205
Ser Thr Trp Pro Ser Glu Thr Val Thr Cys Asn Val Ala His Pro Ala
210                 215                 220
Ser Ser Thr Lys Val Asp Lys Lys Ile Val Pro Arg Asp Cys Gly Cys
225                 230                 235                 240
Lys Pro Cys Ile Cys Thr Val Pro Glu Val Ser Ser Val Phe Ile Phe
                245                 250                 255
Pro Pro Lys Pro Lys Asp Val Leu Thr Ile Thr Leu Thr Pro Lys Val
                260                 265                 270
Thr Cys Val Val Val Asp Ile Ser Lys Asp Asp Pro Glu Val Gln Phe
                275                 280                 285
Ser Trp Phe Val Asp Asp Val Glu Val His Thr Ala Gln Thr Gln Pro
                290                 295                 300
Arg Glu Glu Gln Phe Asn Ser Thr Phe Arg Ser Val Ser Glu Leu Pro
305                 310                 315                 320
Ile Met His Gln Asp Trp Leu Asn Gly Lys Glu Phe Lys Cys Arg Val
                325                 330                 335
Asn Ser Ala Ala Phe Pro Ala Pro Ile Glu Lys Thr Ile Ser Lys Thr
                340                 345                 350
Lys Gly Arg Pro Lys Ala Pro Gln Val Tyr Thr Ile Pro Pro Pro Lys
                355                 360                 365
Glu Gln Met Ala Lys Asp Lys Val Ser Leu Thr Cys Met Ile Thr Asp
                370                 375                 380
Phe Phe Pro Glu Asp Ile Thr Val Glu Trp Gln Trp Asn Gly Gln Pro
385                 390                 395                 400
Ala Glu Asn Tyr Lys Asn Thr Gln Pro Ile Met Asp Thr Asp Gly Ser
                405                 410                 415
Tyr Phe Val Tyr Ser Lys Leu Asn Val Gln Lys Ser Asn Trp Glu Ala
                420                 425                 430
Gly Asn Thr Phe Thr Cys Ser Val Leu His Glu Gly Leu His Asn His
                435                 440                 445
His Thr Glu Lys Ser Leu Ser His Ser Pro Gly Lys
                450                 455                 460
```

<210> SEQ ID NO 53
<211> LENGTH: 1383
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: F5.87 H chain

<400> SEQUENCE: 53

| | | | | | |
|---|---|---|---|---|---|
| atgtacttgg | gactgaacta | tgtattcata | gttttttctct | taaatggtgt | ccagagtgaa | 60 |
| gtgaagcttg | aggagtctgg | aggaggcttg | gtgcaacctg | gaggatccat | gaaactctct | 120 |
| tgtgctgcct | ctggattcac | ttttagtaac | gcctggatgg | actgggtccg | ccagtctcca | 180 |
| gagaaggggc | ttgagtgggt | tgctgaaatt | agaagcaaag | ctaataatca | tgcaacatac | 240 |
| tatggtgagt | ctgtgaaagg | gaggttcacc | atctcaagag | atgattccaa | agtagtgtc | 300 |
| tacctgcaaa | tgaacagttt | aagagctgaa | gacactggca | tttattactg | taccgcaact | 360 |
| gtgagagggg | gctactgggg | ccaaggcacc | actctcacag | tctcctcagc | caaaacgaca | 420 |
| cccccatctg | tctatccact | ggcccctgga | tctgctgccc | aaactaactc | catggtgacc | 480 |
| ctgggatgcc | tggtcaaggg | ctatttccct | gagccagtga | cagtgacctg | gaactctgga | 540 |
| tccctgtcca | gcggtgtgca | caccttccca | gctgtcctgc | agtctgacct | ctacactctg | 600 |
| agcagctcag | tgactgtccc | ctccagcacc | tggcccagcg | agaccgtcac | ctgcaacgtt | 660 |
| gcccacccgg | ccagcagcac | caaggtggac | aagaaaattg | tgcccaggga | ttgtggttgt | 720 |
| aagccttgca | tatgtacagt | cccagaagta | tcatctgtct | tcatcttccc | cccaaagccc | 780 |
| aaggatgtgc | tcaccattac | tctgactcct | aaggtcacgt | gtgttgtggt | agacatcagc | 840 |
| aaggatgatc | ccgaggtcca | gttcagctgg | tttgtagatg | atgtggaggt | gcacacagct | 900 |
| cagacgcaac | cccgggagga | gcagttcaac | agcactttcc | gctcagtcag | tgaacttccc | 960 |
| atcatgcacc | aggactggct | caatggcaag | gagttcaaat | gcagggtcaa | cagtgcagct | 1020 |
| ttccctgccc | ccatcgagaa | aaccatctcc | aaaaccaaag | gcagaccgaa | ggctccacag | 1080 |
| gtgtacacca | ttccacctcc | caaggagcag | atggccaagg | ataaagtcag | tctgacctgc | 1140 |
| atgataacag | acttcttccc | tgaagacatt | actgtggagt | ggcagtggaa | tgggcagcca | 1200 |
| gcggagaact | acaagaacac | tcagcccatc | atggacacag | atggctctta | cttcgtctac | 1260 |
| agcaagctca | atgtgcagaa | gagcaactgg | gaggcaggaa | atactttcac | ctgctctgtg | 1320 |
| ttacatgagg | gcctgcacaa | ccaccatact | gagaagagcc | tctcccactc | tcctggtaaa | 1380 |
| tga | | | | | | 1383 |

<210> SEQ ID NO 54
<211> LENGTH: 236
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: F5.87 L chain

<400> SEQUENCE: 54

Met Asp Met Arg Thr Pro Ala Gln Phe Leu Gly Ile Leu Leu Leu Trp
 1               5                   10                  15

Phe Pro Gly Ile Lys Cys Asp Ile Lys Met Thr Gln Ser Pro Ser Ser

```
                    20                  25                  30
Met Tyr Ala Ser Leu Gly Glu Arg Val Thr Ile Thr Cys Lys Ala Ser
                35                  40                  45

Gln Asp Ile Asn Ser Tyr Leu Ser Trp Phe Gln Gln Lys Pro Gly Lys
            50                  55                  60

Ser Pro Lys Thr Leu Ile Tyr Arg Ala Asn Arg Leu Val Asp Gly Val
 65                  70                  75                  80

Pro Ser Arg Phe Ser Gly Ser Gly Ser Gly Gln Asp Tyr Ser Leu Thr
                85                  90                  95

Ile Ser Ser Leu Glu Tyr Glu Asp Met Gly Ile Tyr Tyr Cys Leu Gln
            100                 105                 110

Tyr Asp Glu Tyr Pro Tyr Thr Phe Gly Gly Gly Thr Lys Leu Glu Ile
        115                 120                 125

Lys Arg Ala Asp Ala Ala Pro Thr Val Ser Ile Phe Pro Pro Ser Ser
130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
            180                 185                 190

Ser Thr Tyr Ser Met Ser Ser Thr Leu Thr Leu Thr Lys Asp Glu Tyr
        195                 200                 205

Glu Arg His Asn Ser Tyr Thr Cys Glu Ala Thr His Lys Thr Ser Thr
    210                 215                 220

Ser Pro Ile Val Lys Ser Phe Asn Arg Asn Glu Cys
225                 230                 235

<210> SEQ ID NO 55
<211> LENGTH: 711
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: F5.87 L chain

<400> SEQUENCE: 55
atggacatga ggacccctgc tcagtttctt ggaatcttgt tgctctggtt tccaggtatc      60
aaatgtgaca tcaagatgac ccagtctcca tcttccatgt atgcatctct aggagagaga    120
gtcactatca cttgcaaggc gagtcaggac attaatagct atttaagctg gttccagcag    180
aaaccaggga aatctcctaa gaccctgatc tatcgtgcaa acagattggt agatggggtc    240
ccatcaaggt tcagtggcag tggatctggg caagattatt ctctcaccat cagcagcctg    300
gagtatgaag atatgggaat ttattattgt ctacagtatg atgagtatcc gtacacattc    360
ggagggggga ccaagctgga aataaaacgg gctgatgctg caccaactgt atccatcttc    420
ccaccatcca gtgagcagtt aacatctgga ggtgcctcag tcgtgtgctt cttgaacaac    480
ttctacccca agacatcaa tgtcaagtgg aagattgatg gcagtgaacg acaaaatggc    540
gtcctgaaca gttggactga tcaggacagc aaagacagca cctacagcat gagcagcacc    600
ctcacgttga ccaaggacga gtatgaacga cataacagct atacctgtga ggccactcac    660
aagacatcaa cttcacccat tgtcaagagc ttcaacagga tgagtgtta g              711
```

```
<210> SEQ ID NO 56
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Consensus mouse single sequences H chain

<400> SEQUENCE: 56

Met Gly Trp Ser Leu Ile Leu Leu Phe Leu Val Ala Val Ala Thr Arg
1               5                   10                  15

Val His Ser

<210> SEQ ID NO 57
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Consensus mouse single sequences L chain

<400> SEQUENCE: 57

Met Arg Val Pro Ala Gln Leu Leu Gly Leu Leu Leu Leu Trp Leu Pro
1               5                   10                  15

Gly Ala Arg Cys
            20
```